(12) United States Patent
Murakami et al.

(10) Patent No.: US 11,103,414 B2
(45) Date of Patent: Aug. 31, 2021

(54) ASSISTANCE APPARATUS, ASSISTANCE METHOD, AND RECORDING MEDIUM

(71) Applicant: Panasonic Intellectual Property Management Co., Ltd., Osaka (JP)

(72) Inventors: Kenta Murakami, Osaka (JP); Stephen William John, Nara (JP); Hiroki Takeuchi, Osaka (JP); Shinobu Adachi, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 395 days.

(21) Appl. No.: 16/161,060

(22) Filed: Oct. 16, 2018

(65) Prior Publication Data

US 2019/0125617 A1    May 2, 2019

(30) Foreign Application Priority Data

Oct. 31, 2017    (JP) .............................. JP2017-210886

(51) Int. Cl.
*A61H 3/00* (2006.01)
*A61H 1/02* (2006.01)
*A61B 5/11* (2006.01)

(52) U.S. Cl.
CPC ............... *A61H 3/00* (2013.01); *A61B 5/112* (2013.01); *A61H 1/0244* (2013.01);
(Continued)

(58) Field of Classification Search
CPC ...... A61H 3/00; A61H 1/0266; A61H 1/0237; A61H 1/024; A61H 1/0244; A61H 2201/5061; A61H 2201/5025; A61H 2201/5035; A61H 2201/165; A61H 2201/5046; A61H 2201/5079; A61H 2201/5023; A61H 2201/5071;
(Continued)

(56) References Cited

U.S. PATENT DOCUMENTS

| 2014/0296761 A1* | 10/2014 | Yamamoto ............... A61H 3/00 602/23 |
| 2015/0173993 A1* | 6/2015 | Walsh ........................ A61F 2/68 414/4 |

(Continued)

FOREIGN PATENT DOCUMENTS

| JP | 2009-213538 | 9/2009 |
| JP | 2016-528940 | 9/2016 |

*Primary Examiner* — Quang D Thanh
(74) *Attorney, Agent, or Firm* — Wenderoth, Lind & Ponack, L.L.P.

(57) ABSTRACT

An assistance apparatus includes a first wire and a second wire that couple an upper-body belt and a left knee belt to each other, respectively, a third wire and a fourth wire that couple the upper-body belt and a right knee belt to each other, respectively, and a motor. When assistance is stopped, the motor is configured to reduce tension of the first wire during a first stop period starting in a boundary period in a first period and ending in a start period of a second period, generate no tension in the second wire during the second period, reduce tension of the third wire during a second stop period starting in a boundary period in a third period and ending in a start period of a fourth period, and generate no tension in the fourth wire during the fourth period.

25 Claims, 31 Drawing Sheets

(52) U.S. Cl.
CPC ........... *A61H 1/0262* (2013.01); *A61H 3/008* (2013.01); *A61H 1/0255* (2013.01); *A61H 2003/007* (2013.01); *A61H 2201/1207* (2013.01); *A61H 2201/1215* (2013.01); *A61H 2201/14* (2013.01); *A61H 2201/149* (2013.01); *A61H 2201/16* (2013.01); *A61H 2201/163* (2013.01); *A61H 2201/1642* (2013.01); *A61H 2201/1652* (2013.01); *A61H 2201/5012* (2013.01); *A61H 2201/5025* (2013.01); *A61H 2201/5033* (2013.01); *A61H 2201/5035* (2013.01); *A61H 2201/5061* (2013.01); *A61H 2201/5079* (2013.01); *A61H 2201/5084* (2013.01); *A61H 2201/5097* (2013.01); *A61H 2230/60* (2013.01)

(58) Field of Classification Search
CPC .... A61H 2201/0192; A61H 2201/1238; A61H 2201/5069; A61H 2201/5028; A61H 2205/10; A61H 2201/14; A61H 2201/50; A61H 2003/007; A61H 2201/1215; A61H 2201/149; A61H 2201/5097; A61H 2201/1642; A61H 2201/1652; A61H 2201/5007; A61H 2201/5012; A61H 2201/5084; A61H 2201/163; A61B 5/1125; A61B 5/1038; A61B 5/112; A61B 2562/0219; A61B 2562/0257; A61B 2505/09

See application file for complete search history.

(56) References Cited

U.S. PATENT DOCUMENTS

| | | | |
|---|---|---|---|
| 2016/0107309 A1* | 4/2016 | Walsh | A61H 3/00 248/550 |
| 2017/0202724 A1 | 7/2017 | De Rossi et al. | |
| 2019/0125615 A1* | 5/2019 | Murakami | A61B 5/112 |
| 2019/0125616 A1* | 5/2019 | John | A61H 1/0244 |

* cited by examiner

LEFT LEG EXTENSION
110a2 → HIGH TENSION

RIGHT LEG EXTENSION
110a4 → HIGH TENSION

LEFT LEG EXTENSION
110a2 → HIGH TENSION
110a6 → HIGH TENSION

RIGHT LEG EXTENSION
110a4 → HIGH TENSION
110a8 → HIGH TENSION

ASSISTANCE APPARATUS, ASSISTANCE METHOD, AND RECORDING MEDIUM

BACKGROUND

1. Technical Field

The present disclosure relates to an assistance apparatus, an assistance method, and a recording medium for assisting a wearer in walking.

2. Description of the Related Art

For example, Japanese Unexamined Patent Application Publication No. 2009-213538 discloses an assistant outfit for assisting movements of joints of a user. The disclosed assistant outfit includes a thigh link to be attached to a thigh, a thigh restraint band that restrains movement of the thigh link, a lower-leg link to be attached to a lower leg, a lower-leg restraint band that restrains movement of the lower-leg link, and a knee assistant motor that changes the angle between the thigh link and the lower-leg link. Japanese Unexamined Patent Application Publication (Translation of PCT Application) No. 2016-528940 discloses a soft exosuit equipped with an actuator including an operating member. In the soft exosuit, activation of the actuator generates a moment around a joint of a user wearing the soft exosuit to assist the movement of the user.

SUMMARY

A need exists to provide assistance for movements of a user in different ways in accordance with the state of the user, such as whether the user is carrying an object such as luggage. A specific method for addressing this issue is not described in Japanese Unexamined Patent Application Publication No. 2009-213538 or Japanese Unexamined Patent Application Publication (Translation of PCT Application) No. 2016-528940.

One non-limiting and exemplary embodiment provides an assistance apparatus, an assistance method, and a recording medium that provide assistance in accordance with the state of a user.

In one general aspect, the techniques disclosed here feature an assistance apparatus including an upper-body belt to be worn on an upper half of a body of a user, a left knee belt to be worn on a left knee of the user, a right knee belt to be worn on a right knee of the user, a first wire that couples the upper-body belt and the left knee belt to each other on or above a front part of the body of the user, a second wire that couples the upper-body belt and the left knee belt to each other on or above a back part of the body of the user, a third wire that couples the upper-body belt and the right knee belt to each other on or above the front part of the body of the user, a fourth wire that couples the upper-body belt and the right knee belt to each other on or above the back part of the body of the user, and at least one motor. In first assistance for assisting the user in walking while carrying an object, the at least one motor generates (i) a tension greater than or equal to a first threshold value in the first wire during a first period, the first period being a period of 35% or more and 90% or less of a gait phase of a left leg of the user, (ii) a tension greater than or equal to the first threshold value in the second wire during a second period, the second period being a period of 0% or more and 25% or less and 65% or more and less than 100% of the gait phase of the left leg, (iii) a tension greater than or equal to the first threshold value in the third wire during a third period, the third period being a period of 35% or more and 90% or less of a gait phase of a right leg of the user, (iv) a tension greater than or equal to the first threshold value in the fourth wire during a fourth period, the fourth period being a period of 0% or more and 25% or less and 65% or more and less than 100% of the gait phase of the right leg, (v) a tension less than a second threshold value in the first wire during a fifth period, the fifth period being a period of 0% or more and less than 100% of the gait phase of the left leg, except the first period, (vi) a tension greater than or equal to the second threshold value in the second wire during a sixth period, the sixth period being a period of 0% or more and less than 100% of the gait phase of the left leg, except the second period, (vii) a tension less than the second threshold value in the third wire during a seventh period, the seventh period being a period of 0% or more and less than 100% of the gait phase of the right leg, except the third period, and (viii) a tension greater than or equal to the second threshold value in the fourth wire during an eighth period, the eighth period being a period of 0% or more and less than 100% of the gait phase of the right leg, except the fourth period. The first threshold value is larger than the second threshold value. When the assistance apparatus stops the first assistance, the at least one motor makes a tension of the first wire less than the first threshold value during a first stop period, the first stop period being a period starting in a boundary period in the first period and ending in a start period of the second period, and does not generate a tension greater than or equal to the first threshold value in the second wire during the second period, and the at least one motor makes a tension of the third wire less than the first threshold value during a second stop period, the second stop period being a period starting in a boundary period in the third period and ending in a start period of the fourth period, and does not generate a tension greater than or equal to the first threshold value in the fourth wire during the fourth period. The boundary period in the first period includes a timing at which the left leg of the user shifts from a stance phase to a swing phase, and the boundary period in the third period includes a timing at which the right leg of the user shifts from the stance phase to the swing phase.

It should be noted that general or specific embodiments may be implemented as a system, an apparatus, a method, an integrated circuit, a computer program, a computer-readable recording medium such as a recording disk, or any selective combination thereof. The computer-readable recording medium includes a non-volatile recording medium such as a compact disc-read only memory (CD-ROM).

An assistance apparatus and so on according to aspects of the present disclosure can provide assistance in accordance with the state of a user. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
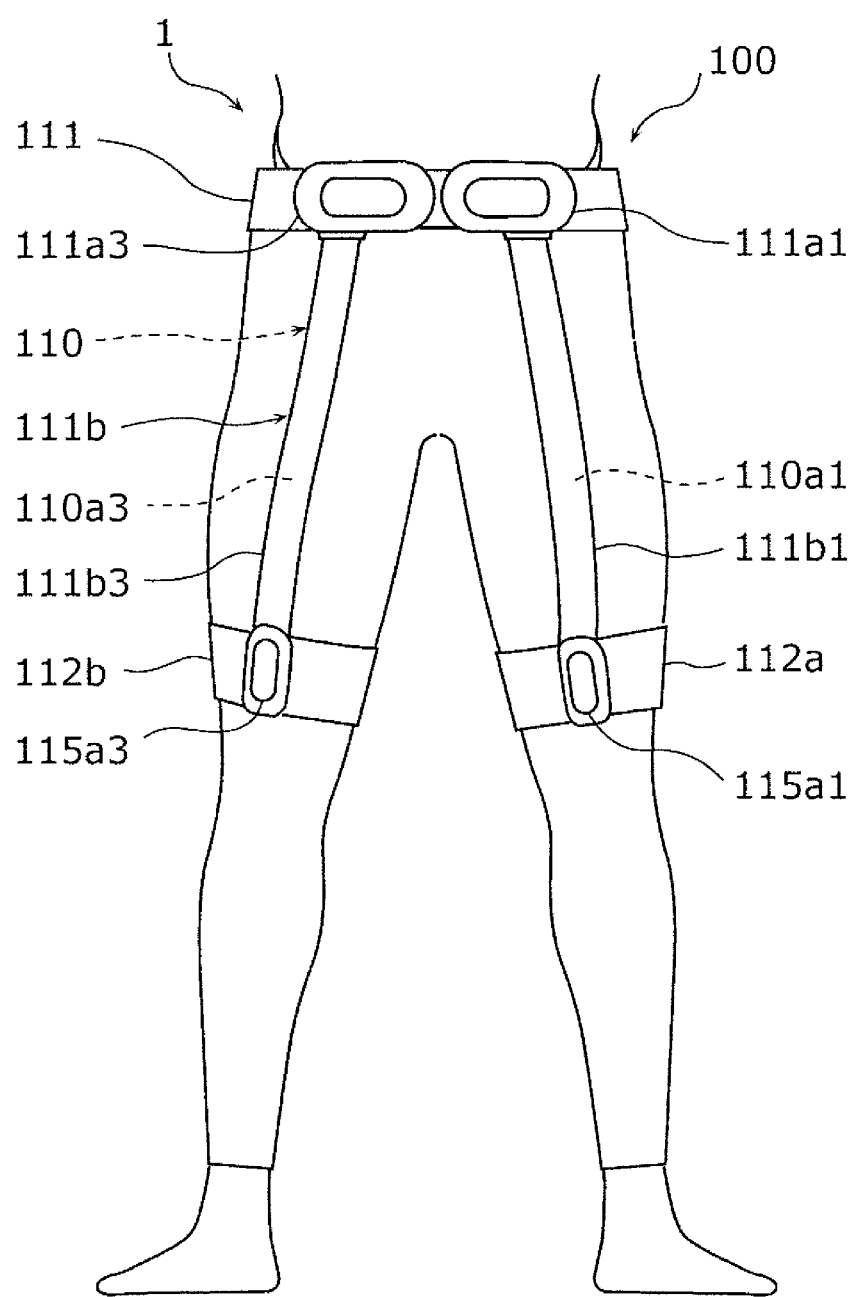
FIG. 1 is a front view of a user wearing an assistance apparatus according to an embodiment, as viewed from the front.

Underlying Knowledge Forming Basis of the Present Disclosure

The inventors of the present disclosure, or the present inventors, have studied the techniques described in Japanese Unexamined Patent Application Publication No. 2009-213538 (hereinafter referred to as "Patent Literature 1") and Japanese Unexamined Patent Application Publication (Translation of PCT Application) No. 2016-528940 (hereinafter referred to as "Patent Literature 2") mentioned in the "BACKGROUND" section and have examined techniques for supporting, or assisting, a user in walking. The present inventors have focused on changing states of a user, who is a wearer of an assistance apparatus. For example, it is necessary that an assistance method for a user who is carrying an object such as luggage be different from an assistance method for a user who is carrying no object.

First, the present inventors have examined an assistance apparatus that assists a user in walking by applying forces generated by motors to the user through wires. To enable various kinds of assistance on the legs of a user, the present inventors have developed an assistance apparatus including wires, each of which is to be placed so as to extend across one of the front of the hip joint of the left leg of the user, the back of the hip joint of the left leg of the user, the front of the hip joint of the right leg of the user, and the back of the hip joint of the right leg of the user. The present inventors have further developed a configuration in which the wires are each coupled to an upper-body belt and a left knee belt or a right knee belt, which are to be attached to the body of the user, and are accordingly attached to the body of the user. Thus, the present inventors have devised an assistance apparatus having a simple configuration.

For example, Patent Literature 1 discloses an assistant outfit including a rod-shaped thigh link that is attached to a side portion of a thigh, and a rod-shaped lower-leg link that is attached to a side portion of a lower leg. The thigh link and the lower-leg link are coupled to a knee assistant motor. The knee assistant motor is driven to change the angle defined by the thigh link and the lower-leg link, and accordingly the assistant outfit assists flexion and extension of the knee of the user. The thigh link, the lower-leg link, and the knee assistant motor are attached to each of the side portion of the right leg of the user and the side portion of the left leg of the user, resulting in the assistant outfit disclosed in Patent Literature 1 having a structure that is large-scale and complicated for the user. Thus, the assistant outfit places a heavy burden on the user.

In Patent Literature 2, tension is applied to connection elements of the soft exosuit, which is worn on a part of the body of the user from the waist to a thigh and a lower leg, through a cable placed at the front part of the thigh of the user, thereby assisting flexion and extension of the knee of the user. In the soft exosuit disclosed in Patent Literature 2, the connection elements and so on, which are attached to the body of the user, are large-scale and complicated for the user. Thus, the soft exosuit places a heavy burden on the user.

In addition, none of Patent Literatures 1 and 2 discloses the details of a method for providing assistance in accordance with the state of a user. Accordingly, the present inventors have devised the following technique for providing assistance in accordance with the state of a user by using the assistance apparatus having a simple configuration described above.

An assistance apparatus according to an aspect of the present disclosure is an assistance apparatus including an upper-body belt to be worn on an upper half of a body of a user, a left knee belt to be worn on a left knee of the user, a right knee belt to be worn on a right knee of the user, a first wire that couples the upper-body belt and the left knee belt to each other on or above a front part of the body of the user, a second wire that couples the upper-body belt and the left knee belt to each other on or above a back part of the body of the user, a third wire that couples the upper-body belt and the right knee belt to each other on or above the front part of the body of the user, a fourth wire that couples the upper-body belt and the right knee belt to each other on or above the back part of the body of the user, and at least one motor. In first assistance for assisting the user in walking while carrying an object, the at least one motor generates (i) a tension greater than or equal to a first threshold value in the first wire during a first period, the first period being a period of 35% or more and 90% or less of a gait phase of a left leg of the user, (ii) a tension greater than or equal to the first threshold value in the second wire during a second period, the second period being a period of 0% or more and 25% or less and 65% or more and less than 100% of the gait phase of the left leg, (iii) a tension greater than or equal to the first threshold value in the third wire during a third period, the third period being a period of 35% or more and 90% or less of a gait phase of a right leg of the user, (iv) a tension greater than or equal to the first threshold value in the fourth wire during a fourth period, the fourth period being a period of 0% or more and 25% or less and 65% or more and less than 100% of the gait phase of the right leg, (v) a tension less than a second threshold value in the first wire during a fifth period, the fifth period being a period of 0% or more and less than 100% of the gait phase of the left leg, except the first period, (vi) a tension greater than or equal to the second threshold value in the second wire during a sixth period, the sixth period being a period of 0% or more and less than 100% of the gait phase of the left leg, except the second period, (vii) a tension less than the second threshold value in the third wire during a seventh period, the seventh period being a period of 0% or more and less than 100% of the gait phase of the right leg, except the third period, and (viii) a tension greater than or equal to the second threshold value in the fourth wire during an eighth period, the eighth period being a period of 0% or more and less than 100% of the gait phase of the right leg, except the fourth period. The first threshold value is larger than the second threshold value. When the assistance apparatus stops the first assistance, the at least one motor makes a tension of the first wire less than the first threshold value during a first stop period, the first stop period being a period starting in a boundary period in the first period and ending in a start period of the second period, and does not generate a tension greater than or equal to the first threshold value in the second wire during the second period, and the at least one motor makes a tension of the third wire less than the first threshold value during a second stop period, the second stop period being a period starting in a boundary period in the third period and ending in a start period of the fourth period, and does not generate a tension greater than or equal to the first threshold value in the fourth wire during the fourth period. The boundary period in the first period includes a timing at which the left leg of the user shifts from a stance phase to a swing phase, and the boundary period in the third period includes a timing at which the right leg of the user shifts from the stance phase to the swing phase.

In the configuration described above, the tension generated in the first wire can apply an assistance force for flexion to the left leg of the user, and the tension generated in the third wire can apply an assistance force for flexion to the right leg of the user. The tension generated in the second wire can apply an assistance force for extension to the left leg of the user, and the tension generated in the fourth wire can apply an assistance force for extension to the right leg of the user. The assistance apparatus generates a tension greater than or equal to the first threshold value in the first wire during the first period in the gait phase of the left leg to assist flexion of the left leg, and generates a tension greater than or equal to the first threshold value in the third wire during the third period in the gait phase of the right leg to assist flexion of the right leg, thereby assisting the user in walking. Further, the assistance apparatus sets the tension of the first wire to be less than the second threshold value during the fifth period in the gait phase of the left leg and sets the tension of the third wire to be less than the second threshold value during the seventh period in the gait phase of the right leg to weaken assistance for flexion or provide no assistance for flexion, thereby reducing an influence on extension of the legs. Further, the assistance apparatus generates a tension greater than or equal to the first threshold value in the second wire during the second period in the gait phase of the left leg to assist extension of the left leg, and generates a tension greater than or equal to the first threshold value in the fourth wire during the fourth period in the gait phase of the right leg to assist extension of the right leg, thereby assisting the user in walking. Further, the assistance apparatus makes the tension of the second wire greater than or equal to the second threshold value during the sixth period in the gait phase of the left leg to assist extension of the left leg, and makes the tension of the fourth wire greater than or equal to the second threshold value during the eighth period in the gait phase of the right leg to assist extension of the right leg. This may keep the center of gravity of the body of the user, who is carrying an object, at the position in the upright posture of the user. Thus, the assistance apparatus can assist a user in walking while carrying an object, with the user being kept in a stable posture. The first threshold value may be a tension value that allows the user to recognize that the movement of a leg is promoted by a tension generated in a wire, and may be 40 newtons (N), for example. The second threshold value may be a tension value that prevents a wire from loosening, and may be a value that is 0.2 to 0.4 times the first threshold value or 10 N, for example.

The first stop period is a period from a timing at which the state of the left leg to which assistance for flexion is being applied changes from the stance phase to the swing phase until the subsequent assistance, that is, assistance for extension, is substantially applied to the left leg. The second stop period is a period from a timing at which the state of the right leg to which assistance for flexion is being applied, changes from the stance phase to the swing phase until the subsequent assistance, that is, assistance for extension, is substantially applied to the right leg.

The assistance apparatus does not provide assistance for flexion for generating a tension greater than or equal to the first threshold value in the first wire of the left leg, that is, stops assisting flexion for walking, during the first stop period. Further, the assistance apparatus does not provide assistance for extension for generating a tension greater than or equal to the first threshold value in the second wire of the left leg, that is, stops assisting extension for walking, during the second period. Thus, the assistance apparatus stops assisting the left leg for walking.

Further, the assistance apparatus does not provide assistance for flexion for generating a tension greater than or equal to the first threshold value in the third wire of the right leg, that is, stops assisting flexion for walking, during the third stop period. Further, the assistance apparatus does not provide assistance for extension for generating a tension greater than or equal to the first threshold value in the fourth wire of the right leg, that is, stops assisting extension for walking, during the fourth period. Thus, the assistance apparatus stops assisting the right leg for walking.

Moreover, the assistance apparatus described above stops assisting the left and right legs for walking when the left and right legs are in similar states. The timing of stopping assisting the left leg for walking may be shifted from the timing of stopping assisting the right leg for walking. This prevents the user from losing the balance between the movements of the left and right legs. Thus, the assistance apparatus described above can provide assistance to the user in accordance with the state of the user.

In the assistance apparatus according to the aspect of the present disclosure, the left leg may shift from the stance phase to the swing phase during the first period, the left leg may shift from the swing phase to the stance phase during the second period, the right leg may shift from the stance phase to the swing phase during the third period, and the right leg may shift from the swing phase to the stance phase during the fourth period.

In the configuration described above, the assistance apparatus assists flexion during the first period in which the left leg shifts from the stance phase to the swing phase, and assists flexion during the third period in which the right leg shifts from the stance phase to the swing phase. Thus, the assistance apparatus can effectively assist the user in walking. Further, the assistance apparatus assists extension during the second period in which the left leg shifts from the swing phase to the stance phase, and assists extension during the fourth period in which the right leg shifts from the swing phase to the stance phase. Thus, the assistance apparatus can effectively assist the user in walking.

In the assistance apparatus according to the aspect of the present disclosure, the first stop period and the second stop period may not overlap.

In the configuration described above, the assistance apparatus completely shifts the timing of stopping assisting the left leg for walking and the timing of stopping assisting the right leg for walking from each other. For example, if the assistance apparatus stops assisting the left and right legs for walking at similar timings, the user can lose the balance between the movements of the left and right legs and can fall. However, the assistance apparatus described above can stop assisting the left and right legs for walking while keeping the balance between the movements of the left and right legs.

In the assistance apparatus according to the aspect of the present disclosure, the first stop period may be a period of 55% or more and 95% or less of the gait phase of the left leg, and the second stop period may be a period of 55% or more and 95% or less of the gait phase of the right leg.

In the assistance apparatus according to the aspect of the present disclosure, when the assistance apparatus stops the first assistance, the at least one motor may make the tension of the first wire less than the second threshold value during the first stop period and keep the tension of the second wire greater than or equal to the second threshold value during the second period, the at least one motor may make the tension of the third wire less than the second threshold value during the third stop period and keep the tension of the fourth wire greater than or equal to the second threshold value during the fourth period, and the at least one motor may decrease the tension of the second wire and the tension of the fourth wire to a tension less than the second threshold value after the first stop period and the third stop period, respectively.

In the configuration described above, after stopping assisting the left leg for walking, the assistance apparatus continues assistance for extension using the second wire for keeping the center of gravity of the body of the user at a position in the upright posture, and, after stopping assisting the right leg for walking, the assistance apparatus continues assistance for extension using the fourth wire for keeping the center of gravity of the body of the user at a position in the upright posture. Further, after stopping assisting the left and right legs for walking, the assistance apparatus decreases the assistance force for extension with the second wire and the fourth wire. Thus, the assistance apparatus can prevent instability of the user, who is carrying an object, due to stopping of assistance for the left and right legs for walking.

In the assistance apparatus according to the aspect of the present disclosure, the at least one motor may start decreasing the tension of the second wire and the tension of the fourth wire at the same timing after the first stop period and the third stop period, respectively, and progressively decrease the tension of the second wire and the tension of the fourth wire in a similar manner in accordance with progression of the gait phase of the left leg and the gait phase of the right leg, respectively.

In the configuration described above, the assistance apparatus uniformly decreases the assistance forces for extension of the left and right legs using the second wire and the fourth wire for keeping the center of gravity of the body of the user at a position in the upright posture. This prevents the user from losing the balance between the left and right legs due to the decrease of the assistance forces.

In the assistance apparatus according to the aspect of the present disclosure, the at least one motor may include a first motor, a second motor, a third motor, and a fourth motor. The first wire may have a first end fixed to the left knee belt, and the first wire may have a second end fixed to the first motor. The second wire may have a first end fixed to the left knee belt, and the second wire may have a second end fixed to the second motor. The third wire may have a first end fixed to the right knee belt, and the third wire may have a second end fixed to the third motor. The fourth wire may have a first end fixed to the right knee belt, and the fourth wire may have a second end fixed to the fourth motor.

In the configuration described above, the assistance apparatus can separately control the tension of the first wire, the tension of the second wire, the tension of the third wire, and the tension of the fourth wire. Thus, the assistance apparatus can provide fine assistance.

The assistance apparatus according to the aspect of the present disclosure may further include a fifth wire that couples the upper-body belt and the left knee belt to each other and that extends on or above the front part of the body of the user in a direction crossing a direction in which the first wire extends, a sixth wire that couples the upper-body belt and the left knee belt to each other and that extends on or above the back part of the body of the user in a direction crossing a direction in which the second wire extends, a seventh wire that couples the upper-body belt and the right knee belt to each other and that extends on or above the front part of the body of the user in a direction crossing a direction in which the third wire extends, and an eighth wire that couples the upper-body belt and the right knee belt to each other and that extends on or above the back part of the body of the user in a direction crossing a direction in which the fourth wire extends. In the first assistance, the at least one motor may generate (i) a tension greater than or equal to the first threshold value in the first wire and the fifth wire during the first period, (ii) a tension greater than or equal to the first threshold value in the second wire and the sixth wire during the second period, (iii) a tension greater than or equal to the first threshold value in the third wire and the seventh wire during the third period, (iv) a tension greater than or equal to the first threshold value in the fourth wire and the eighth wire during the fourth period, (v) a tension less than the second threshold value in the first wire and the fifth wire during the fifth period, (vi) a tension greater than or equal to the second threshold value in the second wire and the sixth wire during the sixth period, (vii) a tension less than the second threshold value in the third wire and the seventh wire during the seventh period, and (viii) a tension greater than or equal to the second threshold value in the fourth wire and the eighth wire during the eighth period.

In the configuration described above, the tension generated in the first wire and the tension generated in the fifth wire can apply an assistance force for flexion to the left leg of the user. The tension generated in the second wire and the tension generated in the sixth wire can apply an assistance force for extension to the left leg of the user. The tension generated in the third wire and the tension generated in the seventh wire can apply an assistance force for flexion to the right leg of the user. The tension generated in the fourth wire and the tension generated in the eighth wire can apply an assistance force for extension to the right leg of the user.

Thus, the assistance apparatus including the first to eighth wires can provide assistance similar to that of the assistance apparatus including the first to fourth wires. In addition, the assistance apparatus including the first to eighth wires separately controls the tensions of the first to eighth wires, thereby providing more types of assistance. For example, the tension generated in the first wire and the tension generated in the fifth wire may be the same or different, and a different type of assistance can be provided in each case.

In the assistance apparatus according to the aspect of the present disclosure, a time point of 50% of the gait phase of the left leg may correspond to a time point of 0% of the gait phase of the right leg, and a time point of 50% of the gait phase of the right leg may correspond to a time point of 0% of the gait phase of the left leg.

The assistance apparatus according to the aspect of the present disclosure may further include a control circuit and a memory. The memory may store a program for controlling the at least one motor. The control circuit may control the at least one motor in accordance with the program.

The assistance apparatus according to the aspect of the present disclosure may further include a sensor that detects a gait cycle of the user. The control circuit may calculate the gait phase of the left leg and the gait phase of the right leg based on a sensor value of the sensor.

In the configuration described above, the assistance apparatus can assist the user in walking on the basis of a gait phase corresponding to a gait cycle of the user. Thus, the assistance apparatus can provide assistance based on actual user walking.

The assistance apparatus according to the aspect of the present disclosure may further include an interface device. The control circuit may accept selection of an assistance method including the first assistance via the interface device. The control circuit may control the at least one motor in accordance with the assistance method.

In the configuration described above, the assistance apparatus enables selection of an assistance method desired by the user.

An assistance method according to another aspect of the present disclosure is an assistance method for assisting a movement of a user by using wires attached to a body of the user. The assistance method includes coupling, using a first wire among the wires, an upper-body belt and a left knee belt to each other on or above a front part of the body of the user, the upper-body belt being a belt to be worn on an upper half of the body of the user, the left knee belt being a belt to be worn on a left knee of the user; coupling, using a second wire among the wires, the upper-body belt and the left knee belt to each other on or above a back part of the body of the user; coupling, using a third wire among the wires, the upper-body belt and a right knee belt to each other on or above the front part of the body of the user, the right knee belt being a belt to be worn on a right knee of the user; coupling, using a fourth wire among the wires, the upper-body belt and the right knee belt to each other on or above the back part of the body of the user; in first assistance for assisting the user in walking while carrying an object, generating a tension greater than or equal to a first threshold value in the first wire during a first period, the first period being a period of 35% or more and 90% or less of a gait phase of a left leg of the user; generating a tension greater than or equal to the first threshold value in the second wire during a second period, the second period being a period of 0% or more and 25% or less and 65% or more and less than 100% of the gait phase of the left leg; generating a tension greater than or equal to the first threshold value in the third wire during a third period, the third period being a period of 35% or more and 90% or less of a gait phase of a right leg of the user; generating a tension greater than or equal to the first threshold value in the fourth wire during a fourth period, the fourth period being a period of 0% or more and 25% or less and 65% or more and less than 100% of the gait phase of the right leg; generating a tension less than a second threshold value in the first wire during a fifth period, the fifth period being a period of 0% or more and less than 100% of the gait phase of the left leg, except the first period; generating a tension greater than or equal to the second threshold value in the second wire during a sixth period, the sixth period being a period of 0% or more and less than 100% of the gait phase of the left leg, except the second period; generating a tension less than the second threshold value in the third wire during a seventh period, the seventh period being a period of 0% or more and less than 100% of the gait phase of the right leg, except the third period; and generating a tension greater than or equal to the second threshold value in the fourth wire during an eighth period, the eighth period being a period of 0% or more and less than 100% of the gait phase of the right leg, except the fourth period, the first threshold value being larger than the second threshold value; and when stopping the first assistance, making a tension of the first wire less than the first threshold value during a first stop period, the first stop period being a period starting in a boundary period in the first period and ending in a start period of the second period, and not generating a tension greater than or equal to the first threshold value in the second wire during the second period; and making a tension of the third wire less than the first threshold value during a second stop period, the second stop period being a period starting in a boundary period in the third period and ending in a start period of the fourth period, and not generating a tension greater than or equal to the first threshold value in the fourth wire during the fourth period. The boundary period in the first period includes a timing at which the left leg of the user shifts from a stance phase to a swing phase, and the boundary period in the third period includes a timing at which the right leg of the user shifts from the stance phase to the swing phase. The tension of the first wire, the tension of the second wire, the tension of the third wire, and the tension of the fourth wire are adjusted by at least one motor that is controlled by a control circuit. The assistance method according to the aspect described above can achieve advantages similar to those of the assistance apparatus according to the aspect of the present disclosure.

In the assistance method according to the aspect of the present disclosure, the left leg may shift from the stance phase to the swing phase during the first period, the left leg may shift from the swing phase to the stance phase during the second period, the right leg may shift from the stance phase to the swing phase during the third period, and the right leg may shift from the swing phase to the stance phase during the fourth period.

In the assistance method according to the aspect of the present disclosure, the first stop period and the second stop period may not overlap.

In the assistance method according to the aspect of the present disclosure, the first stop period may be a period of 55% or more and 95% or less of the gait phase of the left leg, and the second stop period may be a period of 55% or more and 95% or less of the gait phase of the right leg.

The assistance method according to the aspect of the present disclosure may further include, when stopping the first assistance, making the tension of the first wire less than the second threshold value during the first stop period and keeping the tension of the second wire greater than or equal to the second threshold value during the second period; making the tension of the third wire less than the second threshold value during the third stop period and keeping the tension of the fourth wire greater than or equal to the second threshold value during the fourth period; and decreasing the tension of the second wire and the tension of the fourth wire to a tension less than the second threshold value after the first stop period and the third stop period, respectively.

In the assistance method according to the aspect of the present disclosure, the tension of the second wire and the tension of the fourth wire may be started to decrease at the same timing after the first stop period and the third stop period, respectively, and the tension of the second wire and the tension of the fourth wire may be progressively decreased in a similar manner in accordance with progression of the gait phase of the left leg and the gait phase of the right leg, respectively.

In the assistance method according to the aspect of the present disclosure, a first end of the first wire may be fixed to the left knee belt, and a second end of the first wire may be fixed to a first motor among the at least one motor. A first end of the second wire may be fixed to the left knee belt, and a second end of the second wire may be fixed to a second motor among the at least one motor. A first end of the third wire may be fixed to the right knee belt, and a second end of the third wire may be fixed to a third motor among the at least one motor. A first end of the fourth wire may be fixed to the right knee belt, and a second end of the fourth wire may be fixed to a fourth motor among the at least one motor.

The assistance method according to the aspect of the present disclosure may further include coupling, using a fifth wire among the wires, the upper-body belt and the left knee belt to each other, the fifth wire extending on or above the front part of the body of the user in a direction crossing a direction in which the first wire extends; coupling, using a sixth wire among the wires, the upper-body belt and the left knee belt to each other, the sixth wire extending on or above the back part of the body of the user in a direction crossing a direction in which the second wire extends; coupling, using a seventh wire among the wires, the upper-body belt and the right knee belt to each other, the seventh wire extending on or above the front part of the body of the user in a direction crossing a direction in which the third wire extends; coupling, using an eighth wire among the wires, the upper-body belt and the right knee belt to each other, the eighth wire extending on or above the back part of the body of the user in a direction crossing a direction in which the fourth wire extends; and, in the first assistance, generating a tension greater than or equal to the first threshold value in the first wire and the fifth wire during the first period; generating a tension greater than or equal to the first threshold value in the second wire and the sixth wire during the second period; generating a tension greater than or equal to the first threshold value in the third wire and the seventh wire during the third period; generating a tension greater than or equal to the first threshold value in the fourth wire and the eighth wire during the fourth period; generating a tension less than the second threshold value in the first wire and the fifth wire during the fifth period; generating a tension greater than or equal to the second threshold value in the second wire and the sixth wire during the sixth period; generating a tension less than the second threshold value in the third wire and the seventh wire during the seventh period; and generating a tension greater than or equal to the second threshold value in the fourth wire and the eighth wire during the eighth period.

In the assistance method according to the aspect of the present disclosure, a time point of 50% of the gait phase of the left leg may correspond to a time point of 0% of the gait phase of the right leg, and a time point of 50% of the gait phase of the right leg may correspond to a time point of 0% of the gait phase of the left leg.

The assistance method according to the aspect of the present disclosure may further include acquiring a sensor value of a sensor that detects a gait cycle of the user; and calculating the gait phase of the left leg and the gait phase of the right leg based on the sensor value.

The assistance method according to the aspect of the present disclosure may further include accepting selection of an assistance method including the first assistance via an interface device; and generating a tension in the first wire, the second wire, the third wire, and the fourth wire in accordance with the assistance method.

A recording medium according to still another aspect of the present disclosure is a recording medium storing a control program for causing a device including a processor to execute a process. The recording medium is a non-volatile, computer-readable medium. A first wire couples an upper-body belt and a left knee belt to each other on or above a front part of a body of a user, the upper-body belt being a belt to be worn on an upper half of the body of the user, the left knee belt being a belt to be worn on a left knee of the user. A second wire couples the upper-body belt and the left knee belt to each other on or above a back part of the body of the user. A third wire couples the upper-body belt and a right knee belt to each other on or above the front part of the body of the user, the right knee belt being a belt to be worn on a right knee of the user. A fourth wire couples the upper-body belt and the right knee belt to each other on or above the back part of the body of the user. The process includes, in first assistance for assisting the user in walking while carrying an object, causing at least one motor to generate a tension greater than or equal to a first threshold value in the first wire during a first period, the first period being a period of 35% or more and 90% or less of a gait phase of a left leg of the user; causing the at least one motor to generate a tension greater than or equal to the first threshold value in the second wire during a second period, the second period being a period of 0% or more and 25% or less and 65% or more and less than 100% of the gait phase of the left leg; causing the at least one motor to generate a tension greater than or equal to the first threshold value in the third wire during a third period, the third period being a period of 35% or more and 90% or less of a gait phase of a right leg of the user; causing the at least one motor to generate a tension greater than or equal to the first threshold value in the fourth wire during a fourth period, the fourth period being a period of 0% or more and 25% or less and 65% or more and less than 100% of the gait phase of the right leg; causing the at least one motor to generate a tension less than a second threshold value in the first wire during a fifth period, the fifth period being a period of 0% or more and less than 100% of the gait phase of the left leg, except the first period; causing the at least one motor to generate a tension greater than or equal to the second threshold value in the second wire during a sixth period, the sixth period being a period of 0% or more and less than 100% of the gait phase of the left leg, except the second period; causing the at least one motor to generate a tension less than the second threshold value in the third wire during a seventh period, the seventh period being a period of 0% or more and less than 100% of the gait phase of the right leg, except the third period; causing the at least one motor to generate a tension greater than or equal to the second threshold value in the fourth wire during an eighth period, the eighth period being a period of 0% or more and less than 100% of the gait phase of the right leg, except the fourth period, the first threshold value being larger than the second threshold value; and, when stopping the first assistance, causing the at least one motor to make a tension of the first wire less than the first threshold value during a first stop period, the first stop period being a period starting in a boundary period in the first period and ending in a start period of the second period, and not to generate a tension greater than or equal to the first threshold value in the second wire during the second period; and causing the at least one motor to make a tension of the third wire less than the first threshold value during a second stop period, the second stop period being a period starting in a boundary period in the third period and ending in a start period of the fourth period, and not to generate a tension greater than or equal to the first threshold value in the fourth wire during the fourth period. The boundary period in the first period includes a timing at which the left leg of the user shifts from a stance phase to a swing phase, and the boundary period in the third period includes a timing at which the right leg of the user shifts from the stance phase to the swing phase. The recording medium according to the aspect described above can achieve advantages similar to those of the assistance apparatus according to the aspect of the present disclosure.

It should be noted that the general or specific aspects described above may be implemented as a system, an apparatus, a method, an integrated circuit, a computer program, or a computer-readable recording medium such as a recording disc, or any selective combination thereof. Examples of the computer-readable recording medium include a non-volatile recording medium such as a CD-ROM.

Embodiment

The following specifically describes an assistance apparatus and so on according to an embodiment of the present disclosure with reference to the drawings. The following embodiment describes general or specific examples. Numerical values, shapes, constituent elements, arrangement positions and connection forms of the constituent elements, steps, the order of the steps, and so on in the following embodiment are merely examples and are not intended to limit the present disclosure. The constituent elements mentioned in the following embodiment are described as optional constituent elements unless they are specified in independent claims that define the present disclosure in its broadest concept. The following description of the embodiment may include expressions with the term "approximately", such as approximately parallel or approximately perpendicular. For example, the expression "approximately parallel" is used to mean not only the state of being exactly parallel but also the state of being substantially parallel, that is, the state of being parallel with an error of several percent, for example. This also applies to other expressions with "approximately". In addition, the drawings are illustrative and are not to scale. In the drawings, substantially the same constituent elements are given the same numerals and will not be repeatedly described or will be described in brief.

In this embodiment, an assistance apparatus 100 will be described as an assistance apparatus that assists a user wearing the assistance apparatus 100 in walking. Specifically, the assistance apparatus 100 according to the embodiment will be described as an assistance apparatus that actively supports flexion and extension of the hip joints of the user to allow the user to walk. In this embodiment, the term "actively supporting" may refer not only to supporting flexion and extension forces, which are required for the hip joints, during flexion and extension of the hip joints of the user to walk in the direction of travel but also to applying a force for causing flexion and extension of the hip joints and to physically controlling the amount of flexion and extension of the hip joints to the desired amount of flexion and extension, that is, physically controlling movements of the hip joints of the user. As used herein, the term "assisting the user" by the assistance apparatus 100 is used to include both actively supporting the movement of the user and supporting the movement of the user in an auxiliary manner.

1. Configuration of Assistance Apparatus according to Embodiment

Figure 2:
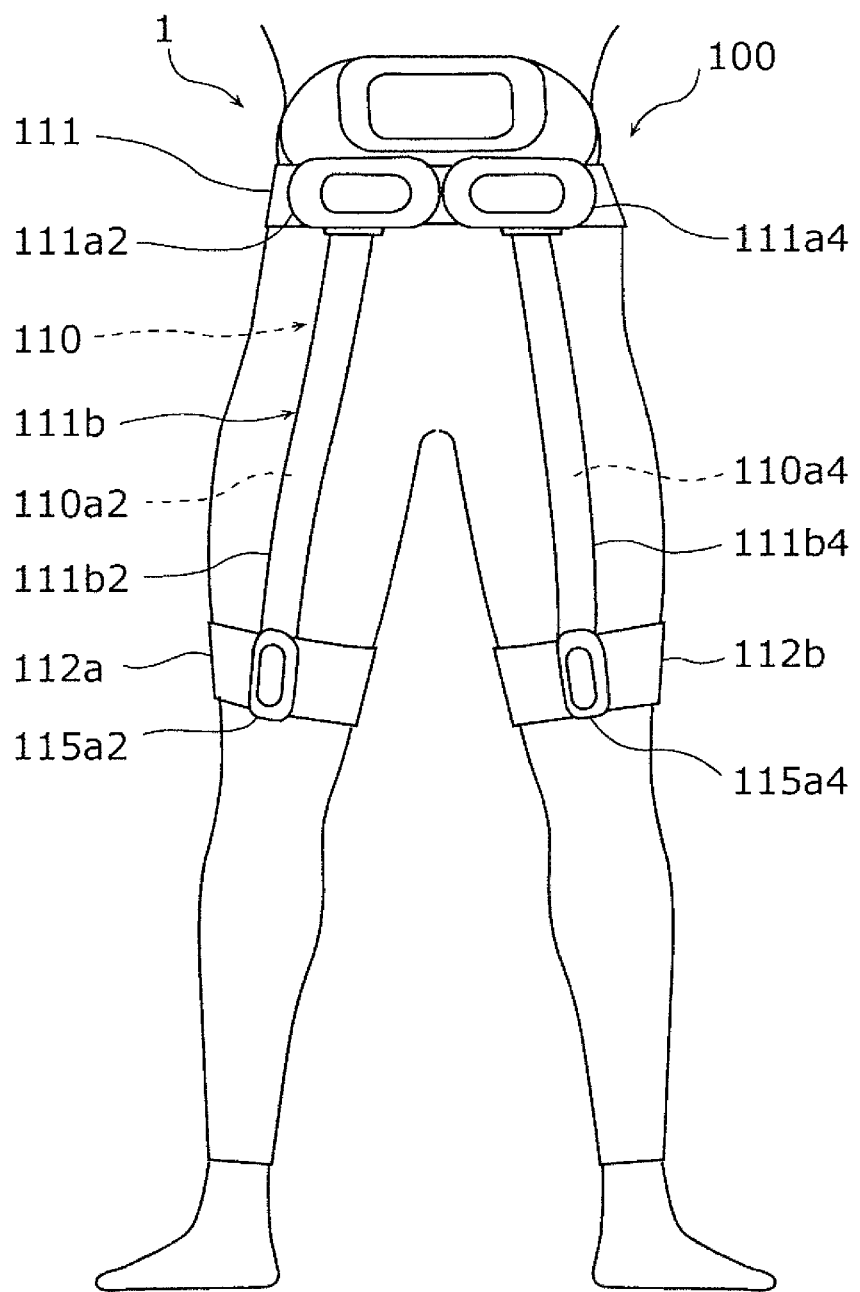
FIG. 2 is a back view of the user wearing the assistance apparatus illustrated in FIG. 1.
Figure 3:
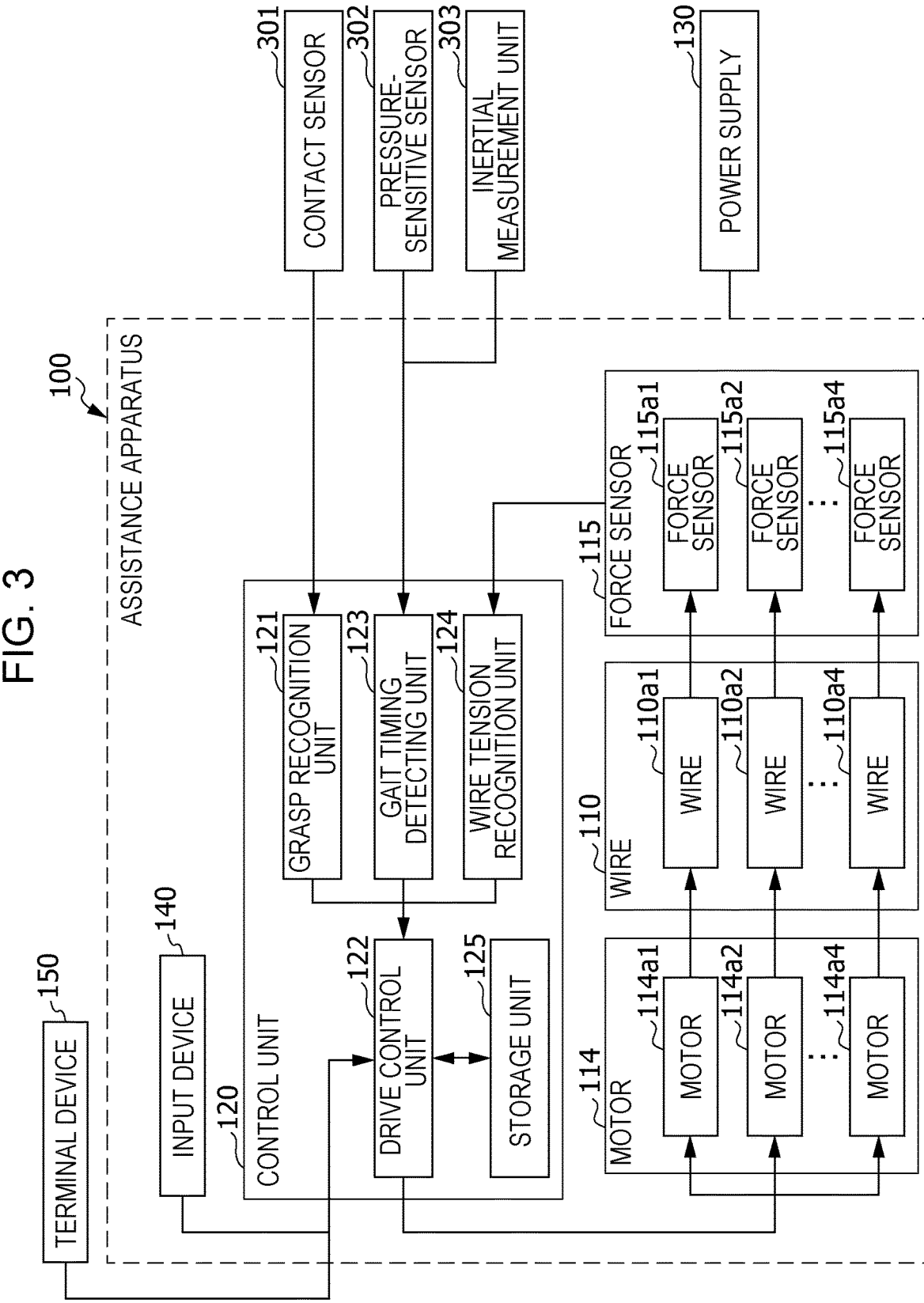
FIG. 3 is a block diagram illustrating a functional configuration of the assistance apparatus according to the embodiment.

The assistance apparatus 100 according to the embodiment will be described with reference to FIG. 1 to FIG. 3. FIG. 1 is a front view of a user 1 wearing the assistance apparatus 100 according to the embodiment, as viewed from the front. FIG. 2 is a back view of the user 1 wearing the assistance apparatus 100 illustrated in FIG. 1. FIG. 3 is a block diagram illustrating a functional configuration of the assistance apparatus 100 according to the embodiment.

As illustrated in FIG. 1 to FIG. 3, the assistance apparatus 100 includes an upper-body belt 111, a left knee belt 112a, a right knee belt 112b, and wires 110. The assistance apparatus 100 further includes motors 114, force sensors 115, and a control unit 120 that controls the operation of the motors 114. The assistance apparatus 100 may include a power supply 130 for supplying electric power to the motors 114 and so on. The power supply 130 may be, for example, a primary battery, a secondary battery, or the like.

The wires 110 include wires 110a1 to 110a4. Each of the wires 110 is coupled to the upper-body belt 111 and the left knee belt 112a or coupled to the upper-body belt 111 and the right knee belt 112b.

The motors 114 include motors 114a1 to 114a4. The wire 110a1 is coupled to the motor 114a1. The wire 110a2 is coupled to the motor 114a2. The wire 110a3 is coupled to the motor 114a3. The wire 110a4 is coupled to the motor 114a4.

The force sensors 115 include force sensors 115a1 to 115a4. The force sensor 115a1 is disposed on the wire 110a1. The force sensor 115a2 is disposed on the wire 110a2. The force sensor 115a3 is disposed on the wire 110a3. The force sensor 115a4 is disposed on the wire 110a4.

The upper-body belt 111 is worn on the upper half of the body of the user 1. The upper-body belt 111 has a band shape, for example. The upper-body belt 111 includes, near an end portion thereof, a fixing member. Examples of the fixing member include a hook-and-loop fastener such as a Velcro (registered trademark) tape, a fastener such as a hook or a buckle, and a tape. For example, the upper-body belt 111 is wrapped around the waist of the user 1 and is kept wrapped around the waist of the user 1 by using the fixing member. Thus, the upper-body belt 111 is worn on the waist of the user 1. The fixing position of the fixing member is adjusted to change the inner diameter of the wrapped upper-body belt 111. Since the length of the upper-body belt 111 can be adjusted, various users 1 with different waist circumferences can wear the upper-body belt 111. The upper-body belt 111 is made of a non-extensible material, for example. Thus, the upper-body belt 111 is less deformable when pulled by the wires 110. The term "upper half of the body", as used herein, is used to include a portion of the body of the user from the shoulder to the waist. The upper-body belt 111 illustrated in FIG. 1 and FIG. 2 has a configuration of a waist belt to be worn on the waist of the user 1. The upper-body belt 111 may be worn on, for example, the waist of the user 1 and/or the shoulder of the user 1 and/or the chest of the user 1.

The upper-body belt 111 may have a tubular shape. In this case, the tubular-shaped upper-body belt 111 may have a larger circumference than the waist circumference of the user 1. The upper-body belt 111 has an adjustment mechanism for adjusting the length of the upper-body belt 111 so that the upper-body belt 111 fits the waist of the user 1. The adjustment mechanism is, for example, a hook-and-loop fastener and may be configured such that a portion of the hook-and-loop fastener having a hook surface is located on an outer periphery of the tubular shape in such a manner as to branch from the outer periphery and a loop surface of the hook-and-loop fastener is located on an outer peripheral surface of the tubular shape. That is, the upper-body belt 111 folds back at the portion of the hook-and-loop fastener, and the inner diameter of the tube formed by the upper-body belt 111 changes in accordance with the amount of fold-back.

The left knee belt 112a is worn on the left leg of the user 1 in the vicinity of the left knee, and the right knee belt 112b is worn on the right leg of the user 1 in the vicinity of the right knee. The left knee belt 112a may be worn on any portion of the left leg in a region extending from below the knee to the thigh. The right knee belt 112b may be worn on any portion of the right leg in a region extending from below the knee to the thigh. That is, the term "knee", as used herein, may be used to include a region extending from below the knee to the thigh.

Each of the knee belts 112a and 112b has a band shape, for example, and includes, near an end portion thereof, a fixing member. The knee belts 112a and 112b are the knee left belt 112a and the right knee belt 112b. Examples of the fixing member include a hook-and-loop fastener such as a Velcro (registered trademark) tape, a fastener such as a hook or a buckle, and a tape. Each of the knee belts 112a and 112b is worn on a corresponding one of the thighs of the user 1 or above a corresponding one of the knees of the user 1. For example, each of the knee belts 112a and 112b is wrapped around the corresponding one of the thighs or the like of the user 1 and is kept wrapped around the corresponding one of the thighs or the like of the user 1 by using the fixing member. Thus, the knee belts 112a and 112b are worn on the thighs or the like of the user 1. The fixing positions of the fixing members are adjusted to change the respective inner diameters of the wrapped knee belts 112a and 112b. Since the lengths of the knee belts 112a and 112b can be adjusted, various users 1 having different leg circumferences can wear the knee belts 112a and 112b. The knee belts 112a and 112b may not necessarily be worn over the knee joints. The human thigh has a feature in that the diameter of the thigh becomes larger gradually from the knee toward the hip. Thus, the knee belts 112a and 112b, which are worn on the thighs, namely, above the knees, slip just a little even under tensile forces of the wires 110 when the knee belts 112a and 112b are tightly fastened. In addition, the knee belts 112a and 112b are made of a non-extensible material, for example. Thus, the knee belts 112a and 112b are less deformable when pulled by the wires 110.

Each of the knee belts 112a and 112b may have a tubular shape. In this case, the tubular-shaped knee belts 112a and 112b may have larger circumferences than the thighs of the user 1. The knee belts 112a and 112b have each an adjustment mechanism for adjusting the length of the corresponding one of the knee belts 112a and 112b so that the knee belts 112a and 112b fit the thighs or the like of the user 1. Each of the adjustment mechanisms is, for example, a hook-and-loop fastener and may be configured such that a portion of the hook-and-loop fastener having a hook surface is located on an outer periphery of the tubular shape in such a manner as to branch from the outer periphery and a loop surface of the hook-and-loop fastener is located on an outer peripheral surface of the tubular shape. That is, the knee belts 112a and 112b each fold back at the portion of the hook-and-loop fastener, and the inner diameter of the tube formed by each of the knee belts 112a and 112b changes in accordance with the amount of fold-back.

The motors 114 are arranged on the upper-body belt 111 in a fixed manner. In this embodiment, the motors 114 include four motors 114a1 to 114a4. For example, the motors 114a1 to 114a4 may be accommodated in hollow containers 111a1 to 111a4 included in the upper-body belt 111, respectively. The containers 111a1 to 111a4 may be integrated with the upper-body belt 111 or may be removably attached to the upper-body belt 111. The containers 111a1 to 111a4 may be disposed in the manner illustrated in FIG. 1 and FIG. 2. In the example illustrated in FIG. 1 and FIG. 2, the containers 111a1, 111a2, 111a3, and 111a4 are located on the left side of the front part, the left side of the back part, the right side of the front part, and the right side of the back part of the body of the user 1, respectively. The motors 114a1, 114a2, 114a3, and 114a4 are accommodated in the containers 111 a1, 111a2, 111a3, and 111a4, respectively. The motor 114a1 changes the length of the wire 110a1 between the upper-body belt 111 and the left knee belt 112a to adjust the tension of the wire 110a1. The motor 114a2 changes the length of the wire 110a2 between the upper-body belt 111 and the left knee belt 112a to adjust the tension of the wire 110a2. The motor 114a3 changes the length of the wire 110a3 between the upper-body belt 111 and the right knee belt 112b to adjust the tension of the wire 110a3. The motor 114a4 changes the length of the wire 110a4 between the upper-body belt 111 and the right knee belt 112b to adjust the tension of the wire 110a4.

In this embodiment, each of the motors 114a1 to 114a4 includes a pulley, a drive shaft for rotating the pulley, and an electric motor for driving the drive shaft to rotate. The pulley of each of the motors 114a1 to 114a4 has a corresponding wire among the wires 110a1 to 110a4 wound therearound. The motors 114a1 to 114a4 and the wires 110a1 to 110a4 have a one-to-one correspondence. The respective pulleys, drive shafts, and electric motors of the motors 114a1 to 114a4 are accommodated in the containers 111a1 to 111a4, respectively. Each of the motors 114a1 to 114a4 may include an electric motor, but may include no pulley or drive shaft. Alternatively, the upper-body belt 111 may include pulleys and drive shafts, each pulley and drive shaft being associated with one of the motors 114a1 to 114a4. In this case, a rotating shaft of the electric motor is coupled to the drive shaft for the pulley in such a manner that a rotational driving force can be transmitted to the drive shaft. Instead of the motors 114a1 to 114a4, for example, a device capable of adjusting the lengths of the wires 110a1 and 110a2 between the upper-body belt 111 and the left knee belt 112a and the lengths of the wires 110a3 and 110a4 between the upper-body belt 111 and the right knee belt 112b, such as a linear actuator or a pneumatic or hydraulic piston, may be used. In the assistance apparatus 100 having the configuration described above, the wound portions of the wires 110a1 to 110a4 and the motors 114a1 to 114a4 are located on the upper-body belt 111, and the wires 110a1 to 110a4 and the knee belts 112a and 112b are located below the upper-body belt 111. Accordingly, the assistance apparatus 100 achieves a simple and compact configuration.

In this embodiment, the wires 110 include four wires 110a1 to 110a4. The motor 114a1 is coupled to the wire 110a1, the motor 114a2 is coupled to the wire 110a2, the motor 114a3 is coupled to the wire 110a3, and the motor 114a4 is coupled to the wire 110a4 so as to individually adjust the lengths of the wires 110a1 to 110a4.

Each of the wires 110a1 and 110a2 has one end fixed to the left knee belt 112a. The wire 110a1 has another end coupled to the motor 114a1, and the wire 110a2 has another end coupled to the motor 114a2. That is, the other end of the wire 110a1 and the other end of the wire 110a2 are fixed. The wire 110a1 couples the left knee belt 112a and the motor 114a1 to each other, and the wire 110a2 couples the left knee belt 112a and the motor 114a2 to each other.

Each of the wires 110a3 and 110a4 has one end fixed to the right knee belt 112b. The wire 110a3 has another end coupled to the motor 114a3, and the wire 110a4 has another end coupled to the motor 114a4. That is, the other end of the wire 110a3 and the other end of the wire 110a4 are fixed. The wire 110a3 couples the right knee belt 112b and the motor 114a3 to each other, and the wire 110a4 couples the right knee belt 112b and the motor 114a4 to each other.

In this embodiment, each of the motors 114a1 to 114a4 rotates the pulley in the forward or reverse direction to wind or unwind the corresponding wire among the wires 110a1 to the 110a4 around the pulley. The wires 110a1 to 110a4 described above are fixed to the waist of the user 1 by the upper-body belt 111 and are fixed to the left and right thighs or the like of the user 1 by the knee belts 112a and 112b.

As described above, each of the wires 110a1 to 110a4 couples the upper-body belt 111 to the left knee belt 112a or the right knee belt 112b. The wires 110a1 to 110a4 may be coupled to the upper-body belt 111 directly or indirectly. Each of the wires 110a1 to 110a4 may be coupled to the left knee belt 112a or the right knee belt 112b directly or indirectly. In the example described above, the one end of each of the wires 110a1 to 110a4 is fixed to, or is directly coupled to, the left knee belt 112a or the right knee belt 112b, and the other end of each of the wires 110a1 to 110a4 is fixed to, or is indirectly coupled to, the upper-body belt 111 via the corresponding one of the motors 114. However, each of the wires 110 may be coupled to the upper-body belt 111 and each of the wires 110 may be coupled to the left knee belt 112a or the right knee belt 112b by using the following configuration, for example.

Specifically, the one end of each of the wires 110 may be indirectly coupled to the left knee belt 112a or the right knee belt 112b via the corresponding one of the motors 114, and the other end of each of the wires 110 may be directly coupled to the upper-body belt 111. Alternatively, both ends of each of the wires 110 may be directly coupled to the upper-body belt 111 and to the left knee belt 112a or the right knee belt 112b, and a motor, a linear actuator, or a pneumatic or hydraulic piston may be disposed in the middle of each of the wires 110 to adjust the length of the wire 110.

Alternatively, the one end of each of the wires 110 may be directly coupled to the left knee belt 112a or the right knee belt 112b, and the other end of each of the wires 110 may be indirectly coupled to the left knee belt 112a or the right knee belt 112b via the corresponding one of the motors 114 in such a manner that each of the wires 110 is arranged to reciprocate between the left knee belt 112a or the right knee belt 112b and the upper-body belt 111. Alternatively, the one end of each of the wires 110 may be directly coupled to the upper-body belt 111, and the other end of each of the wires 110 may be indirectly coupled to the upper-body belt 111 via the corresponding one of the motors 114 in such a manner that each of the wires 110 is arranged to reciprocate between the upper-body belt 111 and the left knee belt 112a or the right knee belt 112b.

Alternatively, both ends of each of the wires 110 may be coupled to the corresponding one of the motors 114 and may be arranged to form a ring through the motor 114. In this case, each of the wires 110 is arranged to reciprocate between the upper-body belt 111 and the left knee belt 112a or the right knee belt 112b, and each of the motors 114 changes the length of the circumference of the ring of the corresponding one of the wires 110.

In any of the configurations described above, each of the wires 110 is coupled to the upper-body belt 111 and the left knee belt 112a or the right knee belt 112b so that the tension thereof is supported by the upper-body belt 111 and the left knee belt 112a or the right knee belt 112b. Thus, when each of the motors 114a1 to 114a4 pulls the corresponding wire among the wires 110, tension that causes the upper-body belt 111 and the left knee belt 112a or the right knee belt 112b to come into close proximity to each other is generated in the corresponding wire.

The force sensors 115 include four force sensors 115a1 to 115a4. The force sensor 115a1 detects the tension of the wire 110a1 and outputs the detected tension to the control unit 120. The force sensor 115a2 detects the tension of the wire 110a2 and outputs the detected tension to the control unit 120. The force sensor 115a3 detects the tension of the wire 110a3 and outputs the detected tension to the control unit 120. The force sensor 115a4 detects the tension of the wire 110a4 and outputs the detected tension to the control unit 120. The force sensor 115a1 is disposed on the wire 110a1 in the left knee belt 112a. The force sensor 115a2 is disposed on the wire 110a2 in the left knee belt 112a. The force sensor 115a3 is disposed on the wire 110a3 in the right knee belt 112b. The force sensor 115a4 is disposed on the wire 110a4 in the right knee belt 112b. The force sensors 115a1 to 115a4 may be located in the upper-body belt 111. Each of the force sensors 115a1 to 115a4 may be capable of detecting the tension of the corresponding wire among the wires 110a1 to 110a4, and may be a strain gauge force sensor or a piezoelectric force sensor, for example. The force sensors 115a1 to 115a4 and the wires 110a1 to 110a4 have a one-to-one correspondence.

Each of the wires 110a1 to 110a4 may be a metallic wire or a non-metallic wire. Examples of the non-metallic wire include a fiber wire and a fiber belt. A fiber wire or fiber belt is made of a material such as polyester fiber, nylon fiber, acrylic fiber, para-aramid fiber, ultrahigh molecular weight polyethylene fiber, poly-p-phenylenebenzobisoxazole (PBO) fiber, polyarylate fiber, or carbon fiber. In this embodiment, four coupling belts 111b1 to 111b4 are arranged along the wires 110a1 to 110a4, respectively, and each of the coupling belts 111b1 to 111b4 extends from the upper-body belt 111 to the left knee belt 112a or the right knee belt 112b. The coupling belts 111b1 to 111b4 and the wires 110a1 to 110a4 have a one-to-one correspondence. As a non-limiting example, the coupling belts 111b1 to 111b4 are each integrated with the upper-body belt 111 and the left knee belt 112a or the right knee belt 112b and are made of a material similar to that of the belts 111, 112a, and 112b. For example, the upper-body belt 111, the knee belts 112a and 112b, and the coupling belts 111b1 to 111b4 may form a single suit having an assistance function that is wearable by the user 1. Each of the coupling belts 111b1 to 111b4 contains and covers the corresponding wire among the wires 110a1 to 110a4. The coupling belts 111b1 to 111b4 may be collectively referred to as coupling belts 111b.

Figure 4:
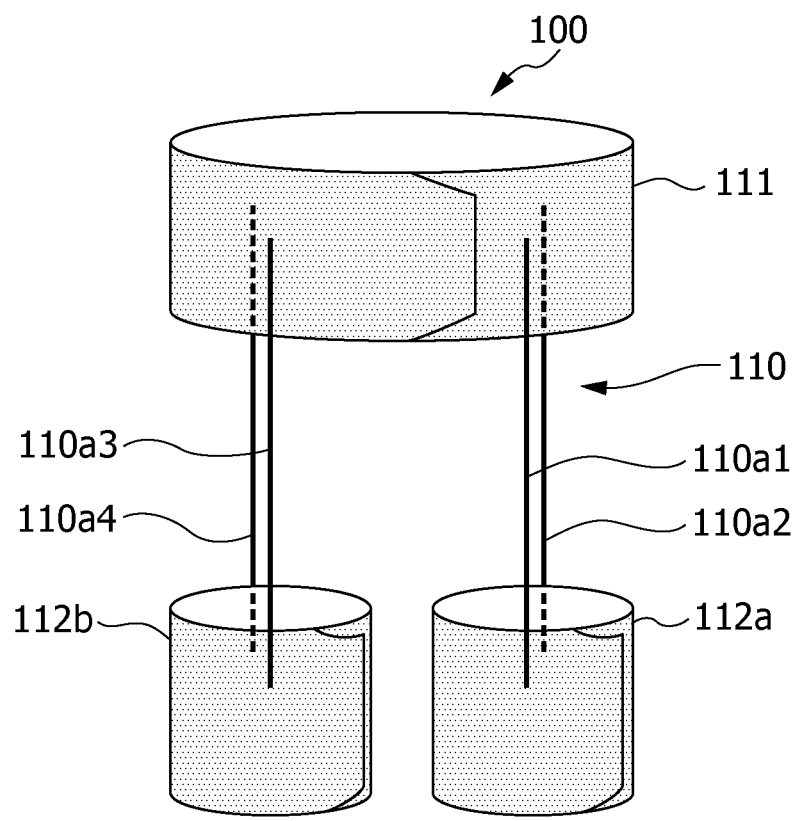
FIG. 4 is a diagram schematically illustrating the arrangement of constituent elements of the assistance apparatus illustrated in FIG. 1.

The arrangement configuration of the wires 110a1 to 110a4 will be described in detail with reference to FIG. 1, FIG. 2, and FIG. 4. FIG. 4 schematically illustrates the arrangement of the constituent elements of the assistance apparatus 100 illustrated in FIG. 1. The wire 110a1 couples the upper-body belt 111 and the left knee belt 112a to each other via the motor 114a1 on or above the front part of the body of the user 1. The wire 110a1 extends upward from the left knee belt 112a on or above the front part of the body of the user 1. The wire 110a2 couples the upper-body belt 111 and the left knee belt 112a to each other via the motor 114a2 on or above the back part of the body of the user 1. The wire 110a2 extends upward from the left knee belt 112a on or above the back part of the body of the user 1. The wire 110a3 couples the upper-body belt 111 and the right knee belt 112b to each other via the motor 114a3 on or above the front part of the body of the user 1. The wire 110a3 extends upward from the right knee belt 112b on or above the front part of the body of the user 1. The wire 110a4 couples the upper-body belt 111 and the right knee belt 112b to each other via the motor 114a4 on or above the back part of the body of the user 1. The wire 110a4 extends upward from the right knee belt 112b on or above the back part of the body of the user 1. In this manner, the wire 110a1 is located on or above the front part of the left leg of the user 1, the wire 110a2 is located on or above the back part of the left leg of the user 1, the wire 110a3 is located on or above the front part of the right leg of the user 1, and the wire 110a4 is located on or above the back part of the right leg of the user 1. The wires 110a1 to 110a4 are pulled individually to apply forces in different directions to the left and right legs.

In the example illustrated in FIG. 1, FIG. 2, and FIG. 4, the wires 110a1 and 110a3 do not cross each other on or above the front part of the body of the user 1. However, the wires 110a1 and 110a3 may cross each other on or above the front part of the body of the user 1. In the example illustrated in FIG. 1, FIG. 2, and FIG. 4, the wires 110a2 and 110a4 do not cross each other on or above the back part of the body of the user 1. However, the wires 110a2 and 110a4 may cross each other on or above the back part of the body of the user 1.

The motors 114a1 to 114a4 pull the wires 110a1 to 110a4 to apply tensions to the wires 110a1 to 110a4, respectively, and the tensions are transmitted to the left and right legs of the user 1 via the upper-body belt 111 and the knee belts 112a and 112b. To effectively transmit the tensions of the wires 110a1 to 110a4 to the left and right legs of the user 1, the upper-body belt 111 and the knee belts 112a and 112b may have rigidity so as not to be deformable and have inflexibility so as not to be extensible. As described above, examples of the material of the upper-body belt 111 and the knee belts 112a and 112b include a non-extensible material. The upper-body belt 111 and the knee belts 112a and 112b described above are worn by the user 1 in such a manner as to tightly fit the body of the user 1, thus efficiently transmitting the driving forces of the motors 114a1 to 114a4 to the legs of the user 1 through the wires 110a1 to 110a4 and effectively assisting movements of the legs of the user 1. The term "assisting", as used herein, is used to include supporting the movement of the user in order to allow the user to perform a predetermined motion and forcing the body of the user to perform the predetermined motion to induce movements of the body.

Figure 5:
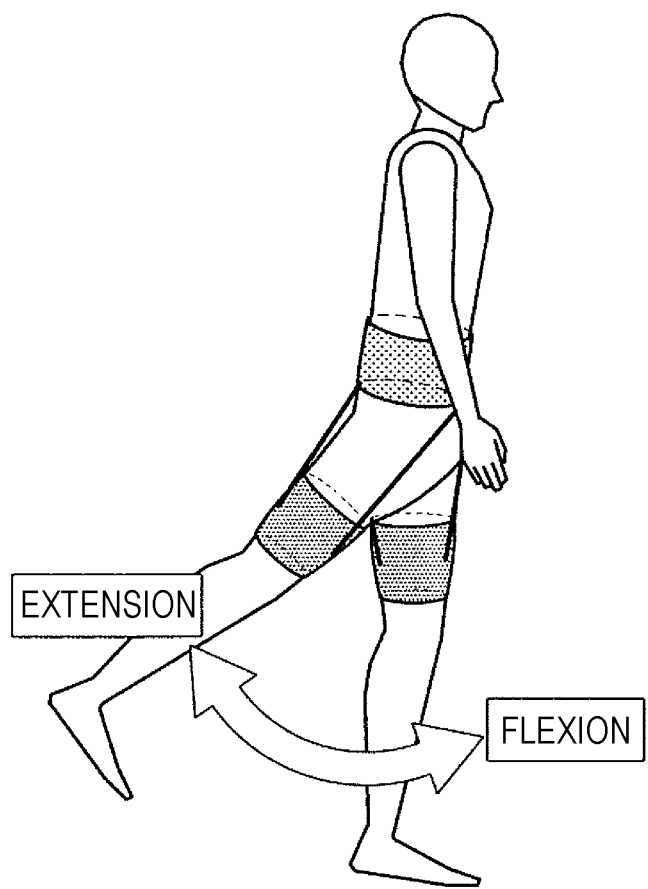
FIG. 5 is a diagram illustrating example motions of the right leg of the user, which are assisted by the assistance apparatus.

A further description will be given of a relationship between tensions applied to the wires 110a1 to 110a4 by the assistance apparatus 100 and motions of the user that are assisted with the tensions. For example, FIG. 5 illustrates example motions of the right leg of the user, which are assisted by the assistance apparatus 100. In the example illustrated in FIG. 5, the assistance apparatus 100 applies an assistance force to the right leg during the swing phase of gait. The assistance apparatus 100 may apply an assistance force to the right leg during the stance phase of gait. The assistance apparatus 100 also enables the left leg of the user to perform motions similar to those of the right leg. As illustrated in FIG. 5, the assistance apparatus 100 can apply an assistance force for flexion and extension to the hip joint of the right leg of the user. The flexion of the hip joint is a motion of moving the thigh forward, and the extension of the hip joint is a motion of moving the thigh backward.

Figure 6A:
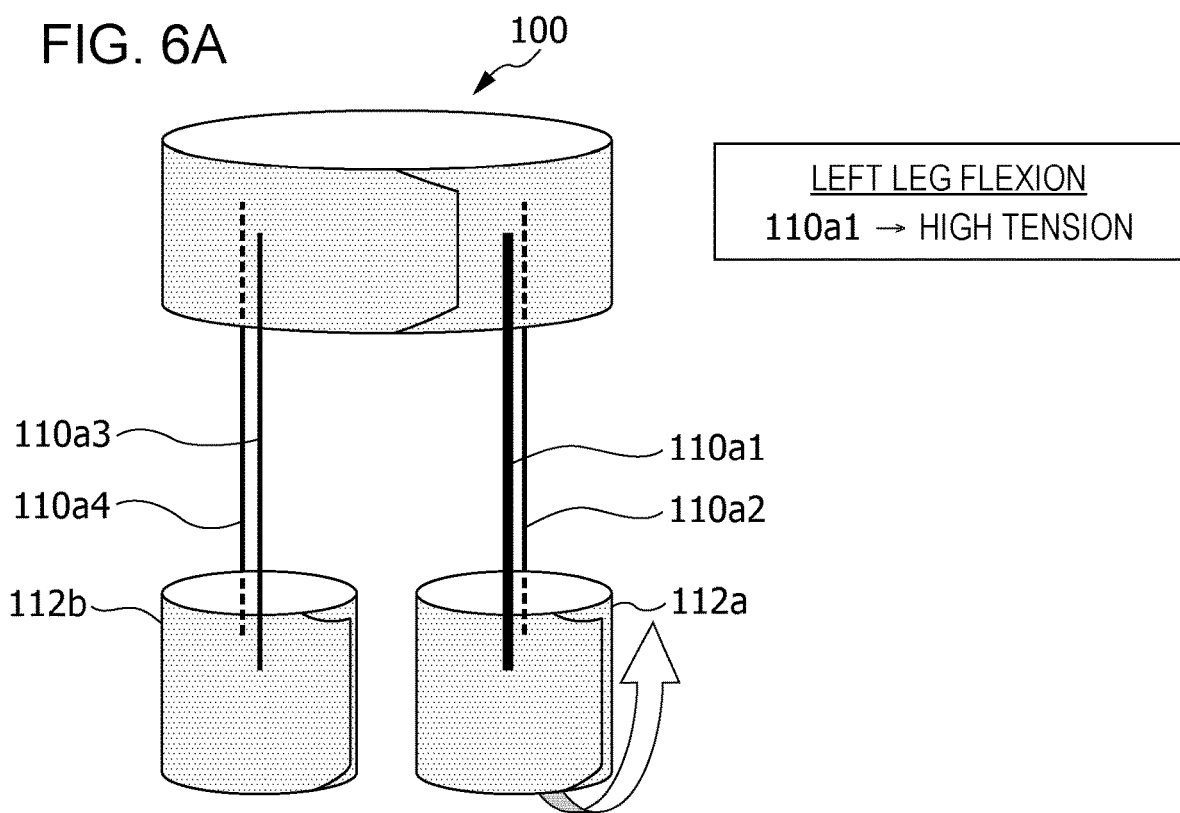
FIG. 6A is a diagram illustrating a case where the assistance apparatus according to the embodiment assists flexion of the hip joint of the left leg of the user.
Figure 6B:
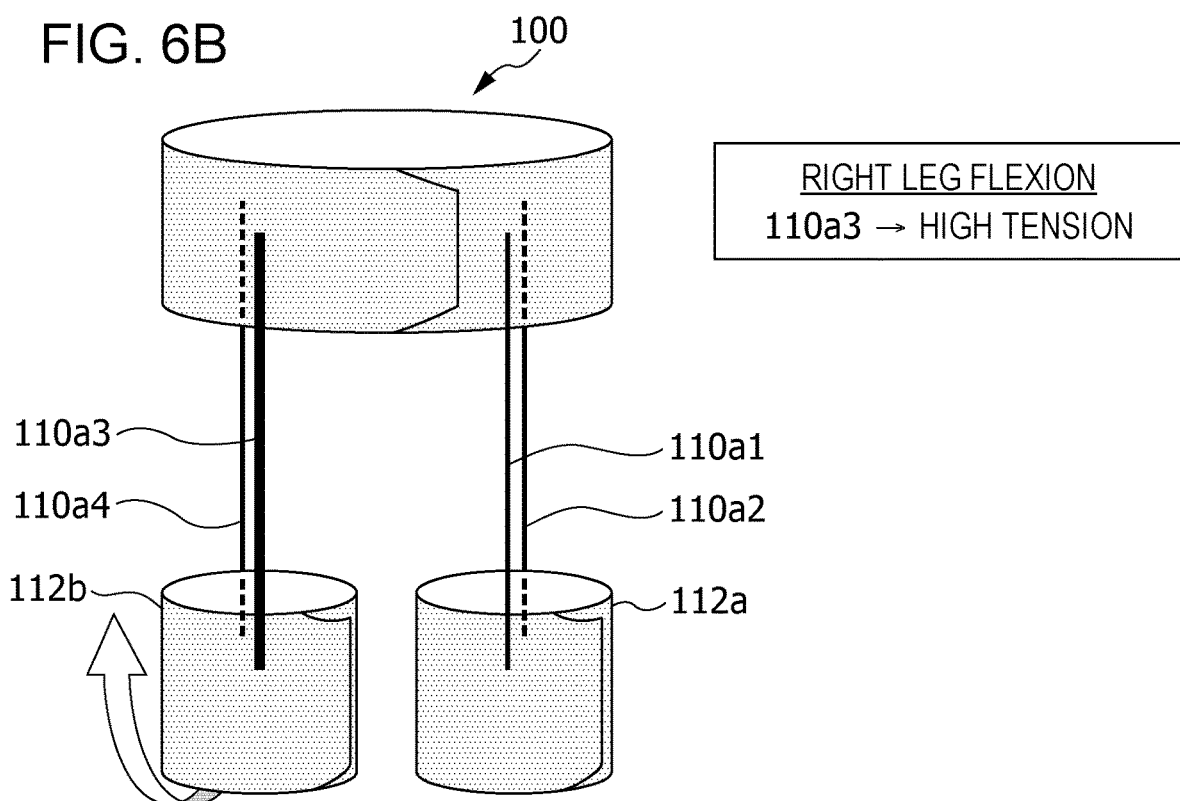
FIG. 6B is a diagram illustrating a case where the assistance apparatus according to the embodiment assists flexion of the hip joint of the right leg of the user.

Further, a relationship between motions of the user, which are induced, or assisted, by the assistance apparatus 100, and assistance forces given to the user through the wires 110a1 to 110a4 will be described with reference to FIG. 6A to FIG. 7B. FIG. 6A illustrates a case where the assistance apparatus 100 according to the embodiment assists flexion of the hip joint of the left leg of the user, and FIG. 6B illustrates a case where the assistance apparatus 100 according to the embodiment assists flexion of the hip joint of the right leg of the user. In FIG. 6A, to flex the left leg, the control unit 120 drives the motor 114a1 to increase the tension of the wire 110a1, that is, to generate a tension in the wire 110a1. In FIG. 6B, to flex the right leg, the control unit 120 drives the motor 114a3 to increase the tension of the wire 110a3. The control unit 120 may control the tensions of the wires 110 in accordance with the detection results of the force sensors 115a1 to 115a4 or in accordance with the amount of driving of the motors 114a1 to 114a4. The details of the control unit 120 will be described below.

In this embodiment, as a non-limiting example, a tension is applied to each of the wires 110a1 to 110a4 in a normal state before flexion. The tension may be applied so as to prevent the corresponding one of the wires 110a1 to 110a4 from loosening and may be less than or equal to 10 N or less than or equal to 5 N, for example. To flex the left leg and the right leg, the tensions of the wires 110a1 and 110a3 are each increased to, for example, a value greater than or equal to 40 N and less than or equal to 100 N. An example for the left leg will be described. A tension greater than or equal to 40 N is exerted on the wire 110a1 for a user, who is a healthy adult male in 20s to 40s. At this time, the user is able to clearly recognize that a force in a flexing direction acts on the left leg and promotes flexion of the left leg. When a tension over 80 N is exerted on the wire 110a1, the left leg of the user is raised in the flexing direction. When the tension exerted on the wire 110a1 is less than or equal to 20 N, the user continues the current motion without substantially perceiving the resistance caused by the tension of the wire 110a1. The tension values described above are examples. The tension values may be changed, as desired, in accordance with the age, gender, body size, or physical activity level of the user, the type of motion of the leg, the degree of assistance on the leg, and so on.

Figure 7A:
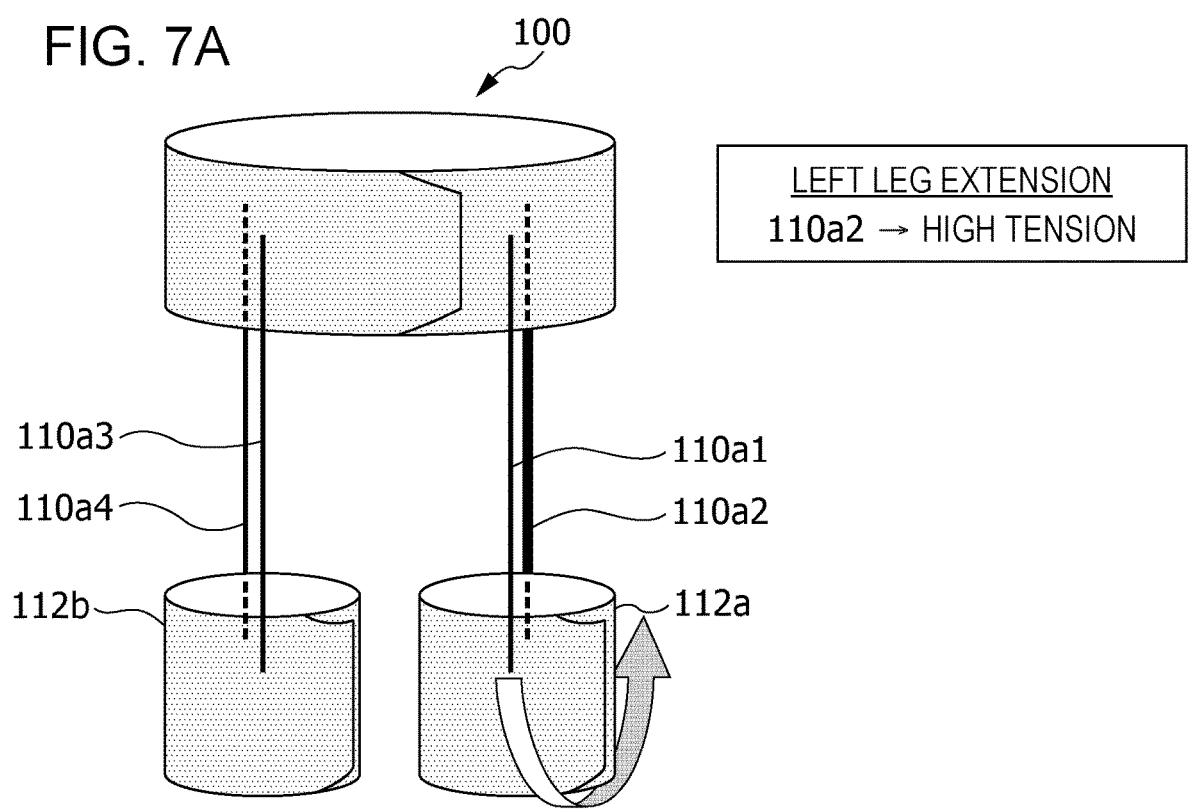
FIG. 7A is a diagram illustrating a case where the assistance apparatus according to the embodiment assists extension of the hip joint of the left leg of the user.
Figure 7B:
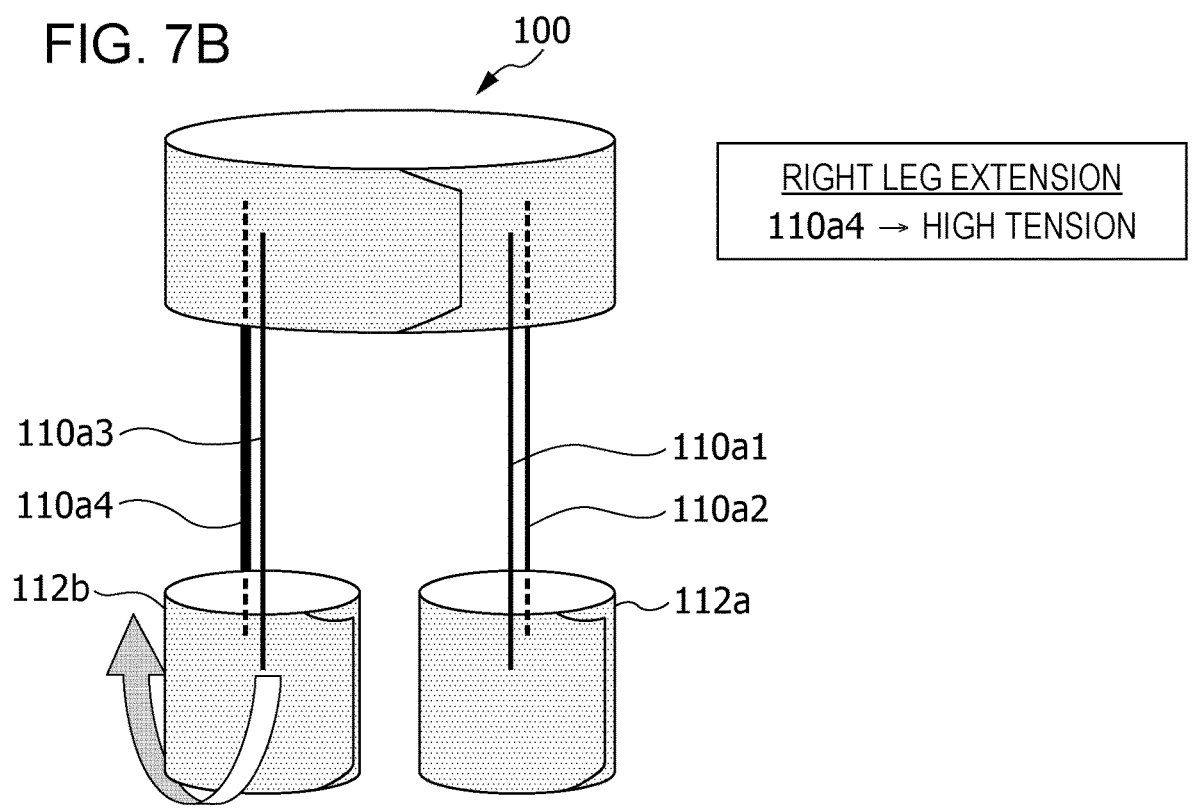
FIG. 7B is a diagram illustrating a case where the assistance apparatus according to the embodiment assists extension of the hip joint of the right leg of the user.

FIG. 7A and FIG. 7B illustrate cases where the assistance apparatus 100 according to the embodiment assists extension of the hip joints of the left and right legs of the user, respectively. In FIG. 7A, the control unit 120 increases the tension of the wire 110a2 to extend the left leg. In FIG. 7B, the control unit 120 increases the tension of the wire 110a4 to extend the right leg. The tensions of the wires 110 during extension may be similar to those during flexion.

In the foregoing description, the control unit 120 increases the tension of one wire to assist one motion of one leg. At this time, the control unit 120 may control the motors corresponding to the other three wires in accordance with the motion of the user so that the tensions of the other three wires are kept in the current states, and adjust the tensions of the other three wires. The control unit 120 may control the motors corresponding to the other three wires so as not to exert tension on the three wires. For example, the control unit 120 may stop the operation of the motors corresponding to the other three wires.

The assistance apparatus 100 described above is capable of assisting the user in walking by applying assistance torques, which are assistance forces in flexing and extending directions, to the user in accordance with torques generated during the stance phase and swing phase of the leg of the user while the user is walking.

Further, the configuration of the control unit 120 of the assistance apparatus 100 will be described with reference to FIG. 3. The control unit 120 controls the overall operation of the assistance apparatus 100. The control unit 120 determines operations to be individually applied to the wires 110a1 to 110a4 and controls assistance for the hip joints of the user 1. The operations to be individually applied to the wires 110a1 to 110a4 are operation patterns of the wires 110a1 to 110a4, including the timings of applying tensions to the wires 110a1 to 110a4, the magnitudes of the tensions, and periods during which the tensions are applied.

The control unit 120 acquires an instruction entered by the user 1 or the like from an input device 140 included in the assistance apparatus 100 or from a terminal device 150 external to the assistance apparatus 100, and controls the assistance apparatus 100 to start and stop assistance in accordance with the acquired instruction. The input device 140 of the assistance apparatus 100 may be a button, a switch, a key, a touch pad, a microphone of an audio recognition device, or any other suitable device. The terminal device 150 may be a terminal device carried by the user 1 wearing the assistance apparatus 100, and examples of the terminal device 150 include a smartphone, a smartwatch, a tablet, and a personal computer. The control unit 120 may communicate with the input device 140 and the terminal device 150 in a wired or wireless way. The wireless communication may be implemented using a wireless local area network (LAN) such as wireless fidelity (Wi-Fi (registered trademark)), or may be short-range wireless communication such as Bluetooth (registered trademark) or ZigBee (registered trademark), or any other type of wireless communication. The wired communication may be any existing wired communication. The control unit 120 may include a wired or wireless communication circuit. Alternatively, the control unit 120 may perform wired communication or wireless communication via a wired or wireless communication circuit included in the assistance apparatus 100. The input device 140 and the terminal device 150 are examples of an interface device.

Figure 8:
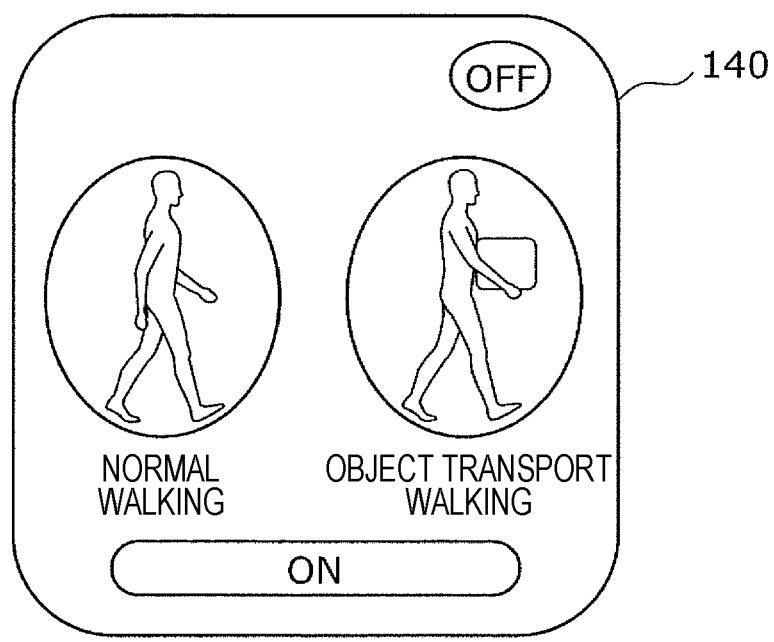
FIG. 8 is a diagram illustrating an example of an input section of an input device included in the assistance apparatus according to the embodiment.

For example, FIG. 8 illustrates an example input section of the input device 140 included in the assistance apparatus 100 according to the embodiment. The input device 140 includes four physical buttons that accept input. The four buttons include an "ON" button for starting the assistance apparatus 100, an "OFF" button for stopping the operation of the assistance apparatus 100, a "normal walking" button for selecting a normal walking mode among operation modes of the assistance apparatus 100, and an "object transport walking" button for selecting an object transport walking mode among the operation modes of the assistance apparatus 100. When the input section of the input device 140 is implemented as a touch panel, the buttons may be icons. In this embodiment, the input device 140 is disposed on the upper-body belt 111, as a non-limiting example. Alternatively, the input device 140 may be disposed on the knee belt 112a or 112b or attached to a part of the body of the user 1, which is away from the upper-body belt 111. The terminal device 150, which is external to the assistance apparatus 100, may have a button configuration similar to that of the input device 140 or an icon configuration on a screen.

Figure 9:
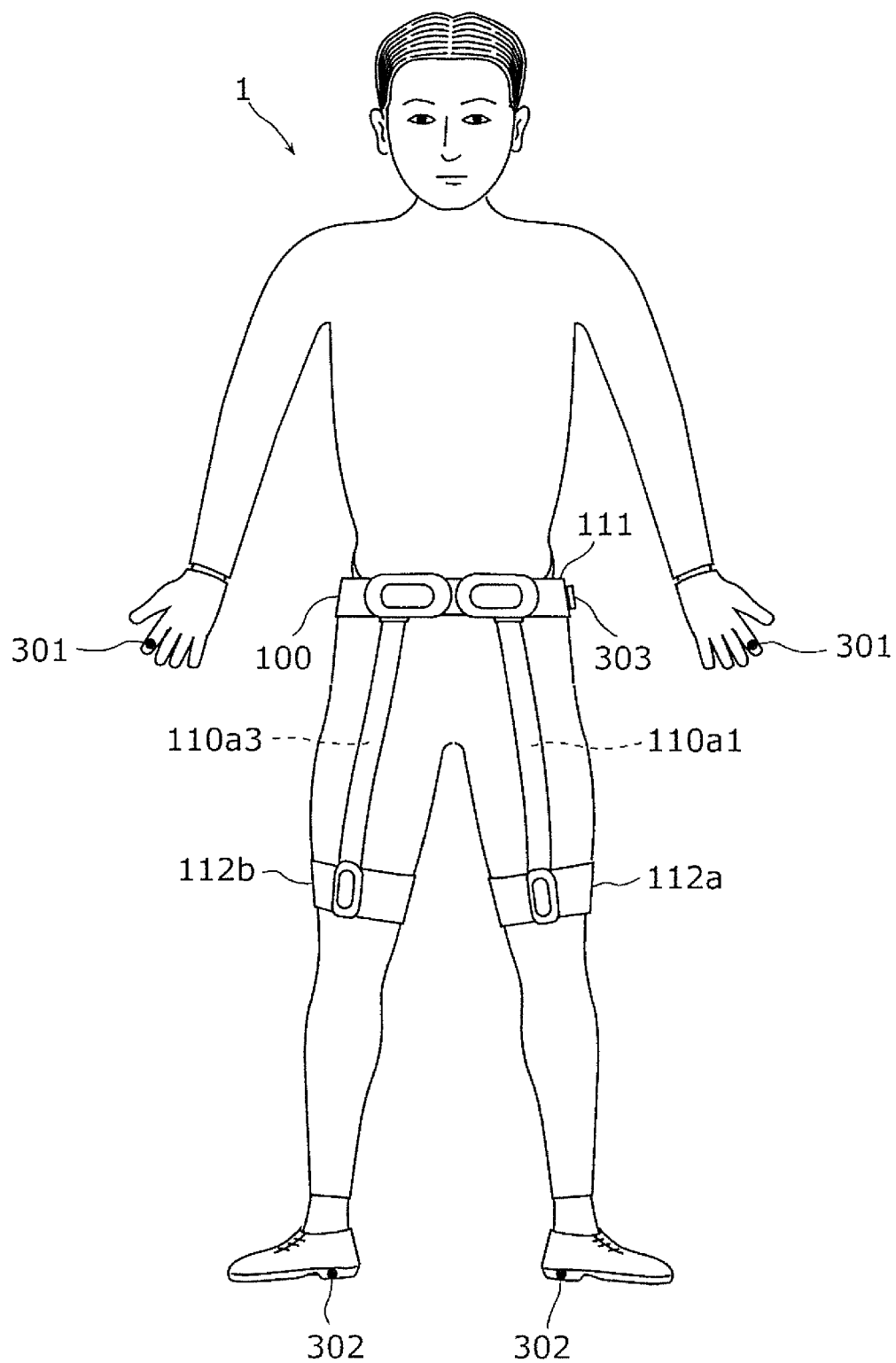
FIG. 9 is a diagram illustrating the arrangement of sensors and so on that are attached to the body of the user.

In this embodiment, furthermore, as illustrated in FIG. 9, a contact sensor 301 and at least one of a pressure-sensitive sensor 302 and an inertial measurement unit 303 are attached to the body of the user 1. FIG. 9 illustrates the arrangement of sensors and so on to be attached to the body of the user 1. The contact sensor 301, the pressure-sensitive sensor 302, and the inertial measurement unit 303 output detection results to the control unit 120. The contact sensor 301 is attached to each of the hands of the user 1. Specifically, the contact sensor 301 is attached to a finger tip or the like of gloves worn by the user 1. The contact sensor 301 may be attached to each of both hands of the user 1 or to either hand of the user 1. The contact sensor 301 detects a direct contact and an indirect contact between the hand of the user 1 and an object. Examples of the contact sensor 301 include a contact detection sensor, a touch sensor, a proximity sensor, and a sensor similar to the pressure-sensitive sensor 302. The contact sensor 301 may be attached to each of the arm, chest, abdomen, and so on of the user 1, which may come into contact with an object while the user 1 is carrying the object.

The pressure-sensitive sensor 302 is attached to each of the soles of the feet of the user 1. Specifically, the pressure-sensitive sensor 302 is attached to each of the bottoms or the like of shoes worn by the user 1. The pressure-sensitive sensor 302 may be attached to each of both feet of the user 1 or to either foot of the user 1. The pressure-sensitive sensor 302 detects a pressure acting on each of the soles of the feet of the user 1, that is, a load. Examples of the pressure-sensitive sensor 302 include a capacitive pressure sensor, a piezoelectric pressure sensor, and a strain gauge pressure sensor. The inertial measurement unit 303 is attached to a portion of the body of the user 1 that moves along with the movement of the user 1, such as the waist in the upper half of the body of the user 1. Specifically, the inertial measurement unit 303 is attached to the upper-body belt 111. The inertial measurement unit 303 includes an acceleration sensor and a gyro sensor (also referred to as an "angular velocity sensor"). The inertial measurement unit 303 may include an acceleration sensor, but may include no gyro sensor. The inertial measurement unit 303 may further include a geomagnetic sensor. The inertial measurement unit 303 detects, on the basis of a detected acceleration and angular velocity, the acceleration of the user 1 in each direction, and the movement direction, movement speed, and movement distance of the user 1. The pressure-sensitive sensor 302 and the inertial measurement unit 303 are examples of a sensor that detects a gait cycle of the user 1.

The contact sensor 301, the pressure-sensitive sensor 302, and the inertial measurement unit 303 exchange information with the control unit 120 via wired communication or wireless communication. The wired communication may be any of the wired communication described above, and the wireless communication may be any of the wireless communication described above.

As illustrated in FIG. 3, the control unit 120 includes a grasp recognition unit 121, a drive control unit 122, a gait timing detection unit 123, a wire tension recognition unit 124, and a storage unit 125. The grasp recognition unit 121, the drive control unit 122, the gait timing detection unit 123, and the wire tension recognition unit 124, which are constituent elements of the control unit 120, may be implemented by a computer system including a processor such as a central processing unit (CPU) or a digital signal processor (DSP) and a memory such as a random access memory (RAM) and a read-only memory (ROM). Some or all of the functions of the constituent elements described above may be achieved by the CPU or the DSP executing a program recorded on the ROM by using the RAM as a work memory. Alternatively, some or all of the functions of the constituent elements described above may be achieved by a dedicated hardware circuit such as an electronic circuit or an integrated circuit. The functions of some or all of the constituent elements described above may be implemented by a combination of the software functions described above and a hardware circuit. The program may be provided as an application by communication via a communication network such as the Internet, communication conforming to a mobile communication standard, communication via any other wireless or wired network, broadcasting, or the like. A computer system and/or a hardware circuit constituted by the control unit 120 may be mounted on the upper-body belt 111, accommodated in the containers 111a1 to 111a4 together with the motors 114a1 to 114a4, or embedded in the upper-body belt 111 at a different location from the motors 114a1 to 114a4, for example. The control unit 120 is an example of a control circuit.

The storage unit 125 is capable of storing information, and the stored information is retrievable from the storage unit 125. The storage unit 125 stores computer programs in accordance with which the constituent elements of the control unit 120 execute processes, threshold values described below, input profiles of wire tensions described below, and so on. The storage unit 125 is implemented as a storage device, for example, a semiconductor memory such as a ROM, a RAM, or a flash memory, a hard disk drive, or a solid state drive (SSD). In this embodiment, the storage unit 125 is included in the control unit 120. Alternatively, the storage unit 125 may be disposed separately from the control unit 120. The storage unit 125 is an example of a memory.

Figure 10A:
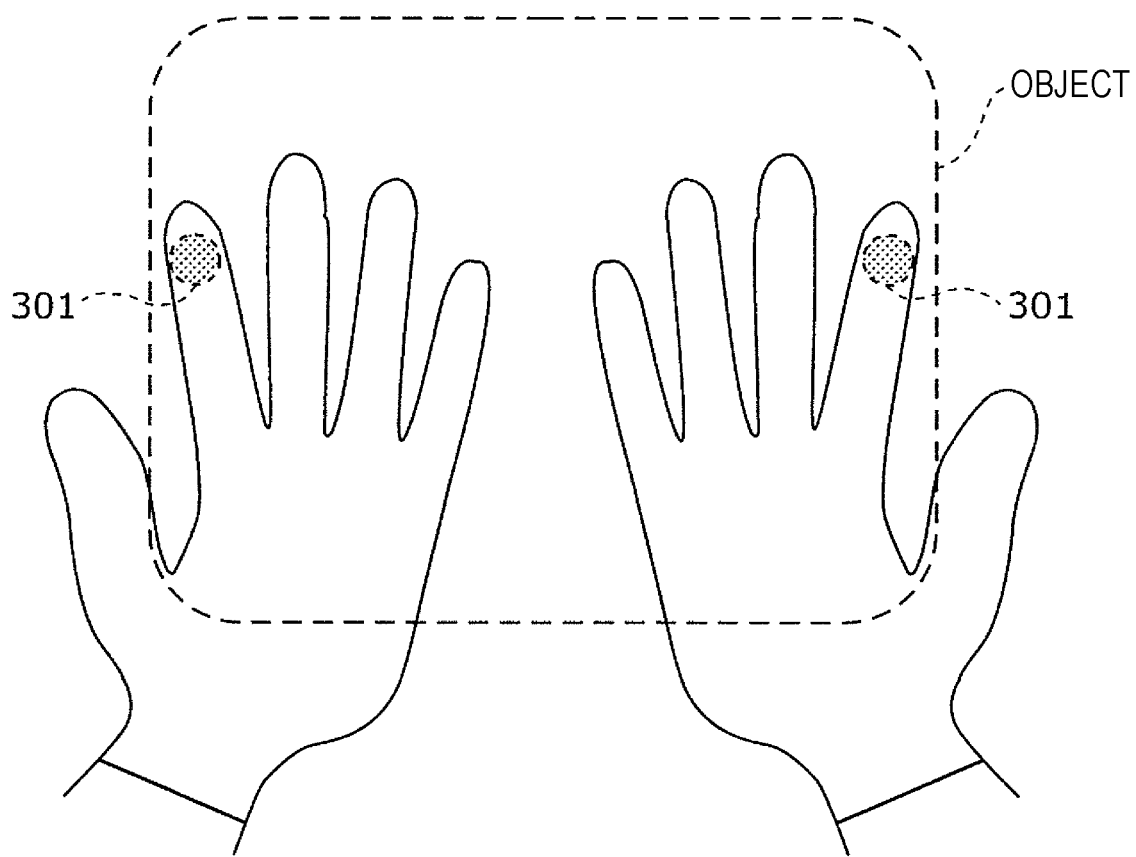
FIG. 10A is a diagram illustrating a relationship between contact sensors and the hands of the user.
Figure 10B:
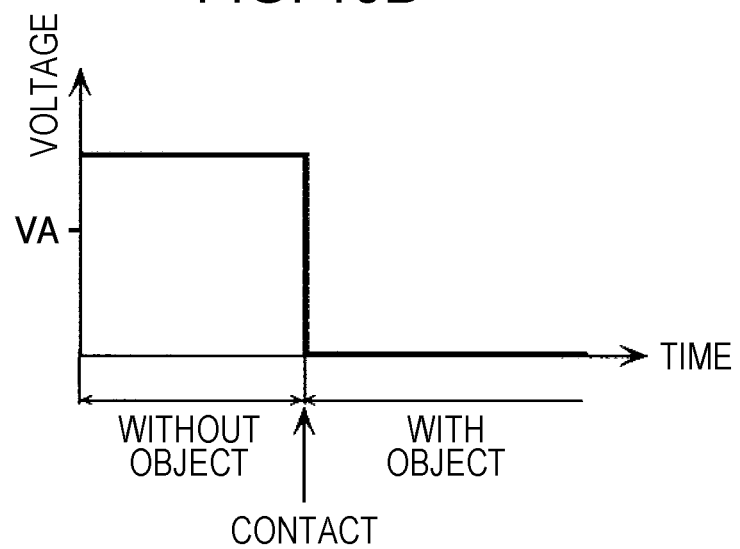
FIG. 10B is a diagram illustrating an example of a signal of a contact sensor.

The grasp recognition unit 121 detects a grasp of an object by the user 1 with their hands. The grasp recognition unit 121 determines whether the user 1 is holding an object with their hands on the basis of a change in sensor value, which is acquired from the contact sensor 301. For example, as illustrated in FIG. 10A and FIG. 10B, the contact sensor 301 is a piezoelectric sensor. In this case, the grasp recognition unit 121 detects a time point at which a voltage value corresponding to a sensor value detected by the contact sensor 301 becomes less than a predetermined value, as a time point at which the hands of the user 1 touch an object, that is, as a time point at which the user 1 grasps the object. For example, in the example illustrated in FIG. 10B, the predetermined value is represented by "VA". FIG. 10A illustrates a relationship between contact sensors 301 and the hands of the user. FIG. 10B illustrates an example of a signal of a contact sensor 301. The grasp recognition unit 121 outputs a detection result to the drive control unit 122.

The gait timing detection unit 123 detects a gait timing to determine a timing of assisting the user 1. The gait timing may include a timing of starting assisting the user 1 during walking, and a timing of determining phases such as a stance phase and a swing phase in a period during which the user 1 takes one step. The drive control unit 122 determines a timing of assisting the user 1 from the gait timing detected by the gait timing detection unit 123 and controls the operation of the motors 114.

Specifically, the gait timing detection unit 123 estimates a gait cycle of the user 1 wearing the assistance apparatus 100, predicts gait phases in the next one step on the basis of the estimation result, and outputs assistance timings based on the predicted gait phases to the drive control unit 122. A gait cycle is a time interval from heel strike of one leg to the next heel strike of the same leg. The gait cycle is constituted by a period of a stance phase and a period of a swing phase. The gait cycle may be sequence of motions occurring from heel strike of one leg to the next heel strike of the same leg.

The gait timing detection unit 123 detects a timing of heel strike of the user 1 on the basis of a sensor value acquired from the pressure-sensitive sensor 302 or on the basis of sensor values acquired from the acceleration sensor and the gyro sensor of the inertial measurement unit 303, and estimates a gait phase for each step, or a gait cycle, of the user 1 in real time. The gait cycles and the steps may be in a one-to-one relationship. Each step of the user 1 is a step with either of the left and right legs. For example, each step of the user 1 corresponds to a period from when the left leg touches the ground to when the left leg touches the ground again. The gait timing detection unit 123 predicts, based on the estimated gait cycle, a gait phase for the next step and a starting time and duration of each of the stance phase and swing phase for the next step, and outputs the prediction results to the drive control unit 122. When the terminal device 150 carried by the user 1 includes an inertial measurement unit, the gait timing detection unit 123 may acquire a sensor value of an acceleration sensor and a sensor value of a gyro sensor from the terminal device 150.

Gait phases represent temporal timings of gait states during a single step taken by the user 1. A time point at which one leg of the user 1 touches the ground corresponds to a time point at which a gait phase is 0%, and a time point at which the same leg of the user 1 touches the ground again corresponds to a time point at which a gait phase is 100%. In a gait phase, timings of gait states of the user 1 are represented in the range of 0% to 100%. For example, a value of 0% to 100% of a gait phase may correspond to the time elapsed from when one leg of the user 1 touches the ground to when the same leg of the user 1 touches the ground again. Specifically, when the time period from when one leg of the user 1 touches the ground to when the same leg of the user 1 touches the ground again is 1 second, the gait phase at the point in time at which a period of 0.5 seconds elapses from the time when the leg of the user 1 touches the ground is represented by 50%.

Figure 11:
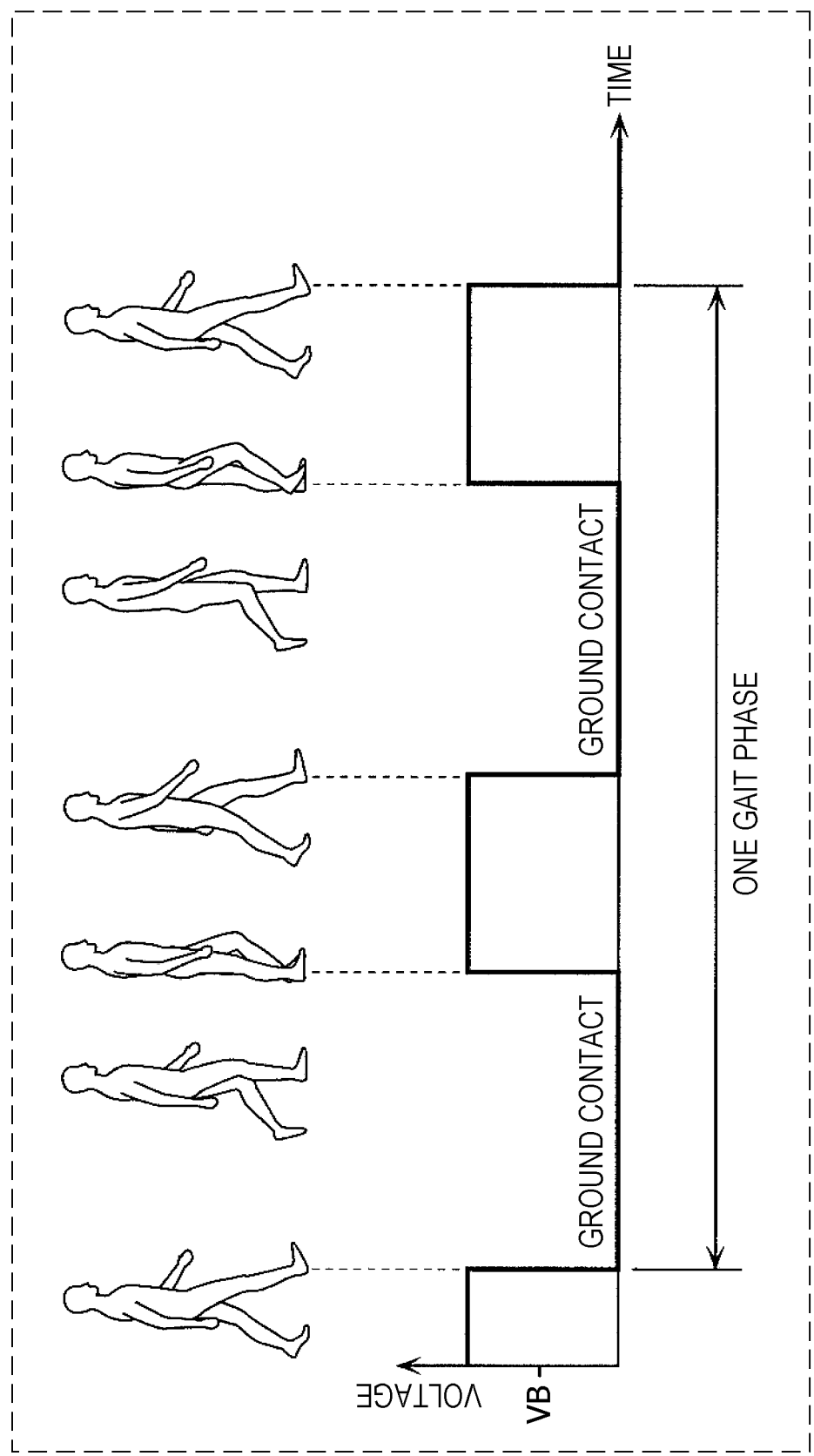
FIG. 11 is a diagram illustrating an example of a signal of a pressure-sensitive sensor.

More specifically, the gait timing detection unit 123 determines a time point at which the leg of the user 1 touches the ground on the basis of the sensor value of the pressure-sensitive sensor 302 in such a manner that, for example, as illustrated in FIG. 11, a time point at which the voltage value corresponding to the pressure sensor value of the pressure-sensitive sensor 302 becomes less than a predetermined value is detected as a timing of heel strike. FIG. 11 illustrates an example of a signal based on signals of the pressure-sensitive sensors 302. For example, the predetermined value is represented by "VB" in FIG. 11. A period during which the pressure-sensitive sensor 302 measures a pressure value greater than or equal to a predetermined value corresponds to a period of heel contact. The pressure-sensitive sensor 302 is placed at each of the feet of the user 1. The gait timing detection unit 123 acquires a timing at which the shoe touches the ground using the pressure-sensitive sensor 302, rather than a timing that is based on the inertial measurement unit 303 located in the upper-body belt 111 or the like. Thus, the gait timing detection unit 123 can more reliably estimate a gait cycle.

Figure 12:
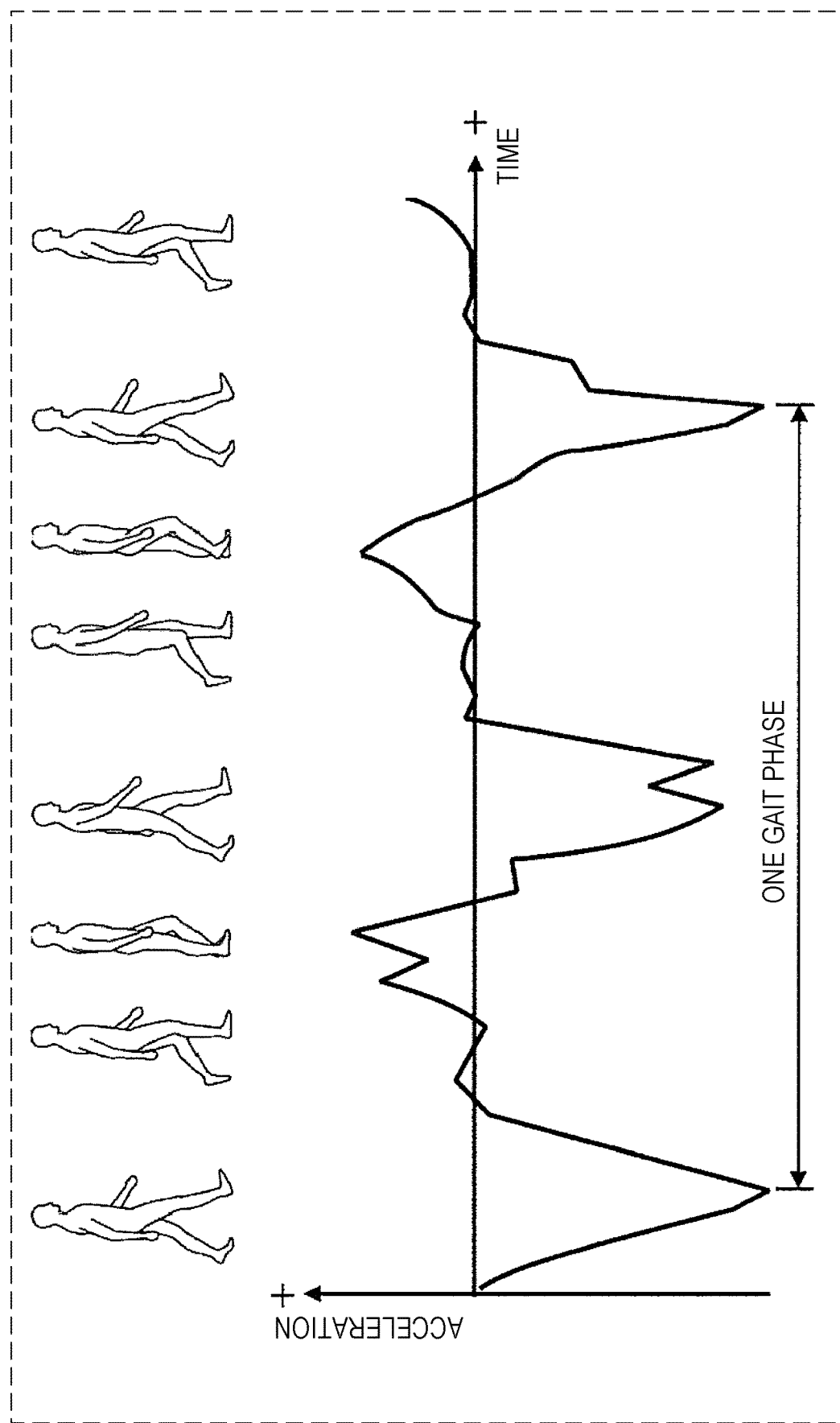
FIG. 12 is a diagram illustrating an example of a signal of an acceleration sensor of an inertial measurement unit.

When the inertial measurement unit 303 is used, the gait timing detection unit 123 determines a time point at which the foot of the user 1 touches the ground on the basis of information obtained by the acceleration sensor. For a method for estimating a time point at which a foot touches the ground by using an acceleration sensor, see, for example, IEEE TRANSACTIONS ON BIOMEDICAL ENGINEERING, VOL. 52, NO. 3, 2005, p. 488, FIG. 1, p. 489, FIG. 2. When estimating a gait cycle on the basis of a sensor value of the inertial measurement unit 303, the gait timing detection unit 123 may estimate a gait cycle by using signal waveforms obtained from the acceleration sensor and the gyro sensor. For example, a gait cycle can be estimated by using a signal waveform obtained from the acceleration sensor, as illustrated in FIG. 12. In the example illustrated in FIG. 12, the signal waveform obtained from the acceleration sensor can be used to estimate a time point at which the foot of the user 1 touches the ground, and a gait cycle can be estimated accordingly. FIG. 12 illustrates an example of a signal of the acceleration sensor of the inertial measurement unit 303.

The user 1 may wear an angle sensor (also referred to as a "tilt sensor"). In this case, the angle sensor is attached to, for example, a thigh of the user 1. The gait timing detection unit 123 acquires the angle of the hip joint of the user 1 as gait information. The gait timing detection unit 123 calculates a gait phase on the basis of a cycle of change in the angle of the hip joint of the user 1.

Regardless of which of the pressure-sensitive sensor 302 and the inertial measurement unit 303 is used, for example, the gait timing detection unit 123 may estimate, based on a sensor value of the pressure-sensitive sensor 302 or a sensor value of the inertial measurement unit 303 for the latest three steps of the user 1, an elapsed time of 0% to 100% of a gait phase for each step and may calculate an average value of the three elapsed times. Then, the gait timing detection unit 123 may predict the point in time corresponding to 100% of the gait phase for the next step on the basis of the average value of the elapsed times. Further, the gait timing detection unit 123 may estimate the start timings of the stance phase and the swing phase during the gait phase for each step on the basis of the signal waveform of the sensor and calculate an average value of the start timings for the three steps. Then, the gait timing detection unit 123 may predict, based on the average value, the start timings of the stance phase and the swing phase for the next one step.

Alternatively, the gait timing detection unit 123 may estimate, based on a sensor value of the pressure-sensitive sensor 302 or a sensor value of the inertial measurement unit 303 for the last one step of the user 1, an elapsed time of 0% to 100% of the gait phase for the one step and may predict the point in time corresponding to 100% of the gait phase for the next step on the basis of the estimated elapsed time. Further, the gait timing detection unit 123 may estimate the start timings of the stance phase and the swing phase during one step on the basis of the sensor values for the last one step of the user 1, and may predict the start timings of the stance phase and the swing phase for the next one step.

The wire tension recognition unit 124 detects the tensions generated in the wires 110a1 to 110a4. The wire tension recognition unit 124 detects the tensions of the wires 110a1 to 110a4 on the basis of sensor values acquired from the force sensors 115a1 to 115a4. The wire tension recognition unit 124 outputs the detected tensions of the wires 110a1 to 110a4 to the drive control unit 122.

The drive control unit 122 controls the motors 114a1 to 114a4, which respectively adjust the tensions of the wires 110a1 to 110a4, on the basis of information on a predicted gait phase of the user 1, which is acquired from the gait timing detection unit 123, and on the basis of information indicating whether the user 1 is carrying an object, which is acquired from the grasp recognition unit 121. The drive control unit 122 starts the motors 114a1 to 114a4, stops the operation of the motors 114a1 to 114a4, and controls the amount by which the wires 110a1 to 110a4 are respectively pulled by the motors 114a1 to 114a4 and the pulling tensions of the wires 110a1 to 110a4. The drive control unit 122 controls the amount of rotation of each of the motors 114a1 to 114a4 and adjusts the rotation torque of each of the motors 114a1 to 114a4, thereby enabling control of the amount by which the corresponding wire among the wires 110 is pulled and the pulling tensions of the corresponding wire.

Specifically, the drive control unit 122 determines a type of assistance to be provided to the user 1 on the basis of the prediction result of the gait timing acquired from the gait timing detection unit 123. Examples of the type of assistance include motions of the leg on which assistance is to be provided to the user 1, such as flexion and extension. In accordance with the type of assistance, the drive control unit 122 further determines a wire to be pulled to assist a motion of the user 1 among the wires 110a1 to 110a4, a tension to be applied to the wire, and a timing of pulling the wire.

Further, the drive control unit 122 changes the relationship between the tension of a wire and the timing of pulling the wire even for the same type of assistance on the basis of information acquired from the grasp recognition unit 121 indicating whether the user 1 is carrying an object.

An assistance correspondence, which is a relationship between the gait timing acquired from the gait timing detection unit 123 and the type of assistance, is set in advance and is stored in, for example, the storage unit 125. A wire-tension relationship, which is a relationship between a wire to be pulled, a tension of the wire, and a timing of pulling the wire, is set in advance in accordance with the type of assistance and information indicating whether the user 1 is carrying an object, and is stored in, for example, the storage unit 125. The wire-tension relationship may be updated on the basis of the achievement of assistance-based control by the assistance apparatus 100. On the basis of information on the assistance correspondence and the wire-tension relationship, which are stored in the storage unit 125, the drive control unit 122 determines a type of assistance to be provided to the user 1 and determines control of wires corresponding to the determined type of assistance. The drive control unit 122 controls the motors linked to the determined wires, in accordance with tensions to be applied to the wires and timings of pulling the wires.

Further, the drive control unit 122 controls the operation of the motors 114a1 to 114a4 on the basis of information on the tensions of the wires 110a1 to 110a4, which is acquired from the wire tension recognition unit 124, so that the tensions of the wires 110a1 to 110a4 have predetermined levels. In addition, the drive control unit 122 may change the wire-tension relationship on the basis of, in addition to the information acquired from the grasp recognition unit 121, the gait timing detection unit 123, and the wire tension recognition unit 124, information on the user 1, such as age, gender, body size, and physical activity level, the degree of assistance on the leg, and so on, and may use the changed wire-tension relationship.

2. Modification of Assistance Apparatus

Figure 13:
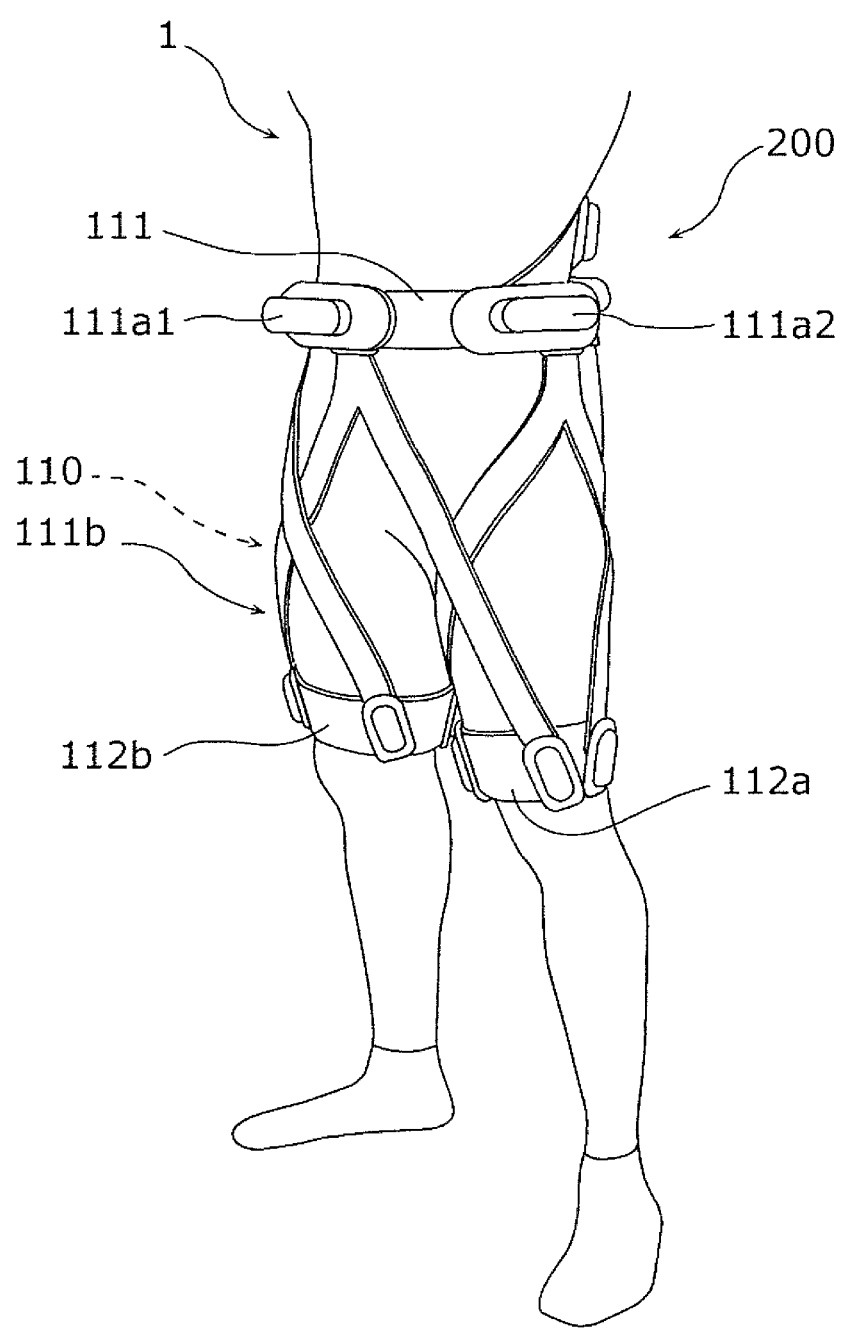
FIG. 13 is a perspective view of a user wearing an assistance apparatus according to a modification of the embodiment, as viewed obliquely from the front.
Figure 14:
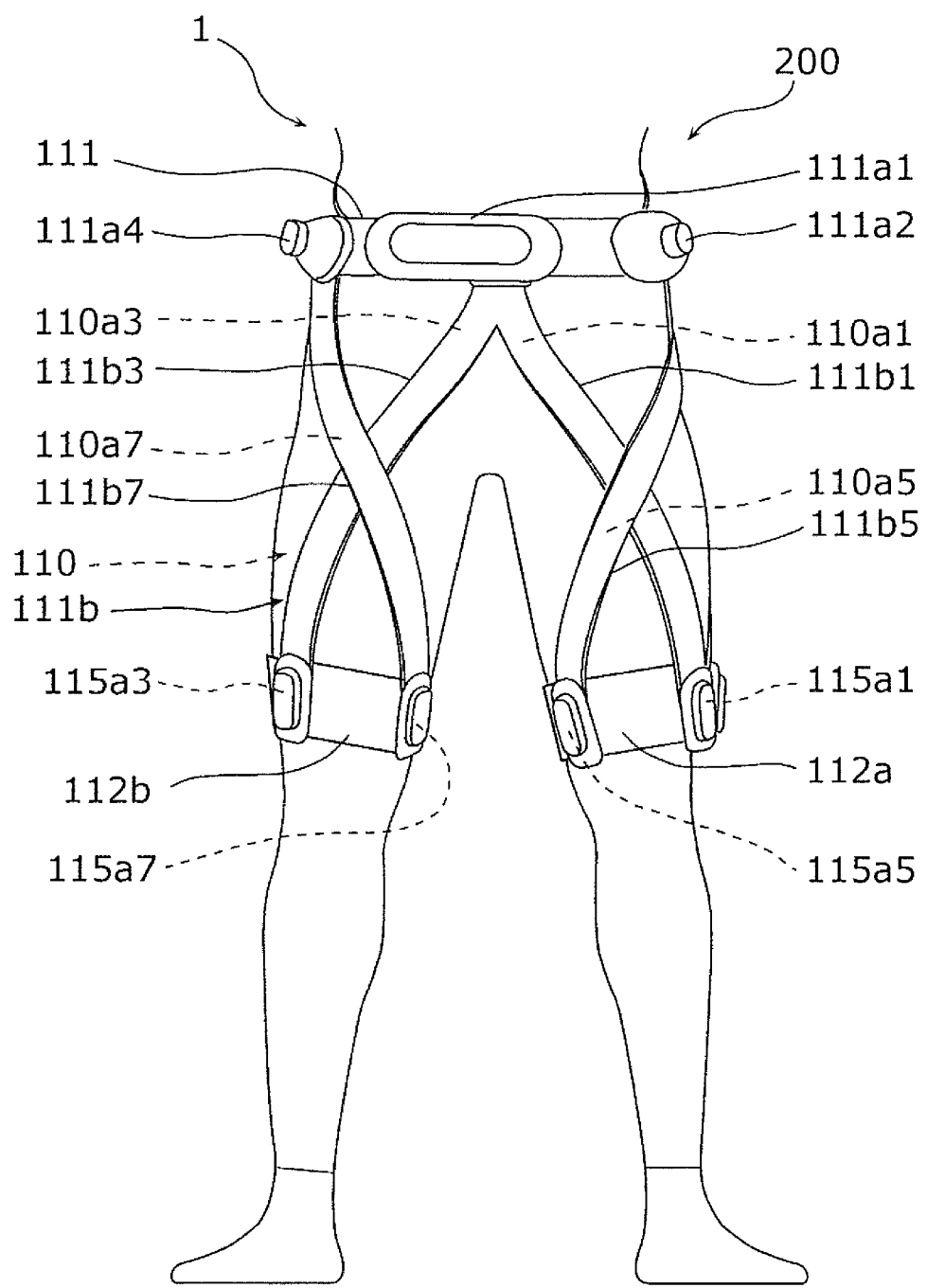
FIG. 14 is a front view of the user wearing the assistance apparatus illustrated in FIG. 13.
Figure 15:
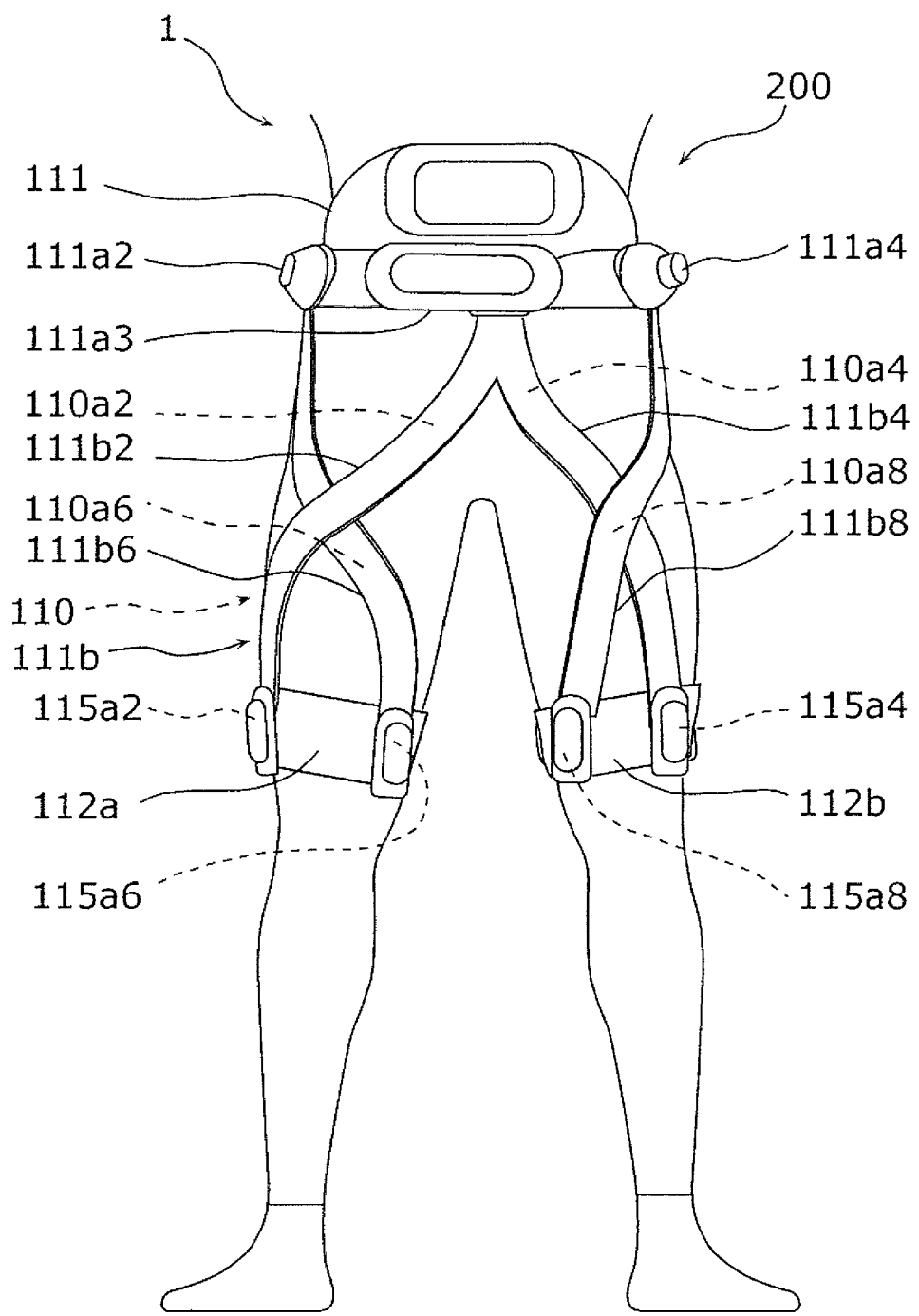
FIG. 15 is a back view of the user wearing the assistance apparatus illustrated in FIG. 13.
Figure 16:
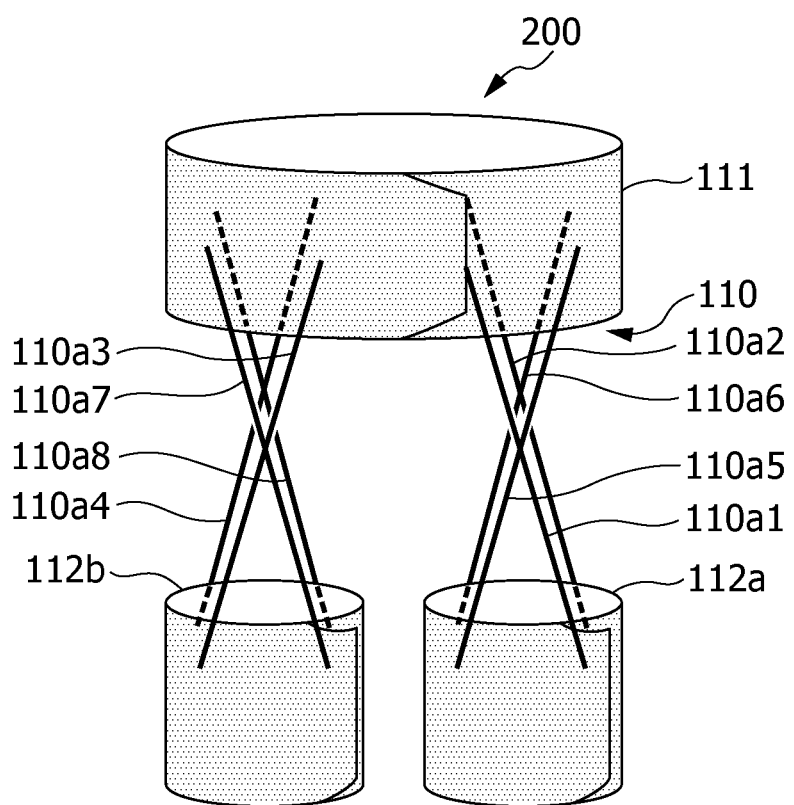
FIG. 16 is a diagram schematically illustrating the arrangement of constituent elements of the assistance apparatus illustrated in FIG. 13.
Figure 17:
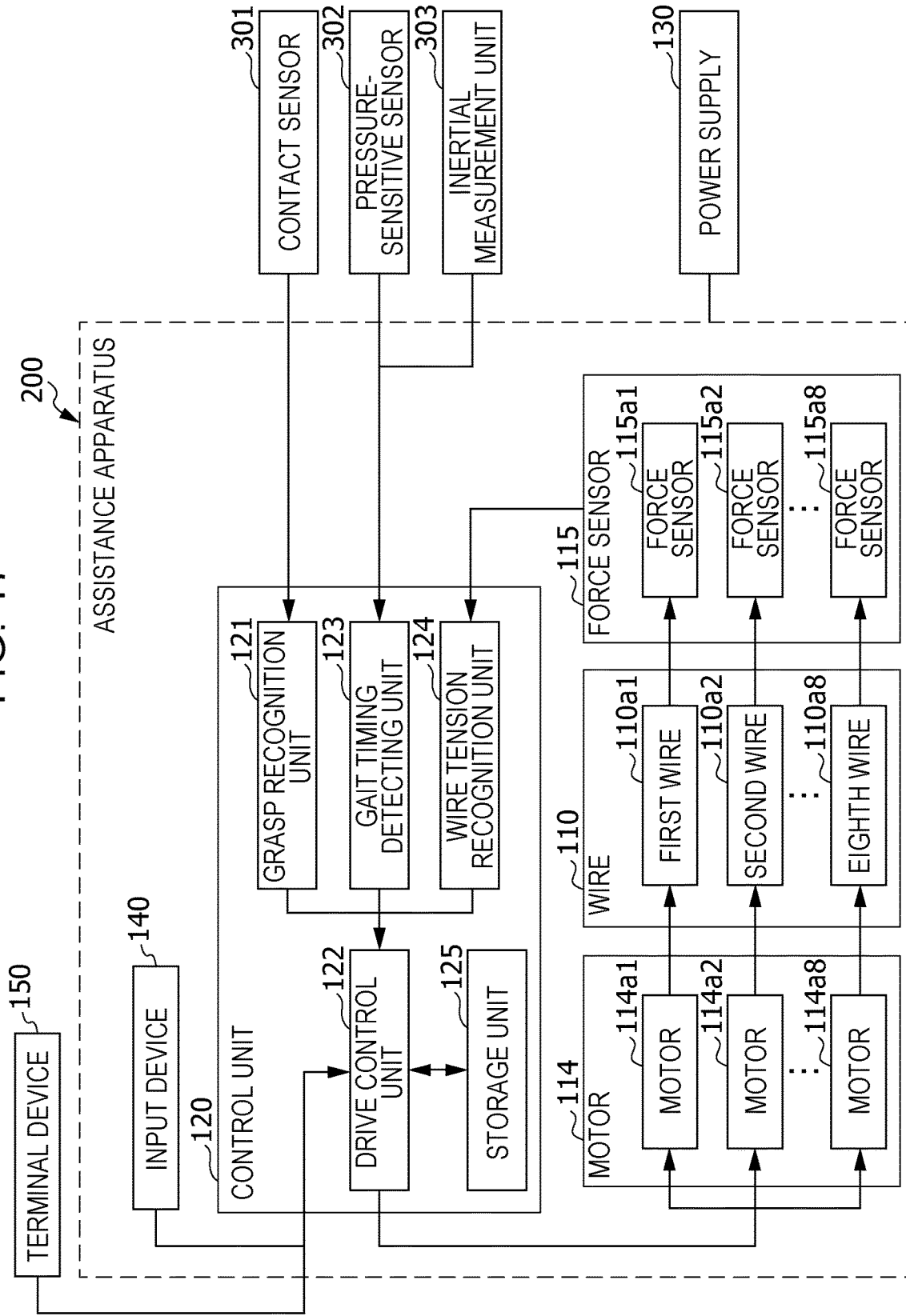
FIG. 17 is a block diagram illustrating a functional configuration of the assistance apparatus illustrated in FIG. 13.

In the assistance apparatus 100 described above, the upper-body belt 111 is coupled to the knee belts 112a and 112b by using the four wires 110a1 to 110a4. However, the number of wires is not limited to that in the embodiment. For example, as illustrated in FIG. 13 to FIG. 17, eight wires may be used. FIG. 13 is a perspective view of a user 1 wearing an assistance apparatus 200 according to a modification of the embodiment, as viewed obliquely from the front. FIG. 14 is a front view of the user 1 wearing the assistance apparatus 200 illustrated in FIG. 13. FIG. 15 is a back view of the user 1 wearing the assistance apparatus 200 illustrated in FIG. 13. FIG. 16 is a diagram schematically illustrating the arrangement of constituent elements of the assistance apparatus 200 illustrated in FIG. 13. FIG. 17 is a block diagram illustrating a functional configuration of the assistance apparatus 200 illustrated in FIG. 13.

As illustrated in FIG. 13 to FIG. 17, the assistance apparatus 200 according to the modification includes an upper-body belt 111, knee belts 112a and 112b, and eight wires, namely, first to eighth wires 110a1 to 110a8. The assistance apparatus 200 further includes a motor 114a1 linked to the first wire 110a1, a motor 114a2 linked to the second wire 110a2, a motor 114a3 linked to the third wire 110a3, a motor 114a4 linked to the fourth wire 110a4, a motor 114a5 linked to the fifth wire 110a5, a motor 114a6 linked to the sixth wire 110a6, a motor 114a7 linked to the seventh wire 110a7, a motor 114a8 linked to the eighth wire 110a8, a force sensor 115a1 disposed on the first wire 110a1, a force sensor 115a2 disposed on the second wire 110a2, a force sensor 115a3 disposed on the third wire 110a3, a force sensor 115a4 disposed on the fourth wire 110a4, a force sensor 115a5 disposed on the fifth wire 110a5, a force sensor 115a6 disposed on the sixth wire 110a6, a force sensor 115a7 disposed on the seventh wire 110a7, a force sensor 115a8 disposed on the eighth wire 110a8, and a control unit 120.

The upper-body belt 111 includes containers 111a1, 111a2, 111a3, and 111a4 so as to correspond to the front part, left side part, back part, and right side part of the body of the user 1, respectively. The motors 114a1 and 114a3 are accommodated in the container 111a1, the motors 114a5 and 114a6 are accommodated in the container 111a2, the motors 114a2 and 114a4 are accommodated in the container 111a3, and the motors 114a7 and 114a8 are accommodated in the container 111a4.

The first wire 110a1 and the fifth wire 110a5 are arranged to extend in directions crossing each other on or above the front part of the body of the user 1, and, more specifically, are arranged to cross each other. Each of the first wire 110a1 and the fifth wire 110a5 has one end fixed to the left knee belt 112a. The first wire 110a1 has another end coupled to the motor 114a1, and the fifth wire 110a5 has another end coupled to the motor 114a5. That is, the first wire 110a1 couples the left knee belt 112a and the motor 114a1 to each other, and the fifth wire 110a5 couples the left knee belt 112a and the motor 114a5 to each other.

The second wire 110a2 and the sixth wire 110a6 are arranged to extend in directions crossing each other on or above the back part of the body of the user 1, and, more specifically, are arranged to cross each other. Each of the second wire 110a2 and the sixth wire 110a6 has one end fixed to the left knee belt 112a. The second wire 110a2 has another end coupled to the motor 114a2, and the sixth wire 110a6 has another end coupled to the motor 114a6. That is, the second wire 110a2 couples the left knee belt 112a and the motor 114a2 to each other, and the sixth wire 110a6 couples the left knee belt 112a and the motor 114a6 to each other.

The third wire 110a3 and the seventh wire 110a7 are arranged to extend in directions crossing each other on or above the front part of the body of the user 1, and, more specifically, are arranged to cross each other. Each of the third wire 110a3 and the seventh wire 110a7 has one end fixed to the right knee belt 112b. The third wire 110a3 has another end coupled to the motor 114a3, and the seventh wire 110a7 has another end coupled to the motor 114a7. That is, the third wire 110a3 couples the right knee belt 112b and the motor 114a3 to each other, and the seventh wire 110a7 couples the right knee belt 112b and the motor 114a7 to each other.

The fourth wire 110a4 and the eighth wire 110a8 are arranged to extend in directions crossing each other on or above the back part of the body of the user 1, and, more specifically, are arranged to cross each other. Each of the fourth wire 110a4 and the eighth wire 110a8 has one end fixed to the right knee belt 112b. The fourth wire 110a4 has another end coupled to the motor 114a4, and the eighth wire 110a8 has another end coupled to the motor 114a8. That is, the fourth wire 110a4 couples the right knee belt 112b and the motor 114a4 to each other, and the eighth wire 110a8 couples the right knee belt 112b and the motor 114a8 to each other.

Further, the first wire 110a1 and the second wire 110a2 extend upward and toward the right side of the body of the user 1 from the left knee belt 112a. Specifically, the first wire 110a1 and the second wire 110a2 extend to the right side of the body of the user 1 while extending upward from the left knee belt 112a, and, for example, extend upward and diagonally to the right from the left knee belt 112a. The fifth wire 110a5 and the sixth wire 110a6 extend upward and toward the left side of the body of the user 1 from the left knee belt 112a. Specifically, the fifth wire 110a5 and the sixth wire 110a6 extend to the left side of the body of the user 1 while extending upward from the left knee belt 112a, and, for example, extend upward and diagonally to the left from the left knee belt 112a. The third wire 110a3 and the fourth wire 110a4 extend upward and toward the left side of the body of the user 1 from the right knee belt 112b. Specifically, the third wire 110a3 and the fourth wire 110a4 extend to the left side of the body of the user 1 while extending upward from the right knee belt 112b, and, for example, extend upward and diagonally to the left from the right knee belt 112b. The seventh wire 110a7 and the eighth wire 110a8 extend upward and toward the right side of the body of the user 1 from the right knee belt 112b. Specifically, the seventh wire 110a7 and the eighth wire 110a8 extend to the right side of the body of the user 1 while extending upward from the right knee belt 112b, and, for example, extend upward and diagonally to the right from the right knee belt 112b.

Figure 18:
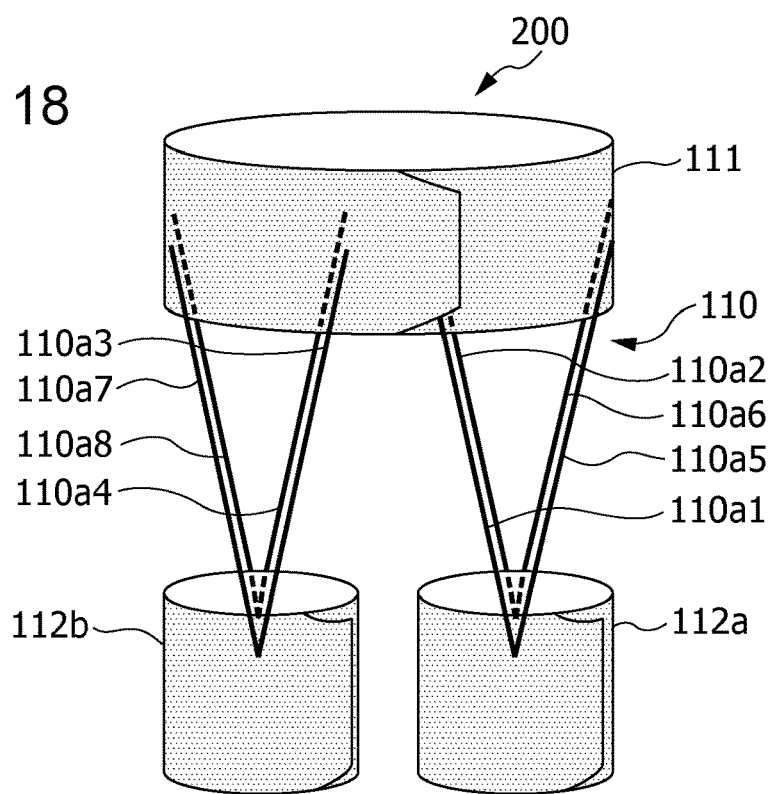
FIG. 18 is a diagram illustrating a modification of the arrangement of wires in the assistance apparatus illustrated in FIG. 13.
Figure 19:
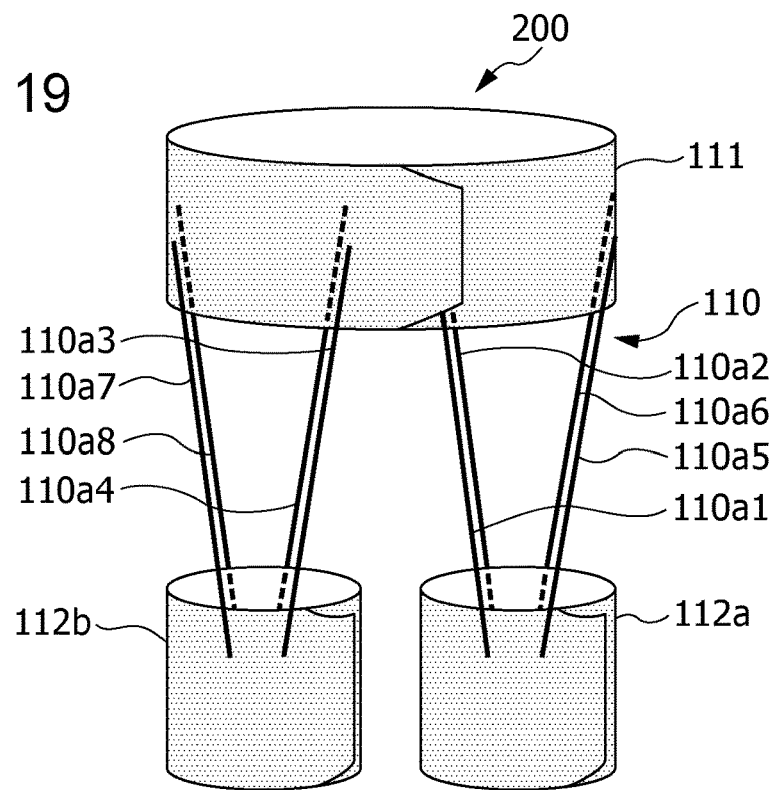
FIG. 19 is a diagram illustrating a modification of the arrangement of wires in the assistance apparatus illustrated in FIG. 13.

Extending of two wires in directions crossing each other is equivalent to crossing of directions in which the two wires extend. Further, crossing of directions in which the two wires extend is equivalent to extending of the two wires in directions that are not parallel to each other. The directions may cross each other at an intersection, or may have no intersection therebetween and may not cross each other. Thus, the two wires may actually cross each other at an intersection or may not actually cross each other. Such two wires extending in directions crossing each other may or may not cross each other when the user 1 is viewed from outside the user 1. When the two wires do not cross each other, as illustrated in FIG. 18 and FIG. 19, the two wires may extend to form a V shape, for example, or may extend away from each other. FIG. 18 and FIG. 19 illustrate modifications of the arrangement of the wires 110 in the assistance apparatus 200 illustrated in FIG. 13.

In this modification, furthermore, eight coupling belts 111b1 to 111b8 are arranged along the first wire 110a1 to the eighth wire 110a8, respectively, and each of the eight coupling belts 111b1 to 111b8 extends from the upper-body belt 111 to the left knee belt 112a or the right knee belt 112b. The coupling belts 111b1 to 111b8 and the first wire 110a1 to the eighth wire 110a8 have a one-to-one correspondence.

In this modification, as a non-limiting example of pairs of two wires extending in directions crossing each other, two wires in each pair of wires cross each other to form an X shape. The first wire 110a1 to the eighth wire 110a8 may have any other arrangement configuration. As illustrated in FIG. 18, for example, the first wire 110a1 and the fifth wire 110a5 may be arranged to form a V shape. In this case, the first wire 110a1 and the fifth wire 110a5 may form a tapered shape that becomes wider toward the top from the left knee belt 112a. In addition, on the left knee belt 112a, the first wire 110a1 and the fifth wire 110a5 may be arranged in close proximity to each other in the manner illustrated in FIG. 18 or may be arranged away from each other in the manner illustrated in FIG. 19. The same applies to the other pairs of wires.

Figure 20:
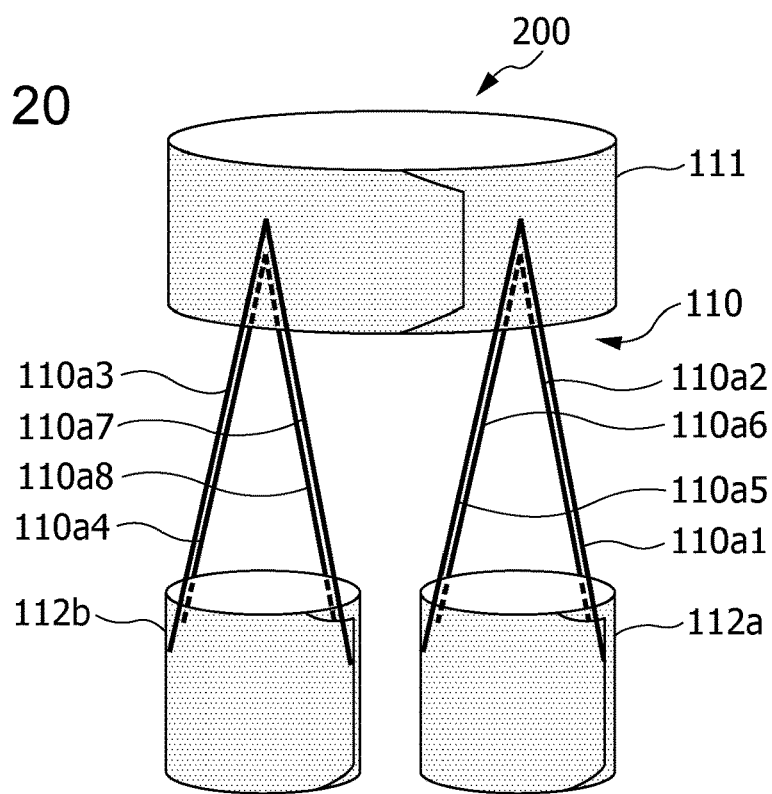
FIG. 20 is a diagram illustrating a modification of the arrangement of wires in the assistance apparatus illustrated in FIG. 13.
Figure 21:
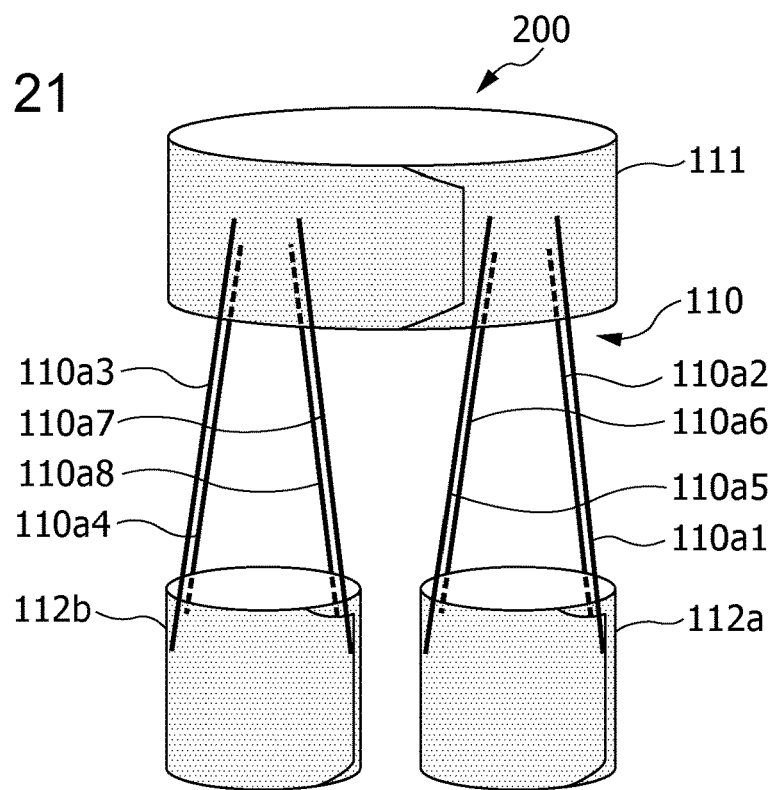
FIG. 21 is a diagram illustrating a modification of the arrangement of wires in the assistance apparatus illustrated in FIG. 13.

Alternatively, as illustrated in FIG. 20, for example, the first wire 110a1 and the fifth wire 110a5 may be arranged to form an inverted V shape. In this case, the first wire 110a1 and the fifth wire 110a5 may form a tapered shape that becomes narrower toward the top from the left knee belt 112a. In addition, on the upper-body belt 111, the first wire 110a1 and the fifth wire 110a5 may be arranged in close proximity to each other in the manner illustrated in FIG. 20 may be arranged away from each other in the manner illustrated in FIG. 21. The same applies to the other pairs of wires. FIG. 20 and FIG. 21 illustrate modifications of the arrangement of the wires 110 in the assistance apparatus 200 illustrated in FIG. 13.

In FIG. 13 to FIG. 15, the first wire 110a1 and the third wire 110a3 extending from the container 111a1 form an inverted V shape, the fifth wire 110a5 and the sixth wire 110a6 extending from the container 111a2 form an inverted V shape, the second wire 110a2 and the fourth wire 110a4 extending from the container 111a3 form an inverted V shape, and the seventh wire 110a7 and the eighth wire 110a8 extending from the container 111a4 form an inverted V shape. However, the arrangement of the first wire 110a1 to the eighth wire 110a8 on the upper-body belt 111 is not limited to the arrangement described above. For example, a wound portion of the first wire 110a1 and a wound portion of the third wire 110a3 may be arranged away from each other so that the two wires 110a1 and 110a3 do not cross each other or may be arranged so that the two wires 110a1 and 110a3 cross each other to form an X shape. A wound portion of the fifth wire 110a5 and a wound portion of the sixth wire 110a6 may be arranged away from each other so that the two wires 110a5 and 110a6 do not cross each other or may be arranged so that the two wires 110a5 and 110a6 cross each other to form an X shape. A wound portion of the second wire 110a2 and a wound portion of the fourth wire 110a4 may be arranged away from each other so that the two wires 110a2 and 110a4 do not cross each other or may be arranged so that the two wires 110a2 and 110a4 cross each other to form an X shape. A wound portion of the seventh wire 110a7 and a wound portion of the eighth wire 110a8 may be arranged away from each other so that the two wires 110a7 and 110a8 do not cross each other or may be arranged so that the two wires 110a7 and 110a8 cross each other to form an X shape.

In the assistance apparatus 200 described above, for example, the motor 114a1 generates a tension in the first wire 110a1, and the motor 114a5 generates a tension in the fifth wire 110a5. The assistance apparatus 200 drives the motor 114a1 to increase the tension of the first wire 110a1. Thus, a force is exerted on the leg of the user 1 in a direction in which the distance between the knee and the heel is reduced to assist a motion of the ankle of the user 1 during walking. The assistance apparatus 200 drives the motor 114a5 to increase the tension of the fifth wire 110a5. Thus, a force is exerted on the leg of the user 1 in a direction in which the distance between the knee and the heel is reduced to assist a motion of the ankle of the user 1 during walking. Further, by setting the tensions of the first wire 110a1 and the fifth wire 110a5 to different values, the assistance apparatus 200 can generate a moment of force regarding a left or right tilt of the heel of the user 1 and can assist a motion of the ankle of the user 1 during walking.

Figure 22A:
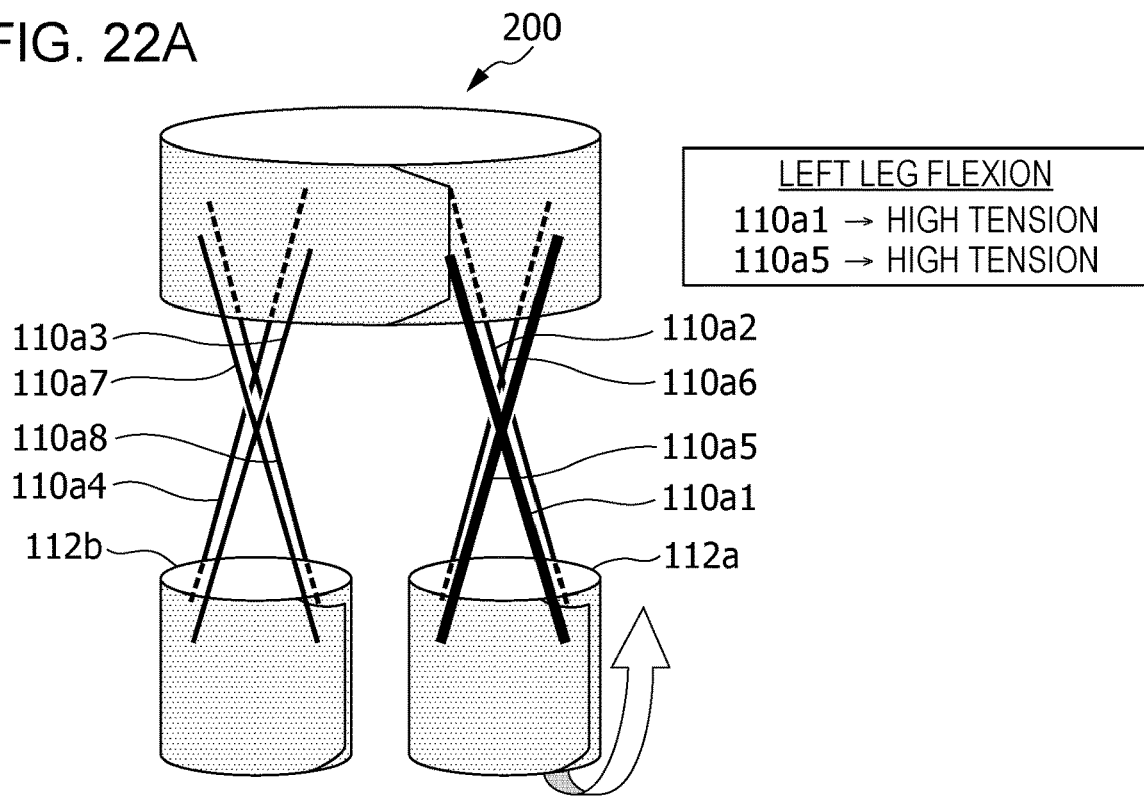
FIG. 22A is a diagram illustrating a case where the assistance apparatus according to the modification assists flexion of the hip joint of the left leg of the user.
Figure 22B:
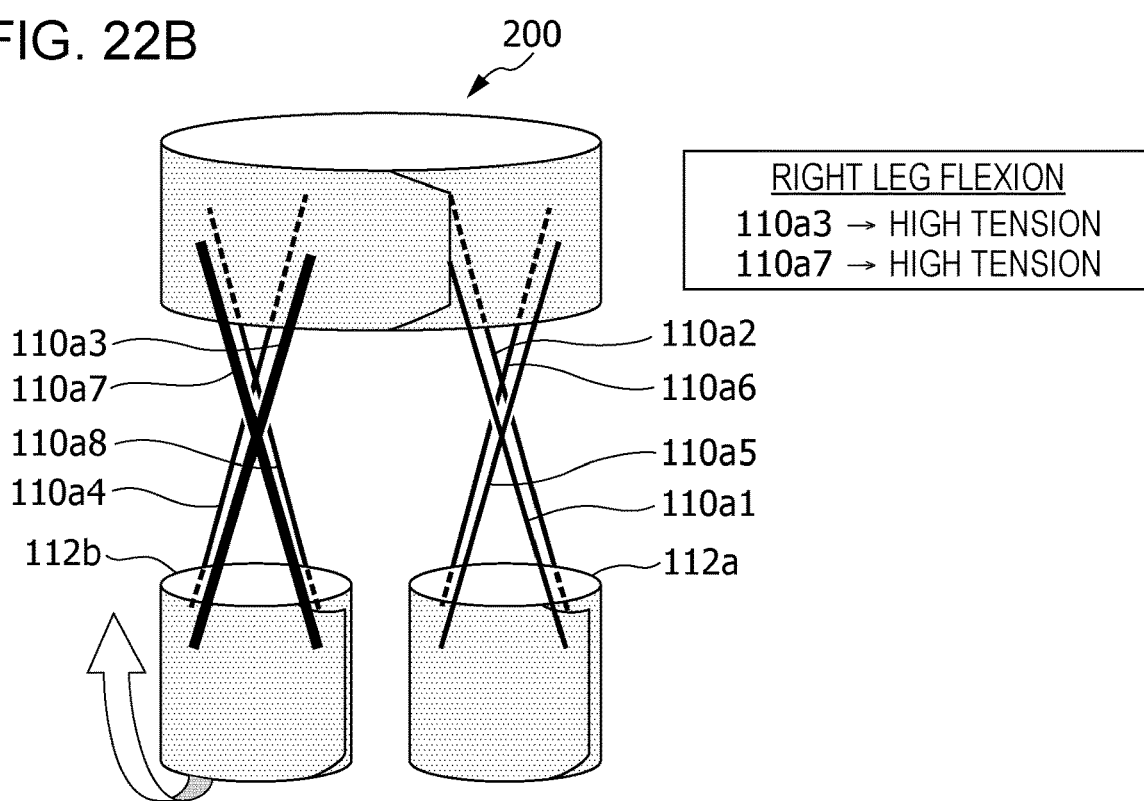
FIG. 22B is a diagram illustrating a case where the assistance apparatus according to the modification assists flexion of the hip joint of the right leg of the user.

The assistance apparatus 200 can apply an assistance force to the hip joint of the left leg and the hip joint of the right leg of the user 1 to flex and extend the hip joints. Referring to FIG. 22A, a case is illustrated in which the assistance apparatus 200 according to the modification assists flexion of the hip joint of the left leg of the user 1. Referring to FIG. 22B, a case is illustrated in which the assistance apparatus 200 according to the modification assists flexion of the hip joint of the right leg of the user 1. In FIG. 22A, to flex the left leg, the drive control unit 122 drives the motors 114a1 and 114a5 to increase the tensions of the first wire 110a1 and the fifth wire 110a5. In FIG. 22B, to flex the right leg, the drive control unit 122 drives the motors 114a3 and 114a7 to increase the tensions of the third wire 110a3 and the seventh wire 110a7. In this modification, the tensions of the first wire 110a1 and the fifth wire 110a5 are assumed to be equivalent, but may be different. In this modification, the tensions of the third wire 110a3 and the seventh wire 110a7 are assumed to be equivalent, but may be different.

Figure 23A:
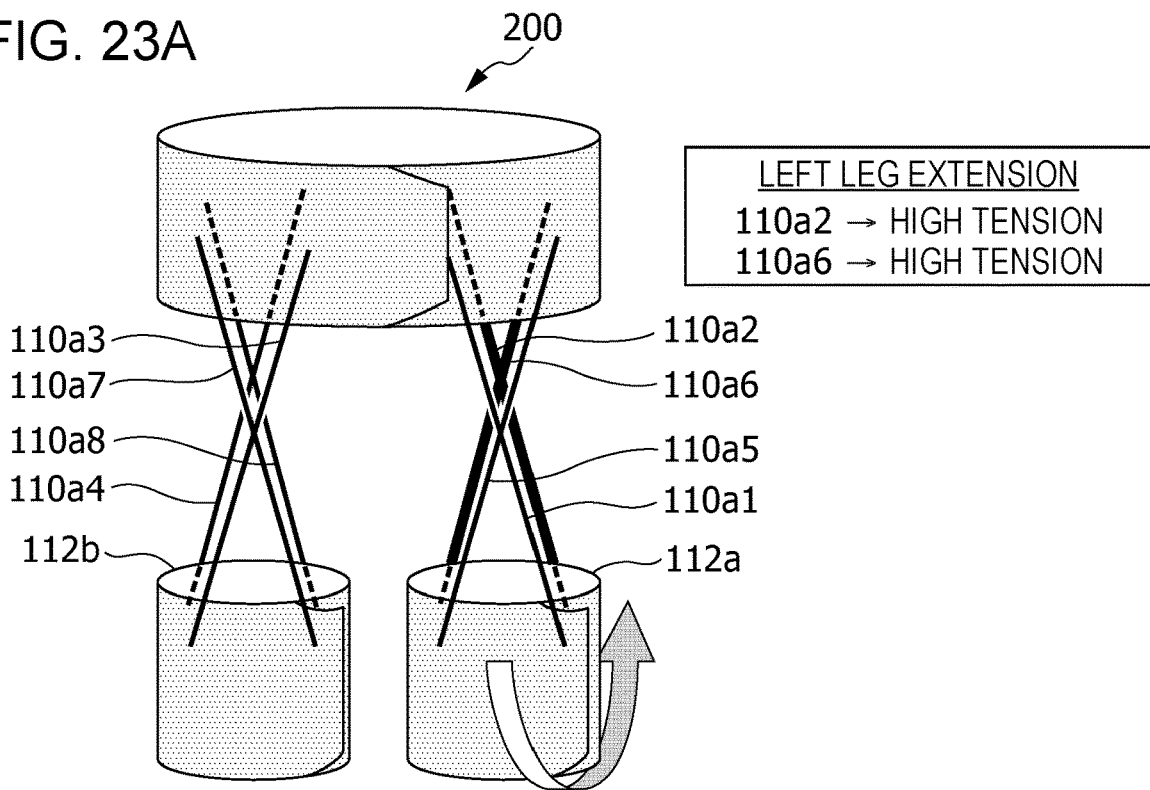
FIG. 23A is a diagram illustrating a case where the assistance apparatus according to the modification assists extension of the hip joint of the left leg of the user.
Figure 23B:
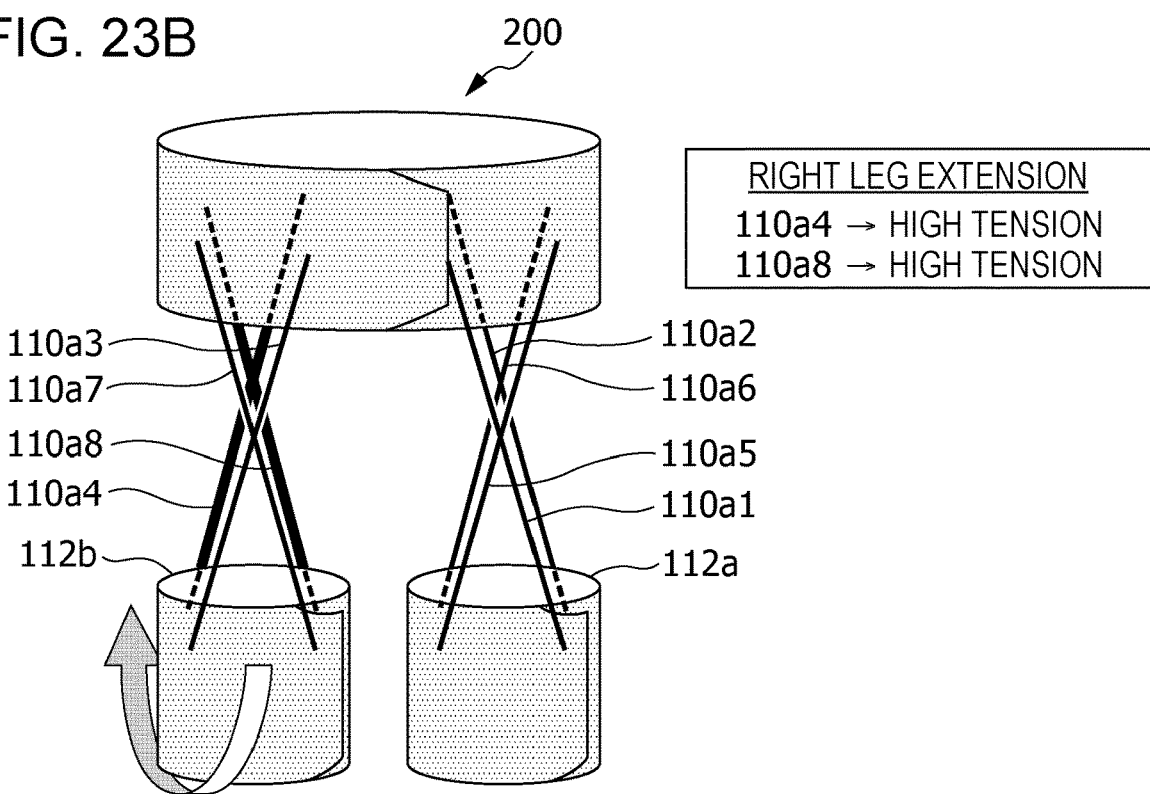
FIG. 23B is a diagram illustrating a case where the assistance apparatus according to the modification assists extension of the hip joint of the right leg of the user.

Referring to FIG. 23A, a case is illustrated in which the assistance apparatus 200 according to the modification assists extension of the hip joint of the left leg of the user 1. Referring to FIG. 23B, a case is illustrated in which the assistance apparatus 200 according to the modification assists extension of the hip joint of the right leg of the user 1. In FIG. 23A, to extend the left leg, the drive control unit 122 increases the tensions of the second wire 110a2 and the sixth wire 110a6. In FIG. 23B, to extend the right leg, the drive control unit 122 increases the tensions of the fourth wire 110a4 and the eighth wire 110a8. The tension of the second wire 110a2 for extension may be similar to the tension of the first wire 110a1 for flexion. The tension of the sixth wire 110a6 for extension may be similar to the tension of the fifth wire 110a5 for flexion. The tension of the fourth wire 110a4 for extension may be similar to the tension of the third wire 110a3 for flexion. The tension of the eighth wire 110a8 for extension may be similar to the tension of the seventh wire 110a7 for flexion.

In the foregoing description, the drive control unit 122 increases the tensions of two wires among the wires 110 to assist one motion of one leg. In this case, the drive control unit 122 may control the motors 114 to adjust the tensions of the wires 110 in accordance with a motion of the user 1 while keeping the tensions of the other six wires at the current value, or may stop the motors 114 corresponding to the six wires so as not to exert the tensions on the six wires.

Figure 24:
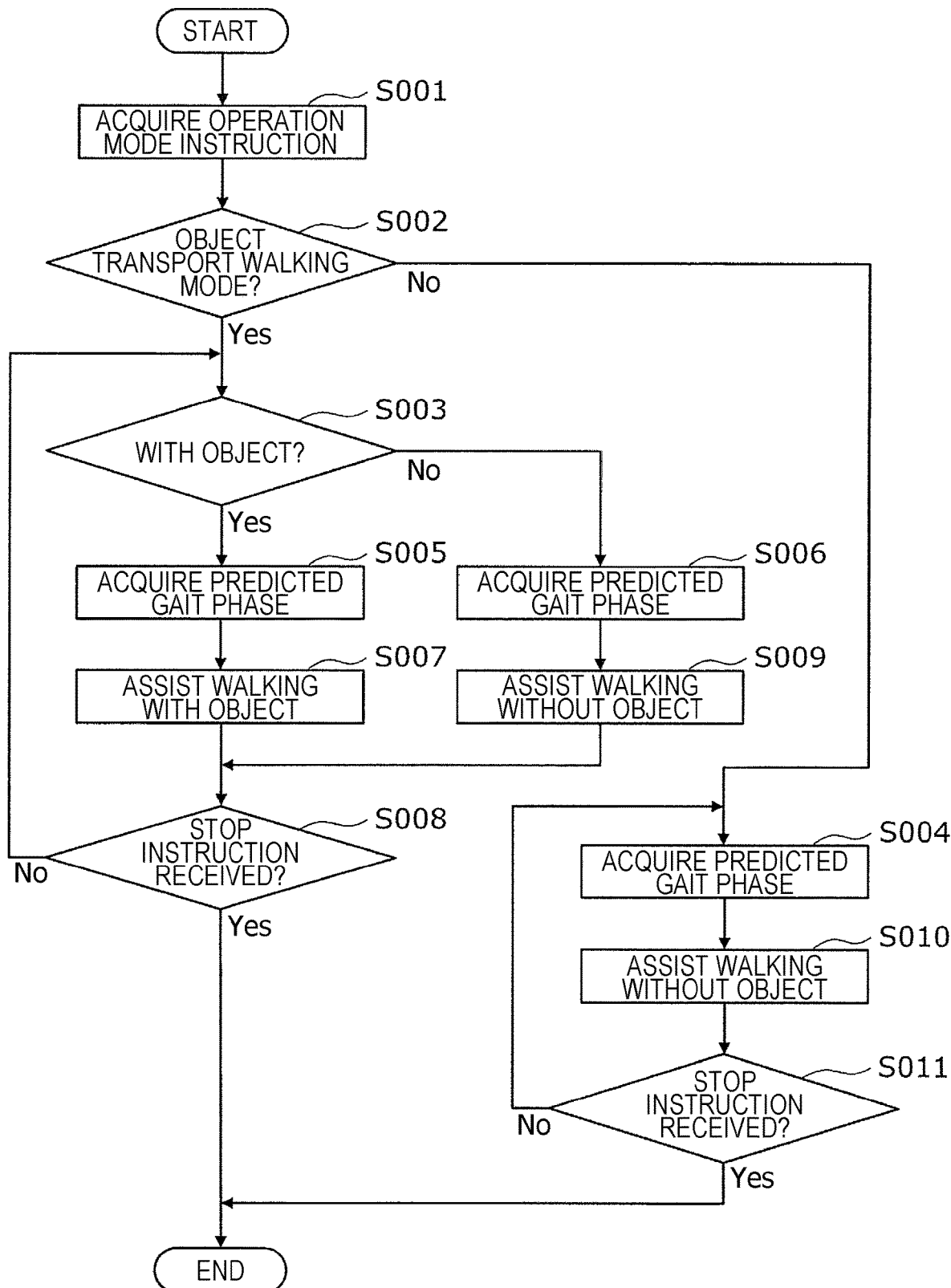
FIG. 24 is a flowchart illustrating an example overall flow of an operation of the assistance apparatus according to the embodiment for assisting a user.

3. Operation of Assistance Apparatus 3-1. Overall Operation of Assistance Apparatus Next, the overall operation flow of an assistance apparatus will be described. Since the assistance apparatus 100 according to the embodiment and the assistance apparatus 200 according to the modification are similar in terms of the overall operation flow of an assistance apparatus, the operation of the assistance apparatus 100 according to the embodiment will be described, with no description given of the operation of the assistance apparatus 200 according to the modification. FIG. 24 is a flowchart illustrating the overall flow of an operation of the assistance apparatus 100 for assisting the user 1.

As illustrated in FIG. 3 and FIG. 24, in step S001, the control unit 120 of the assistance apparatus 100 determines the operation mode of the assistance apparatus 100 in accordance with an operation mode instruction received from the user 1. Specifically, the drive control unit 122 receives an instruction for an operation mode to be implemented by the assistance apparatus 100 from the input device 140 of the assistance apparatus 100 or from the terminal device 150. Examples of the operation mode include a normal walking mode in which a user walks without an object such as an item like luggage, and an object transport walking mode in which a user walks with an object. For example, the user 1 is able to select an operation mode through their decision-making on the basis of not only whether the user 1 is carrying an object but also, when the user 1 is carrying an object, the weight of the object, if necessary.

In step S002, the control unit 120 determines whether the instruction indicates the object transport walking mode. If the instruction indicates the object transport walking mode (Yes in step S002), the control unit 120 proceeds to step S003. If the instruction does not indicate the object transport walking mode (No in step S002), the control unit 120 proceeds to step S004.

In step S003, the grasp recognition unit 121 of the control unit 120 determines whether the user 1 is carrying an object. The grasp recognition unit 121 detects whether the user 1 is carrying an object on the basis of a sensor value acquired from the contact sensor 301 that the user 1 wears on their hand, and outputs a detection result to the drive control unit 122. If the grasp recognition unit 121 determines that the user 1 is carrying an object (Yes in step S003), the process proceeds to step S005. If the grasp recognition unit 121 determines that the user 1 is carrying no object (No in step S003), the process proceeds to step S006.

In step S005, the drive control unit 122 acquires a gait phase predicted by the gait timing detection unit 123. Further, in step S007, the drive control unit 122 controls the motors 114a1 to 114a4 on the basis of the acquired gait phase to generate tensions in the wires 110a1 to 110a4 of the assistance apparatus 100 with input profiles corresponding to the state of walking with an object. That is, by generating tensions in the wires 110*a*1 to 110*a*4, the drive control unit 122 assists the user 1 in flexing and extending the left and right legs. In this case, the drive control unit 122 controls the tension of the wire 110*a*1 on the basis of the tension of the wire 110*a*1, which is acquired from the force sensor 115*a*1, controls the tension of the wire 110*a*2 on the basis of the tension of the wire 110*a*2, which is acquired from the force sensor 115*a*2, controls the tension of the wire 110*a*3 on the basis of the tension of the wire 110*a*3, which is acquired from the force sensor 115*a*3, and controls the tension of the wire 110*a*4 on the basis of the tension of the wire 110*a*4, which is acquired from the force sensor 115*a*4. Accordingly, the assistance apparatus 100 assists the user 1 in walking while carrying an object. The input profiles corresponding to the state of walking with an object will be described in detail below.

Each input profile includes a timing at which a tension is generated in a wire during a gait cycle of the left leg, a period during which a tension is generated in the wire, the value of the tension of the wire during the period, a timing at which a tension is generated in a wire during a gait cycle of the right leg, a period during which a tension is generated in the wire, and the value of the tension of the wire during the period. The input profiles are set in advance and are stored in the storage unit 125. While receiving assistance provided by the assistance apparatus 100, the user 1 may adjust the timing of generation of a wire tension, the period of generation of the wire tension, and the value of the wire tension via the input device 140 or the terminal device 150. The drive control unit 122 may reflect the adjustment results to change the input profile, and may store the changed input profile in the storage unit 125. The drive control unit 122 may control the wire tension by using the changed input profile.

Then, in step S008, the drive control unit 122 determines whether a stop instruction for stopping assistance provided by the assistance apparatus 100 has been acquired from the user 1. If the stop instruction has been acquired (Yes in step S008), the drive control unit 122 stops the operation of the assistance apparatus 100 and terminates the series of processes. If no stop instruction is acquired (No in step S008), the process returns to step S003. The stop instruction may be an instruction for changing the operation mode.

In step S006, the drive control unit 122 acquires a gait phase predicted by the gait timing detection unit 123. Further, in step S009, the drive control unit 122 controls the motors 114*a*1 to 114*a*4 on the basis of the acquired gait phase to generate tensions in the wires 110*a*1 to 110*a*4 of the assistance apparatus 100 with input profiles corresponding to the state of walking without an object. The drive control unit 122 controls the tension of the wire 110*a*1 on the basis of the tension of the wire 110*a*1, which is acquired from the force sensor 115*a*1, controls the tension of the wire 110*a*2 on the basis of the tension of the wire 110*a*2, which is acquired from the force sensor 115*a*2, controls the tension of the wire 110*a*3 on the basis of the tension of the wire 110*a*3, which is acquired from the force sensor 115*a*3, and controls the tension of the wire 110*a*4 on the basis of the tension of the wire 110*a*4, which is acquired from the force sensor 115*a*4, to assist the user 1 in flexing and extending the left and right legs. Accordingly, the assistance apparatus 100 assists the user 1 in walking without an object. The input profiles corresponding to the state of walking without an object will be described in detail below. After the processing of step S009, the drive control unit 122 proceeds to step S008.

In step S004, the drive control unit 122 acquires a gait phase predicted by the gait timing detection unit 123. Further, in step S010, the drive control unit 122 controls the motors 114*a*1 to 114*a*4 on the basis of the acquired gait phase to generate tensions in the wires 110*a*1 to 110*a*4 of the assistance apparatus 100 with input profiles corresponding to the state of walking without an object. The input profiles in step S010 may be equal to the input profiles in step S009. The drive control unit 122 controls the tension of the wire 110*a*1 on the basis of the tension of the wire 110*a*1, which is acquired from the force sensor 115*a*1, controls the tension of the wire 110*a*2 on the basis of the tension of the wire 110*a*2, which is acquired from the force sensor 115*a*2, controls the tension of the wire 110*a*3 on the basis of the tension of the wire 110*a*3, which is acquired from the force sensor 115*a*3, and controls the tension of the wire 110*a*4 on the basis of the tension of the wire 110*a*4, which is acquired from the force sensor 115*a*4, to assist the user 1 in flexing and extending the left and right legs. Accordingly, the assistance apparatus 100 assists the user 1 in walking without an object.

Then, in step S011, the drive control unit 122 determines whether a stop instruction for stopping assistance provided by the assistance apparatus 100 has been acquired from the user 1. If the stop instruction has been acquired (Yes in step S011), the drive control unit 122 stops the operation of the assistance apparatus 100 and terminates the series of processes. If no stop instruction is acquired (No in step S011), the process returns to step S004. The stop instruction may be an instruction for changing the operation mode.

As described above, the assistance apparatus 100 assists a user in walking in accordance with the normal walking mode or the object transport walking mode, which is selected by the user. In the object transport walking mode, the assistance apparatus 100 changes the input profiles of tensions, each of which is generated in one of the wires 110*a*1 to 110*a*4, in accordance with whether the user is carrying an object, and assists the user in accordance with the state of the user.

3-2. Details of Assistance Operation of Assistance Apparatus

An assistance operation of an assistance apparatus will be described in detail. The description will be given of operations of an assistance apparatus for assisting a user in walking when the user walks forward while carrying, or holding, an object such as an item and when the user walks forward while carrying no object. In the embodiment, the operations of the assistance apparatus 100 for assisting a user in walking are the same regardless of whether the user is carrying an object. Specifically, a description will be given of a relationship between a wire for which a tension is to be increased and the timing of increasing the tension of the wire in assistance for flexion and extension of a leg of a user who is walking forward. The operation of the assistance apparatus 100 according to the embodiment and the operation of the assistance apparatus 200 according to the modification are the same, except that the number of wires in which tensions are to be generated for assistance for flexion and extension and maximum tension values are different. Thus, the following describes the operation of the assistance apparatus 100 according to the embodiment, with no description given of the operation of the assistance apparatus 200 according to the modification.

Figure 25:
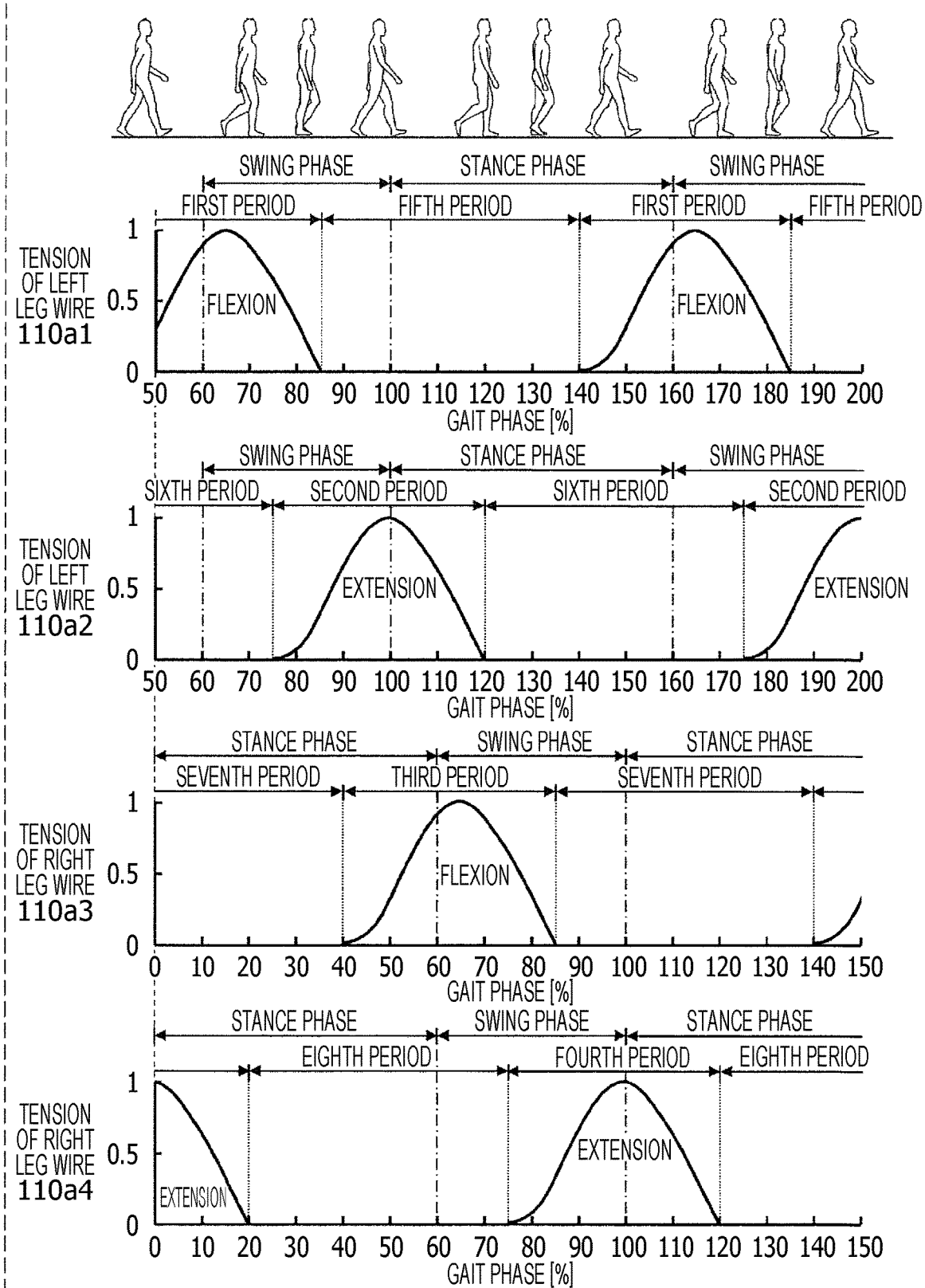
FIG. 25 is a diagram illustrating an example operation of the assistance apparatus according to the embodiment for assisting a user in walking forward.

The drive control unit 122 of the assistance apparatus 100 determines, based on a wire-tension relationship for a type of assistance, namely, either of flexion and extension, wires in which tensions are to be generated, pulling tensions of the wires, and the timing at which and the period during which the tensions of the wires are generated, and assists motions of the user. For example, FIG. 25 illustrates an example operation of the assistance apparatus 100 for assisting a user in walking forward. In this embodiment, the example illustrated in FIG. 25 provides input profiles of wire tensions corresponding walking with and without an object.

In FIG. 25, a relationship is illustrated among a gait state of a user, a gait phase of each leg, and the swing phase and stance phase of each leg. In the illustration of FIG. 25, the gait phase of each leg, wires in which tensions are to be generated, and the states of the tensions of the wires, that is, the input profiles of wire tensions, are associated with each other. An input profile of a wire tension represents the ratio of a wire tension to a maximum tension to be generated in each wire (also referred to as tension gain). For example, when the tension gain of each wire is 100 N, a tension to be actually generated is represented by an expression of a tension value included in the input profile×tension gain. During a period of 0 to 100% of a gait phase, the assistance apparatus 100 produces a wire tension while changing the wire tension, with a maximum tension being 100 N.

In the example illustrated in FIG. 25, the assistance apparatus 100 assists both flexion and extension of the left and right legs of the user. As described above, the assistance apparatus 100 generates a tension in the wire 110a1 to apply an assistance force for flexion to the left leg, and generates a tension in the wire 110a2 to apply an assistance force for extension to the left leg. The assistance apparatus 100 generates a tension in the wire 110a3 to apply an assistance force for flexion to the right leg, and generates a tension in the wire 110a4 to apply an assistance force for extension to the right leg. The assistance apparatus 100 may assist either flexion or extension of the left and right legs of the user, instead of both flexion and extension of the left and right legs of the user.

In FIG. 25, the gait phase of the right leg is used as a reference gait phase. In the gait phase of the right leg, heel strike of the right leg occurs at 0%, and heel strike of the left leg occurs at 50%. In this embodiment, as a non-limiting example, a time point of 0% of the gait phase of the right leg corresponds to a time point of 50% of the gait phase of the left leg. In the example illustrated in FIG. 25, the gait phase of the right leg is used as a reference gait phase, for convenience of illustration. The gait phase of either leg may be used as a reference gait phase, and the gait phase of one leg need not be used as a reference gait phase.

The stance phase of the right leg is a period of 0% or more and 60% or less of the gait phase of the right leg, and the swing phase of the right leg is a period of more than 60% and less than 100% of the gait phase of the right leg.

The swing phase of the left leg is a period of more than 60% and less than 100% of the gait phase of the left leg, and the stance phase of the left leg is a period of 100% or more and 160% or less of the gait phase of the left leg. In the gait phase of the left leg, a period of more than 60% and less than 100% of the gait phase of the left leg, which is the swing phase of the left leg, is included in a first gait cycle of the left leg, and a period of 100% or more and 160% or less of the gait phase of the left leg, which is the stance phase of the left leg, is included in a second gait cycle of the left leg, which is subsequent to the first gait cycle of the left leg. That is, a period of 100% or more and 160% or less of the gait phase of the left leg corresponds to a period of 0% or more and 60% or less of the second gait phase of the left leg. In the following description, a gait phase represented using a value greater than or equal to 100% means a gait phase subsequent to a gait phase represented using a value of 0% to 100%. In FIG. 25, furthermore, a gait phase represented using a value over 100% may be converted into a value of 0% to 100% and represented using the value of 0% to 100%.

When assisting the user in walking forward, for example, the assistance apparatus 100 applies an assistance force for flexion to the left leg at a timing of about 40% of the gait phase of the left leg. A timing of about 40% of the gait phase of the left leg is included in the stance phase of the left leg and the swing phase of the right leg. Specifically, a timing of about 40% of the gait phase of the left leg is a timing immediately before the right leg touches the ground during the swing phase. At this time, the center of gravity of the body of the user shifts forward. When assisting the user in walking forward, for example, the assistance apparatus 100 applies an assistance force for flexion to the right leg at a timing of about 40% of the gait phase of the right leg. A timing of about 40% of the gait phase of the right leg is included in the swing phase of the left leg and the stance phase of the right leg. Specifically, a timing of about 40% of the gait phase of the right leg is a timing immediately before the left leg touches the ground during the swing phase. At this time, the center of gravity of the body of the user shifts forward.

Further, the assistance apparatus 100 applies an assistance force for extension to the left leg at a timing of about 75% of the gait phase of the left leg, for example. A timing of about 75% of the gait phase of the left leg is included in the swing phase of the left leg and the stance phase of the right leg. Specifically, a timing of about 75% of the gait phase of the left leg is a timing in the middle of moving the left leg of the user forward during the swing phase and is included in the period during which the center of gravity of the body of the user shifts from backward to forward. Further, the assistance apparatus 100 applies an assistance force for extension to the right leg at a timing of about 75% of the gait phase of the right leg, for example. A timing of about 75% of the gait phase of the right leg is included in the stance phase of the left leg and the swing phase of the right leg. Specifically, a timing of about 75% of the gait phase of the right leg is a timing in the middle of moving the right leg of the user forward during the swing phase and is included in the period during which the center of gravity of the body of the user shifts from backward to forward.

When assisting the user in walking forward, the assistance apparatus 100 generates a tension greater than or equal to a first threshold value in each of the wires 110a1 to 110a4. In the example illustrated in FIG. 25, the respective tensions of the wires 110a1 to 110a4 are 100 N, for example. The first threshold value may be a tension value that allows the user to recognize that flexion or extension is promoted by a tension generated in a wire. The first threshold value is, for example, 40 N, which is 40% of 100 N. In the example illustrated in FIG. 25, the assistance apparatus 100 generates a wire tension in each of the wires 110a1 to 110a4 in such a manner that the wire tension gradually increases, reaches a maximum tension, and then gradually decreases during the period of generation of the wire tension. The input profiles of the wire tensions generated in the wires 110a1 to 110a4 by the assistance apparatus 100 each exhibit a waveform that is convex curve. In this example, the maximum tension is 100 N.

To assist flexion of the left leg, for example, the assistance apparatus 100 continuously generates a tension in the wire 110a1 during the entirety of a first period, which is a period of 40% or more and 85% or less of the gait phase of the left leg. Then, the assistance apparatus 100 generates a tension greater than or equal to the first threshold value in the wire 110a1 during at least a portion of the first period. In the first period, the left leg shifts from the stance phase to the swing phase. Applying an assistance force for flexion to the left leg in the shift from the stance phase to the swing phase allows the user to easily raise the left leg and ensures that the user can easily walk.

In the example illustrated in FIG. 25, the assistance apparatus 100 generates no tension in the wire 110$a$1 during a fifth period, which is a period other than the first period. The fifth period may be a period of 0% or more and less than 40% of the gait phase of the left leg and a period of more than 85% and less than 100% of the gait phase of the left leg. However, the assistance apparatus 100 may generate a tension during the fifth period. For example, the assistance apparatus 100 may generate a tension less than a second threshold value in the wire 110$a$1 during the fifth period. The second threshold value is a tension value that is smaller than the first threshold value and that is not perceivable by the user, for example. For example, the second threshold value may be a tension value that prevents the wire 110$a$1 from loosening. The second threshold value is a value that is 0.2 to 0.4 times the first threshold value or is 10 N, for example. In the specification and the appended claims, generation of a tension less than the second threshold value means generation of a tension greater than or equal to 0 and less than the second threshold value and includes generation of a tension of 0.

The start timing of the first period may be included in a period of 35% or more and 55% or less of the gait phase of the left leg. The end timing of the first period may be included in a period of 80% or more and 90% or less of the gait phase of the left leg. In the example illustrated in FIG. 25, the wire tension is maximum at a timing of 65% of the gait phase of the left leg. However, the wire tension may be maximum at a time during a period of 60% or more and 70% or less of the gait phase of the left leg. Thus, the first period may be a period of 35% or more and 90% or less of the gait phase of the left leg.

To assist extension of the left leg, for example, the assistance apparatus 100 continuously generates a tension in the wire 110$a$2 during the entirety of a second period, which is a period of 75% or more and 120% or less of the gait phase of the left leg. Then, the assistance apparatus 100 generates a tension greater than or equal to the first threshold value in the wire 110$a$2 during at least a portion of the second period. In the second period, the left leg shifts from the swing phase to the stance phase. Applying an assistance force for extension to the left leg in the shift from the swing phase to the stance phase allows the left leg of the user to touch the ground stably and ensures that the user can easily walk. In the example illustrated in FIG. 25, the assistance apparatus 100 generates no tension in the wire 110$a$2 during a sixth period, which is a period other than the second period. The sixth period may be a period of more than 20% and less than 75% of the gait phase of the left leg. However, the assistance apparatus 100 may generate a tension less than the second threshold value during the sixth period.

The start timing of the second period may be included in a period of 65% or more and 90% or less of the gait phase of the left leg. The end timing of the second period may be included in a period of 110% or more and 125% or less of the gait phase of the left leg. In the example illustrated in FIG. 25, the wire tension is maximum at a timing of 100% of the gait phase of the left leg. However, the wire tension may be maximum at a time during a period of 85% or more and 100% or less of the gait phase of the left leg. Thus, the second period may be a period of 65% or more and 125% or less of the gait phase of the left leg, that is, may include a period of 0% or more and 25% or less of the gait phase of the left leg and a period of 65% or more and less than 100% of the gait phase of the left leg.

To assist flexion of the right leg, for example, the assistance apparatus 100 continuously generates a tension in the wire 110$a$3 during the entirety of a third period, which is a period of 40% or more and 85% or less of the gait phase of the right leg. Then, the assistance apparatus 100 generates a tension greater than or equal to the first threshold value in the wire 110$a$3 during at least a portion of the third period. In the third period, the right leg shifts from the stance phase to the swing phase. In the example illustrated in FIG. 25, the assistance apparatus 100 generates no tension in the wire 110$a$3 during a seventh period, which is a period other than the third period. The seventh period may be a period of 0% or more and less than 40% of the gait phase of the right leg and a period of more than 85% and less than 100% of the gait phase of the right leg. However, the assistance apparatus 100 may generate a tension less than the second threshold value during the seventh period.

The start timing of the third period may be included in a period of 35% or more and 55% or less of the gait phase of the right leg. The end timing of the third period may be included in a period of 80% or more and 90% or less of the gait phase of the right leg. In the example illustrated in FIG. 25, the wire tension is maximum at a timing of 65% of the gait phase of the right leg. However, the wire tension may be maximum at a time during a period of 60% or more and 70% or less of the gait phase of the right leg. Thus, the third period may be a period of 35% or more and 90% or less of the gait phase of the right leg.

To assist extension of the right leg, for example, the assistance apparatus 100 continuously generates a tension in the wire 110$a$4 during the entirety of a fourth period, which is a period of 75% or more and 120% or less of the gait phase of the right leg. Then, the assistance apparatus 100 generates a tension greater than or equal to the first threshold value in the wire 110$a$4 during at least a portion of the fourth period. In the fourth period, the right leg shifts from the swing phase to the stance phase. In the example illustrated in FIG. 25, the assistance apparatus 100 generates no tension in the wire 110$a$4 during an eighth period, which is a period other than the fourth period. The eighth period may be a period of more than 20% and less than 75% of the gait phase of the right leg. However, the assistance apparatus 100 may generate a tension less than the second threshold value during the eighth period.

The start timing of the fourth period may be included in a period of 65% or more and 90% or less of the gait phase of the right leg. The end timing of the fourth period may be included in a period of 110% or more and 125% or less of the gait phase of the right leg. In the example illustrated in FIG. 25, the wire tension is maximum at a timing of 100% of the gait phase of the right leg. However, the wire tension may be maximum at a time during a period of 85% or more and 100% or less of the gait phase of the right leg. Thus, the fourth period may be a period of 65% or more and 125% or less of the gait phase of the right leg, that is, may include a period of 0% or more and 25% or less of the gait phase of the right leg and a period of 65% or more and less than 100% of the gait phase of the right leg.

As described above, during the entirety of a period corresponding to each input profile of a wire tension, the assistance apparatus 100 continuously generates a tension in the wire corresponding to the input profile. However, the embodiment is not limited to this. The assistance apparatus 100 may temporarily stop the generation of the tension in the wire during the period corresponding to the input profile. In this case, a load imposed on the leg of the user by the assistance apparatus 100 is reduced, and the load felt by the user on which the assistance apparatus 100 acts is reduced.

The input profiles of wire tensions illustrated in FIG. 25 are set so that the tension of each wire rises earlier than a desired time point by several percent (%) of the gait phase in consideration of a time delay from when the drive control unit 122 outputs a signal to the corresponding motor to when a tension is actually generated in the wire. For example, in the example illustrated in FIG. 25, input profiles of wire tensions are created so that the tension of each wire rises earlier than a desired time point by approximately 5%. For assistance for flexion, the assistance apparatus 100 provides assistance so that the assistance for flexion is completed immediately before the heel strikes the ground. Thus, input profiles of wire tensions are created so that assistance for flexion ends at a time during a period of 80% or more and 90% or less of the gait phase of the each leg in order to complete assistance for flexion at a timing of about 100% of the gait phase of each leg in consideration of a delay of output of the tension of each wire.

Figure 26:
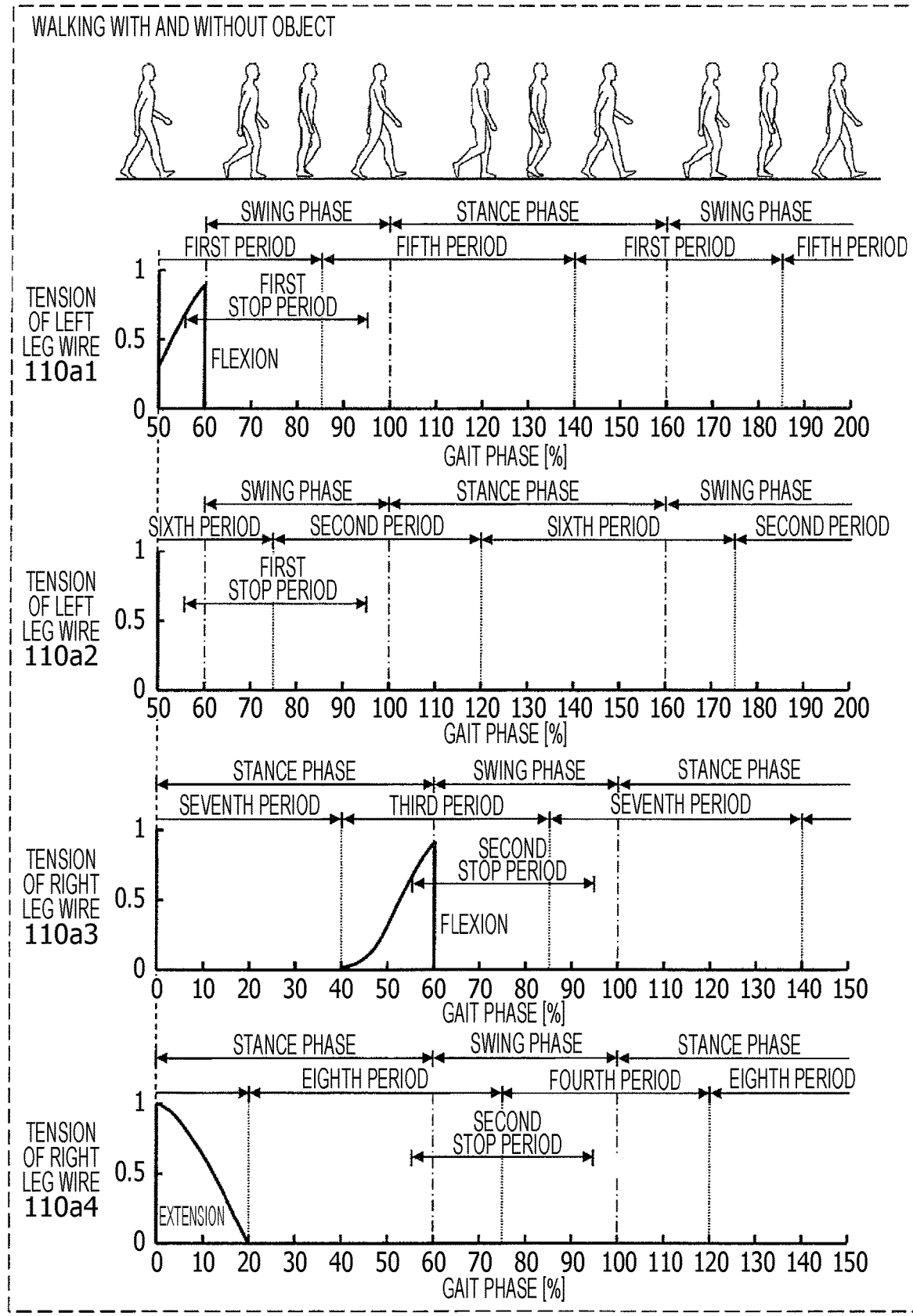
FIG. 26 is a diagram illustrating an example operation of the assistance apparatus for stopping assistance in a state illustrated in FIG. 25.

In this embodiment, furthermore, the assistance apparatus 100 stops assistance in a way described below. In this case, the drive control unit 122 stops assisting the left leg and stops assisting the right leg at shifted timings. Specifically, when assistance of the left leg is stopped and thereafter assistance of the right leg is stopped, for example, the drive control unit 122 controls wire tensions in a way illustrated in FIG. 26. The drive control unit 122 stops generating a tension in the first wire 110a1 and the second wire 110a2 at any timing during a first stop period in the gait phase of the left leg starting in a boundary period in the first period and ending in a start period of the second period. FIG. 26 is a diagram illustrating an example operation of the assistance apparatus 100 for stopping assistance in the state illustrated in FIG. 25.

Specifically, the drive control unit 122 reduces the tension of the first wire 110a1 to less than the second threshold value and to zero in the first stop period. After the first stop period, the drive control unit 122 does not generate a tension greater than or equal to the second threshold value in the first wire 110a1, that is, does not provide assistance for flexion, in and after the fifth period. In this way, the drive control unit 122 stops assistance with the first wire 110a1 in the first stop period. Further, the drive control unit 122 stops generating a tension in the second wire 110a2 at the same timing as the first wire 110a1. Note that the timing of stopping generating a tension in the first wire 110a1 and the timing of stopping generating a tension in the second wire 110a2 may be arranged in any order if both timings fall within the first stop period. The drive control unit 122 reduces the tension of the second wire 110a2 to less than the second threshold value and to zero in the first stop period. After the first stop period, the drive control unit 122 does not generate a tension greater than or equal to the second threshold value in the second wire 110a2, that is, does not provide assistance for extension, in and after the second period. In this way, the drive control unit 122 stops assistance with the second wire 110a2 in the first stop period. In the example illustrated in FIG. 26, the drive control unit 122 reduces the tensions of the first wire 110a1 and the second wire 110a2 to zero at the same timing.

The term "same timing", as used herein, is used to include not only exactly the same timing but also different timings or timings with a difference. The difference may be less than 10% or may be 5% or less in terms of the value of the gait phase. For example, when the difference is 5% or less, as an example, the values at all timings in the gait phase are included in a range of values of the gait phase, which is within ±5% from an average value of values at the timings in the gait phase.

The boundary period in the first period includes a boundary at which the left leg of the user shifts from the stance phase to the swing phase. An example of the boundary period in the first period is a period of 55% or more and 65% or less of the gait phase of the left leg. The start period of the second period includes a period up to a time point that progresses by about 5% from the timing at which the second period starts in the gait phase of the left leg. An example of the start period of the second period is a period of 65% or more and 95% or less of the gait phase of the left leg. Thus, the first stop period may include a period of 55% or more and 95% or less of the gait phase of the left leg. Substantially all of the first stop period is included in the swing phase of the left leg. In the example illustrated in FIG. 26, the drive control unit 122 stops generating a tension in the first wire 110a1 and the second wire 110a2 and reduces the tension to zero in the first stop period immediately after the left leg shifts to the swing phase, that is, at a timing of 60% of the gait phase of the left leg.

Further, the drive control unit 122 stops generating a tension in the third wire 110a3 and the fourth wire 110a4 at any timing during a second stop period in the gait phase of the right leg starting in a boundary period in the third period and ending in a start period of the fourth period. Specifically, the drive control unit 122 reduces the tension of the third wire 110a3 to less than the second threshold value and to zero in the second stop period. After the second stop period, the drive control unit 122 does not generate a tension greater than or equal to the second threshold value in the third wire 110a3, that is, does not provide assistance for flexion, in and after the seventh period. In this way, the drive control unit 122 stops assistance with the third wire 110a3 in the second stop period. Further, the drive control unit 122 stops generating a tension in the fourth wire 110a4 at the same timing as the third wire 110a3. Note that the timing of stopping generating a tension in the third wire 110a3 and the timing of stopping generating a tension in the fourth wire 110a4 may be arranged in any order if both timings fall within the second stop period. The drive control unit 122 reduces the tension of the fourth wire 110a4 to less than the second threshold value and to zero in the second stop period. After the second stop period, the drive control unit 122 does not generate a tension greater than or equal to the second threshold value in the fourth wire 110a4, that is, does not provide assistance for extension, in and after the fourth period. In this way, the drive control unit 122 stops assistance with the fourth wire 110a4 in the second stop period. In the example illustrated in FIG. 26, the drive control unit 122 reduces the tensions of the third wire 110a3 and the fourth wire 110a4 to zero at the same timing.

The boundary period in the third period includes a boundary at which the right leg of the user shifts from the stance phase to the swing phase. An example of the boundary period in the third period is a period of 55% or more and 65% or less of the gait phase of the right leg. The start period of the fourth period includes a period up to a time point that progresses by about 5% from the timing at which the fourth period starts in the gait phase of the right leg. An example of the start period of the fourth period is a period of 65% or more and 95% or less of the gait phase of the right leg. Thus, the second stop period may include a period of 55% or more and 95% or less of the gait phase of the right leg. Substantially all of the second stop period is included in the swing phase of the right leg. In the example illustrated in FIG. 26, the drive control unit 122 stops generating a tension in the third wire 110a3 and reduces the tension to zero in the second stop period immediately after the right leg shifts to the swing phase, that is, at a timing of 60% of the gait phase of the right leg.

As described above, when the left leg for which flexion is being assisted shifts to the swing phase, the assistance apparatus 100 stops generating a tension in the first wire 110a1, thereby stopping assisting flexion of the left leg. When the right leg for which flexion is being assisted shifts to the swing phase, the assistance apparatus 100 stops generating a tension in the third wire 110a3, thereby stopping assisting flexion of the right leg. Further, the assistance apparatus 100 stops generating a tension in the second wire 110a2 and the fourth wire 110a4 without generating a tension greater than or equal to the first threshold value, thereby stopping assisting extension of the left and right legs. Thus, the assistance apparatus 100 stops assisting extension without substantially generating an assistance force for extension in each of the first stop period and the second stop period. This can prevent the user from feeling uncomfortable with the left and right legs even if assistance for either flexion or extension of each of the left and right legs is stopped, and can prevent instability of the left leg and the right leg due to lack of assistance for flexion.

In addition, the first stop period and the second stop period do not overlap. Accordingly, the assistance apparatus 100 stops assisting the left leg and stops assisting the right leg sequentially with a time difference. For example, if the assistance apparatus 100 stops assisting the left leg and stops assisting the right leg simultaneously, the user may lose the balance between the movements of the left and right legs and can fall. The assistance apparatus 100 can stop assistance while keeping the movements of the left and right legs of the user in balance. In the example illustrated in FIG. 26, the first stop period occurs earlier than the second stop period. Alternatively, the second stop period may occur earlier than the first stop period. In this case, the assistance apparatus 100 stops assisting the right leg and thereafter stops assisting the left leg.

In the foregoing, the assistance apparatus 100 stops assisting the left leg in a period from the first period to the second period in the gait phase of the left leg and stops assisting the right leg in a period from the third period to the fourth period in the gait phase of the right leg, as a non-limiting example. The assistance apparatus 100 may stop assisting the left leg in a period from the second period to the first period in the gait phase of the left leg and stop assisting the right leg in a period from the fourth period to the third period in the gait phase of the right leg.

Figure 27A:
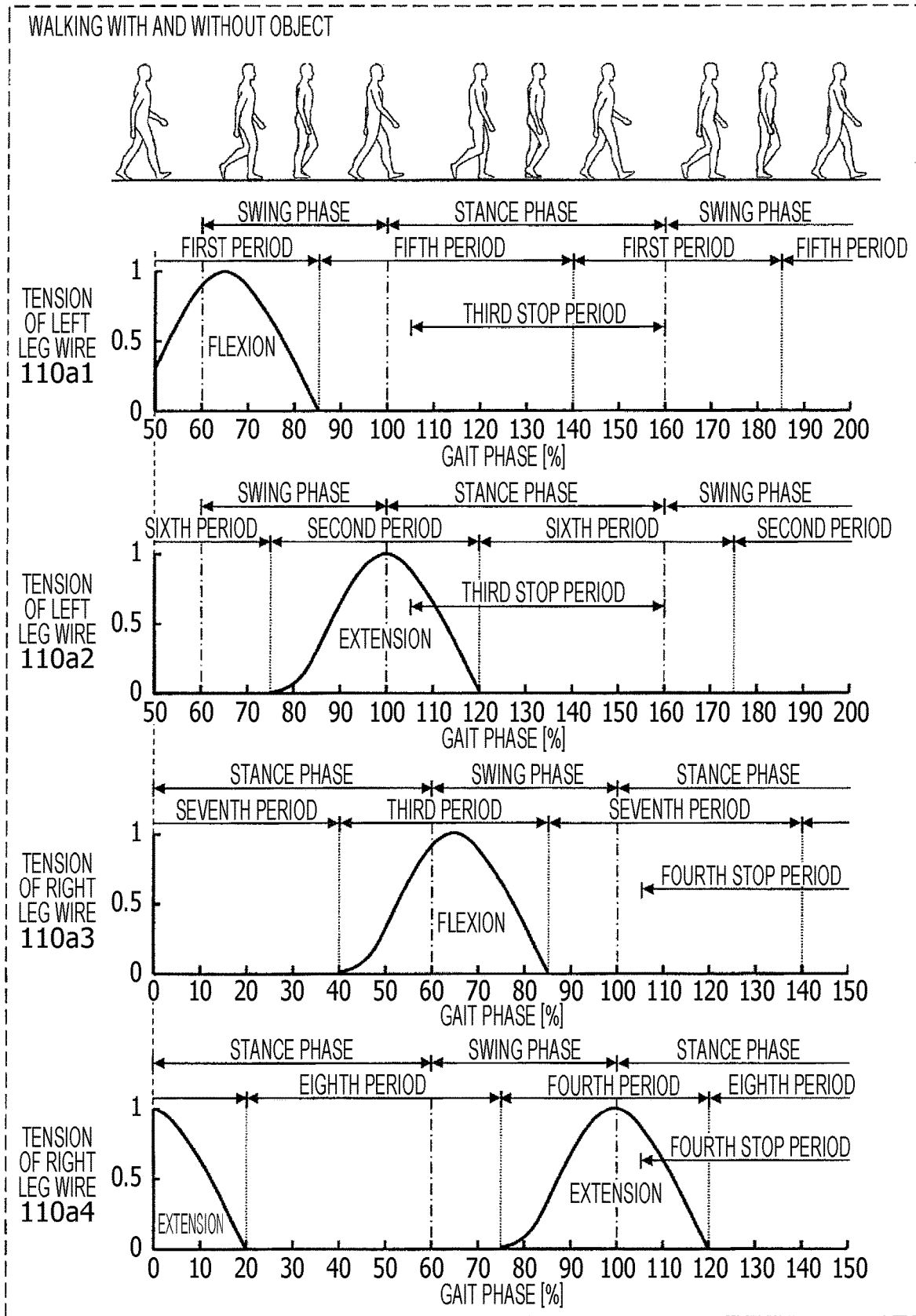
FIG. 27A is a diagram illustrating another example operation of the assistance apparatus for stopping assistance in the state illustrated in FIG. 25.
Figure 27B:
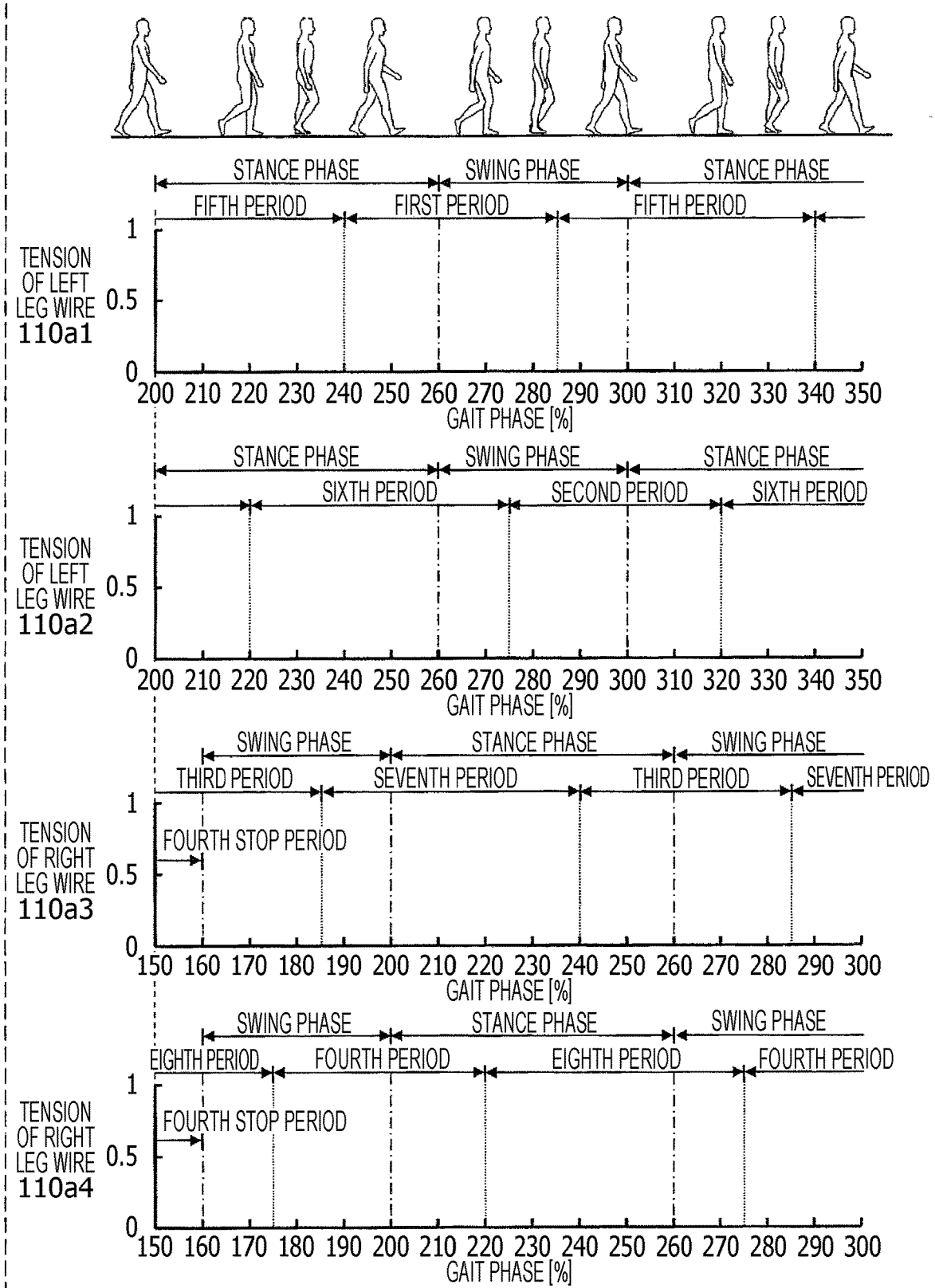
FIG. 27B is a diagram illustrating another example operation of the assistance apparatus for stopping assistance in the state illustrated in FIG. 25.

Specifically, when assistance of the left leg is stopped and thereafter assistance of the right leg is stopped, for example, the drive control unit 122 controls wire tensions in a way illustrated in FIG. 27A and FIG. 27B. The drive control unit 122 stops generating a tension in the first wire 110a1 and the second wire 110a2 at any timing during a third stop period in the gait phase of the left leg starting in an end period of the second period and ending in a start period of the first period. FIG. 27A and FIG. 27B are diagrams illustrating another example operation of the assistance apparatus 100 for stopping assistance in the state illustrated in FIG. 25, and illustrate a continuous operation of the assistance apparatus 100.

The drive control unit 122 reduces the tension of the first wire 110a1 and the second wire 110a2 to less than the second threshold value and to zero in the third stop period. After the third stop period, the drive control unit 122 does not generate a tension greater than or equal to the second threshold value in the first wire 110a1 and the second wire 110a2 in and after the first period and the sixth period. In this way, the drive control unit 122 stops assistance with the first wire 110a1 and the second wire 110a2 in the third stop period. In the example illustrated in FIG. 27A and FIG. 27B, the drive control unit 122 reduces the tensions of the first wire 110a1 and the second wire 110a2 to zero at the same timing. However, the timing of stopping generating a tension in the first wire 110a1 and the timing of stopping generating a tension in the second wire 110a2 may be arranged in any order if both timings fall within the third stop period.

The end period of the second period includes a period up to a time point that occurs at about 5% before the timing at which the second period ends. An example of the end period of the second period is a period of 5% or more and 25% or less of the gait phase of the left leg. The start period of the first period includes a period up to a time point that progresses by about 5% from the timing at which the first period starts in the gait phase of the left leg. An example of the start period of the first period is a period of 35% or more and 60% or less of the gait phase of the left leg. Thus, the third stop period may include a period of 5% or more and 60% or less of the gait phase of the left leg. Substantially all of the third stop period is included in the stance phase of the left leg. In the example illustrated in FIG. 27A and FIG. 27B, the drive control unit 122 stops generating a tension in the first wire 110a1 and the second wire 110a2 and reduces the tension to zero in the third stop period immediately after assistance for extension of the left leg is finished, that is, at a timing of 20% of the gait phase of the left leg.

Further, the drive control unit 122 stops generating a tension in the third wire 110a3 and the fourth wire 110a4 at any timing during a fourth stop period in the gait phase of the right leg starting in an end period of the fourth period and ending in a start period of the third period. The drive control unit 122 reduces the tension of the third wire 110a3 and the fourth wire 110a4 to less than the second threshold value and to zero in the fourth stop period. After the fourth stop period, the drive control unit 122 does not generate a tension greater than or equal to the second threshold value in the third wire 110a3 and the fourth wire 110a4 in and after the third period and the eighth period. In this way, the drive control unit 122 stops assistance with the third wire 110a3 and the fourth wire 110a4 in the fourth stop period. In the example illustrated in FIG. 27A and FIG. 27B, the drive control unit 122 reduces the tensions of the third wire 110a3 and the fourth wire 110a4 to zero at the same timing. However, the timing of stopping generating a tension in the third wire 110a3 and the timing of stopping generating a tension in the fourth wire 110a4 may be arranged in any order if both timings fall within the third stop period.

The end period of the fourth period includes a period up to a time point that occurs at about 5% before the timing at which the fourth period ends. An example of the end period of the fourth period is a period of 5% or more and 25% or less of the gait phase of the right leg. The start period of the third period includes a period up to a time point that progresses by about 5% from the timing at which the third period starts in the gait phase of the right leg. An example of the start period of the third period is a period of 35% or more and 60% or less of the gait phase of the right leg. Thus, the fourth stop period may include a period of 5% or more and 60% or less of the gait phase of the right leg. Substantially all of the fourth stop period is included in the stance phase of the right leg. In the example illustrated in FIG. 27A and FIG. 27B, the drive control unit 122 stops generating a tension in the third wire 110a3 and the fourth wire 110a4 and reduces the tension to zero in the fourth stop period immediately after assistance for extension of the right leg is finished, that is, at a timing of 20% of the gait phase of the right leg.

As described above, the assistance apparatus 100 stops generating a tension in the first wire 110a1 and the second wire 110a2 for the left leg in a period between a period during which flexion is substantially assisted and a period during which extension is substantially assisted. The assistance apparatus 100 stops generating a tension in the third wire 110a3 and the fourth wire 110a4 for the right leg in a period from a period during which flexion is substantially assisted and a period during which extension is substantially assisted. That is, the assistance apparatus 100 stops assisting the left and right legs when an assistance force for flexion and extension, which is perceived by the user through bodily sensations, is not generated. This can prevent the user from feeling uncomfortable with the left and right legs when assistance of each of the left and right legs is stopped, and can prevent instability of the left leg and the right leg due to lack of assistance for flexion.

In addition, the third stop period and the fourth stop period do not overlap mostly. Accordingly, the assistance apparatus 100 stops assisting the left leg and stops assisting the right leg sequentially with a time difference. In the example illustrated in FIG. 27A and FIG. 27B, the third stop period occurs earlier than the fourth stop period. Alternatively, the fourth stop period may occur earlier than the third stop period. In this case, the assistance apparatus 100 stops assisting the right leg and thereafter stops assisting the left leg.

3-3. Modification of Assistance Operation of Assistance Apparatus

Figure 28:
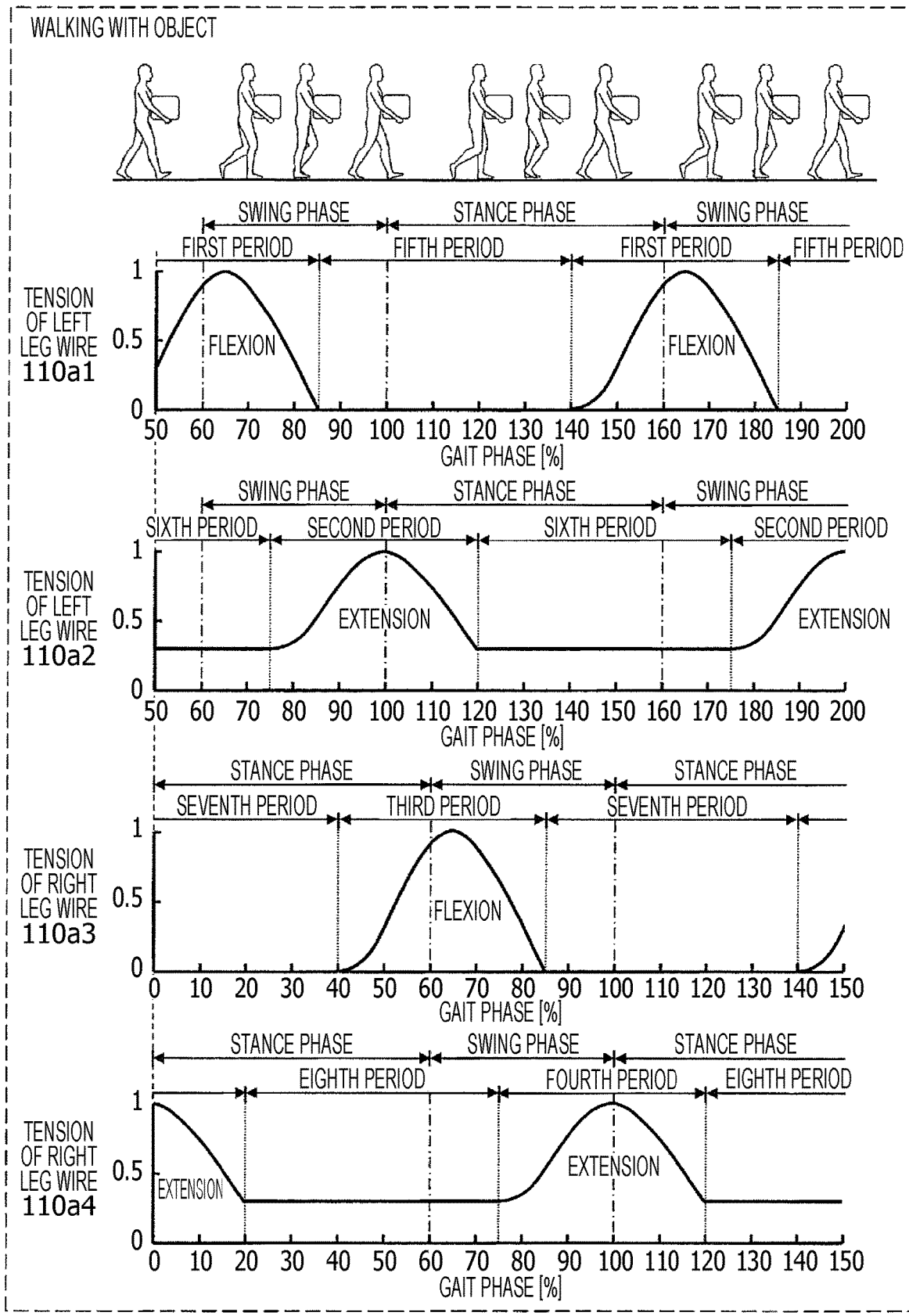
FIG. 28 is a diagram illustrating a modification of the operation of the assistance apparatus according to the embodiment for assisting a user in walking forward while carrying an object.

A modification of the assistance operation of the assistance apparatus 100 will be described. In this modification, when assisting a user in walking while carrying an object, the assistance apparatus 100 operates in a way described below. Specifically, the assistance apparatus 100 increases the duration of assistance using the wires 110a2 and 110a4 in the back part of the body of the user, compared with that in the example illustrated in FIG. 25. For example, FIG. 28 illustrates a modification of the operation of the assistance apparatus 100 for assisting a user in walking forward while carrying an object. FIG. 28 illustrates an example in which the assistance apparatus 100 assists both flexion and extension of the left and right legs of the user. The assistance apparatus 100 produces a wire tension while changing the wire tension, with a maximum tension being 100 N.

When assisting flexion while a user is walking forward, the assistance apparatus 100 generates wire tensions in the wire 110a1 of the left leg and the wire 110a3 of the right leg in a way similar to that in the example illustrated in FIG. 25.

When assisting extension of the left leg, for example, the assistance apparatus 100 continuously generates a tension in the wire 110a2 during the entirety of a second period, which is a period of 75% or more and 120% or less of the gait phase of the left leg. Then, the assistance apparatus 100 generates a wire tension greater than or equal to a first threshold value in the wire 110a2 during at least a portion of the second period. Further, the assistance apparatus 100 continuously generates a tension greater than or equal to a second threshold value and less than or equal to a third threshold value in the wire 110a2 during the entirety of a sixth period, which is a period other than the second period. The tension of the wire 110a2 in the sixth period is greater than the tension of the wire 110a1 in the fifth period and is greater than the tension of the wire 110a2 in the sixth period in the example illustrated in FIG. 25. Then, the assistance apparatus 100 continuously generates a tension, which is greater than the wire tension in the sixth period, in the wire 110a2 during the entirety of the second period. Thus, the assistance apparatus 100 continuously generates a tension greater than or equal to the second threshold value in the wire 110a2 during an entire period including the second period and the sixth period. The third threshold value is a value less than the maximum wire tension. The second threshold value is the same as the second threshold value described above in the embodiment. The third threshold value is given by, for example, an expression of maximum tension×0.6.

When assisting extension of the right leg, for example, the assistance apparatus 100 continuously generates a tension in the wire 110a4 during the entirety of a fourth period, which is a period of 75% or more and 120% or less of the gait phase of the right leg. Then, the assistance apparatus 100 generates a wire tension greater than or equal to the first threshold value in the wire 110a4 during at least a portion of the fourth period. Further, the assistance apparatus 100 continuously generates a tension greater than or equal to the second threshold value and less than or equal to the third threshold value in the wire 110a4 during the entirety of an eighth period, which is a period other than the fourth period. The tension of the wire 110a4 in the eighth period is greater than the tension of the wire 110a3 in the seventh period and is greater than the tension of the wire 110a4 in the eighth period in the example illustrated in FIG. 25. Then, the assistance apparatus 100 continuously generates a tension, which is greater than the wire tension in the eighth period, in the wire 110a4 during the entirety of the fourth period. Thus, the assistance apparatus 100 continuously generates a tension greater than or equal to the second threshold value in the wire 110a4 during an entire period including the fourth period and the eighth period.

As described above, a tension greater than or equal to the second threshold value is generated in the wires 110a2 and 110a4, which are located on or above the back part of the body of the user, during the entirety of a period over which the assistance apparatus 100 provides assistance. Thus, the user is subjected to the action such that the left and right legs are pulled backward all the time during walking. When the user is holding an object in the front part of the body, the center of gravity of the body of the user tends to be moved forward. Thus, the user, who is holding an object in the front part of the body, is subjected to the action such that the tensions of the wires 110a2 and 110a4 cause the user to walk forward with the center of gravity of the body being kept at the center of gravity position in the upright posture. This enables the user to walk with a stable posture. Accordingly, the user is able to transport an object with comfort. In the fifth period, the tension of the wire 110a1 for assisting flexion of the left leg is small, and thus the action exerted by the tension of the wire 110a2 is achieved while being less affected by the tension of the wire 110a1. In the seventh period, the tension of the wire 110a3 for assisting flexion of the right leg is small, and thus the action exerted by the tension of the wire 110a4 is achieved while being less affected by the tension of the wire 110a3.

Figure 29A:
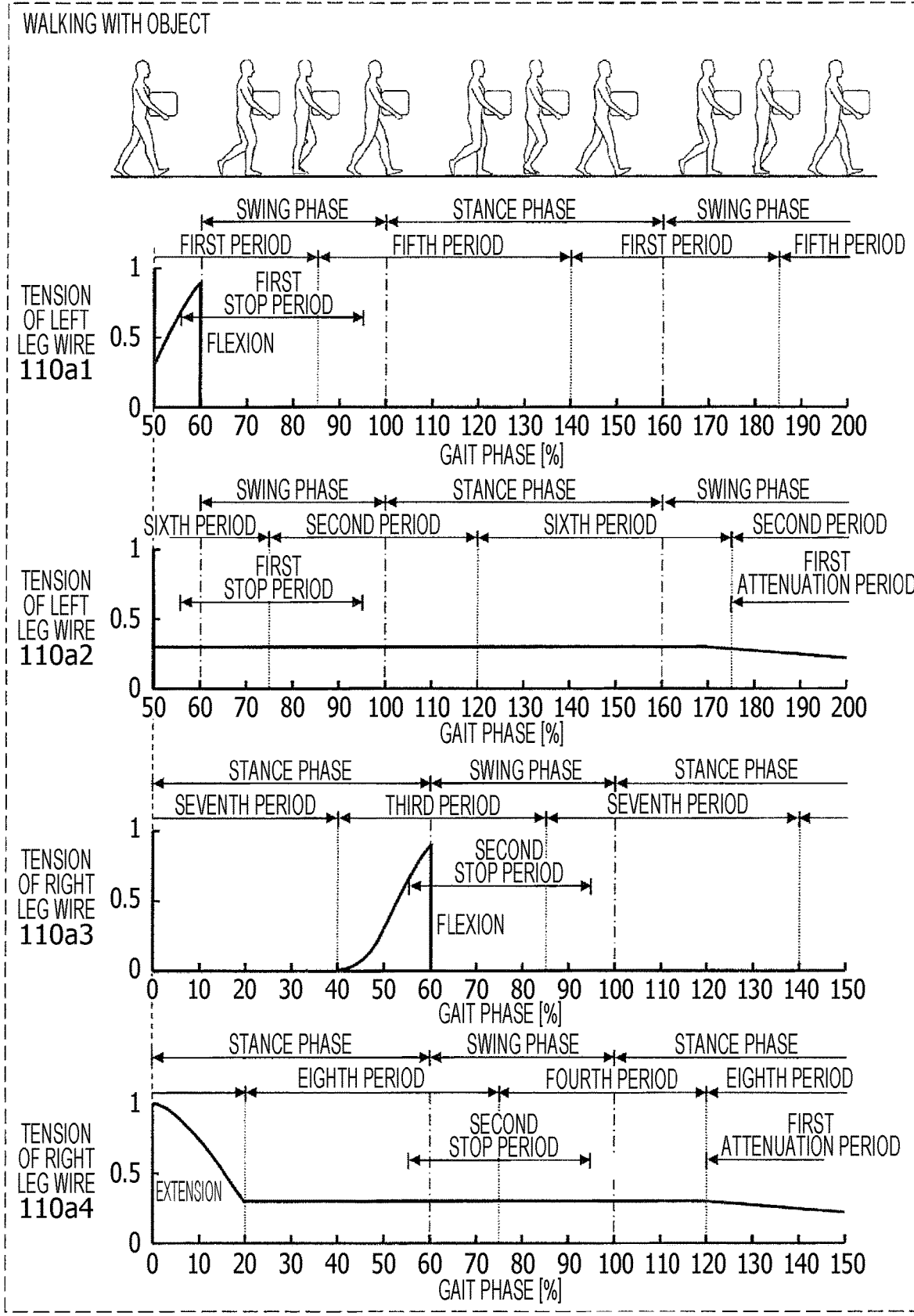
FIG. 29A is a diagram illustrating an example operation of the assistance apparatus for stopping assistance in a state illustrated in FIG. 28.
Figure 29B:
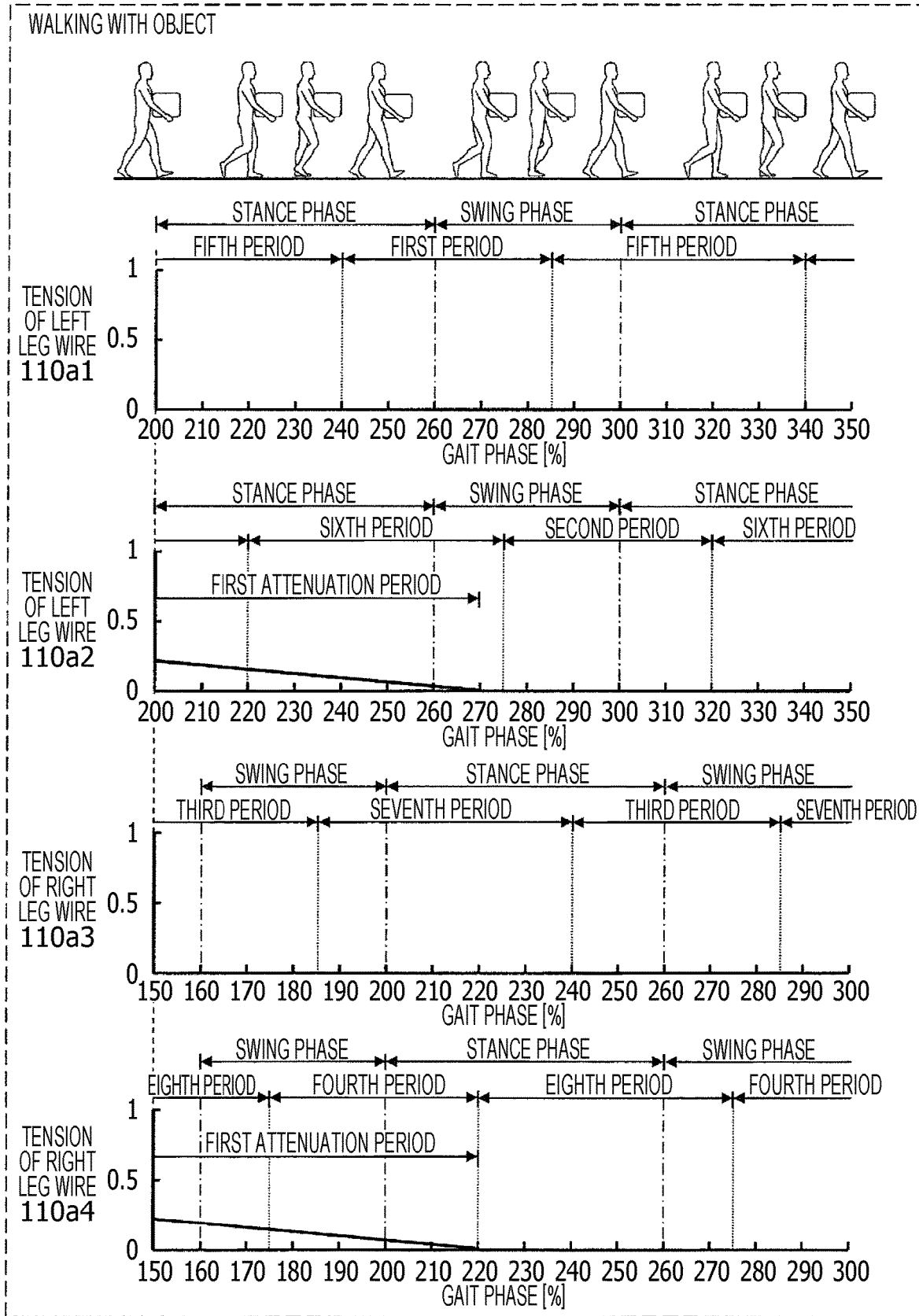
FIG. 29B is a diagram illustrating an example operation of the assistance apparatus for stopping assistance in the state illustrated in FIG. 28.

In this modification, furthermore, the assistance apparatus 100 stops assistance in a way described below. Also in this modification, the drive control unit 122 stops assisting the left leg and stops assisting the right leg at shifted timings. Specifically, when assistance of the left leg is stopped and thereafter assistance of the right leg is stopped, for example, as illustrated in FIG. 29A and FIG. 29B, the drive control unit 122 stops assisting flexion of the left leg and the right leg in the first stop period and the second stop period. FIG. 29A and FIG. 29B are diagrams illustrating an example operation of the assistance apparatus 100 for stopping assistance in the state illustrated in FIG. 28, and illustrates a continuous operation of the assistance apparatus 100.

The drive control unit 122 stops generating a tension in the first wire 110a1 at any timing during the first stop period in the gait phase of the left leg and, at and after the timing, keeps the tension of the second wire 110a2 greater than or equal to the second threshold value and less than or equal to the third threshold value. In this modification, the drive control unit 122 does not change the tension of the second wire 110a2 before and after the timing of stopping generating a tension in the first wire 110a1. After the first stop period, the drive control unit 122 keeps the tension of the second wire 110a2 at a substantially constant tension greater than or equal to the second threshold value and less than or equal to the third threshold value in and after the second period. Thus, the drive control unit 122 stops assisting flexion using the first wire 110a1 for walking during the first stop period and, in and after the first stop period, stops assisting extension using the second wire 110a2 for walking, whereas continuing assistance for extension to keep the center of gravity of the body of the user at a position in the upright posture.

Further, the drive control unit 122 stops generating a tension in the third wire 110a3 at any timing during the second stop period in the gait phase of the right leg and, at and after the timing, keeps the tension of the fourth wire 110a4 greater than or equal to the second threshold value and less than or equal to the third threshold value. In this modification, the drive control unit 122 does not change the tension of the fourth wire 110a4 before and after the timing of stopping generating a tension in the third wire 110a3. After the second stop period, the drive control unit 122 keeps the tension of the fourth wire 110a4 at a substantially constant tension greater than or equal to the second threshold value and less than or equal to the third threshold value in and after the fourth period. Thus, the drive control unit 122 stops assisting flexion using the third wire 110a3 for walking during the second stop period and, in and after the second stop period, stops assisting extension using the fourth wire 110a4 for walking, whereas continuing assistance for extension to keep the center of gravity of the body of the user at a position in the upright posture.

Further, the drive control unit 122 starts decreasing the tensions of the second wire 110a2 and the fourth wire 110a4 at the same timing on and after the timing of stopping generating a tension in the third wire 110a3. Further, the drive control unit 122 decreases the tensions of the second wire 110a2 and the fourth wire 110a4 to zero in an entire first attenuation period, which starts at the timing described above. In this case, likewise, the drive control unit 122 progressively decreases the tensions of the second wire 110a2 and the fourth wire 110a4 in accordance with the progression of the gait phase. In this modification, the rates of decrease in the tensions of the second wire 110a2 and the fourth wire 110a4 over the gait phases may be the same, and, for example, the tensions of the second wire 110a2 and the fourth wire 110a4 on the vertical axis may each exhibit a straight line, a concave curve, or a convex curve with respect to the gait phase on the horizontal axis. The drive control unit 122 may progressively decrease the tensions of the second wire 110a2 and the fourth wire 110a4 with time, rather than in accordance with the progression of the gait phase.

The tensions of the second wire 110a2 and the fourth wire 110a4 may be started to decrease at any timing at or after the timing of stopping generating tensions in both the first wire 110a1 and the third wire 110a3. For example, in the example illustrated in FIG. 29A and FIG. 29B, the tensions of the second wire 110a2 and the fourth wire 110a4 may be started to decrease at a later timing, namely, the timing of stopping generating a tension in the third wire 110a3. Alternatively, the tensions of the second wire 110a2 and the fourth wire 110a4 may be started to decrease at a timing when both the second period subsequent to the first stop period and the fourth period subsequent to the second stop period have passed. In this case, in the example illustrated in FIG. 29A and FIG. 29B, the tensions of the second wire 110a2 and the fourth wire 110a4 may be started to decrease at a timing when the later period, namely, the fourth period, has passed. In the latter case, a time interval between the timing at which assistance with the first wire 110a1 and the third wire 110a3 is stopped and the timing at which the tensions of the second wire 110a2 and the fourth wire 110a4 are started to decrease can reduce the load imposed on the left and right legs of the user.

Further, in the example illustrated in FIG. 29A and FIG. 29B, the first attenuation period accounts for 100% of the gait phases of the left and right legs. Preferably, the first attenuation period is a period of 50% or more and 200% or less of each of the gait phases of the left and right legs.

As described above, after stopping assisting flexion and extension for walking, the assistance apparatus 100 progressively decreases and stops assistance for extension of the left and right legs for keeping the center of gravity of the body of the user, who is carrying an object, at a position in the upright posture. The assistance apparatus 100 sequentially stops the assistance operations for the left and right legs of the user to prevent a rapid increase in the load imposed on the user and to reduce the load on the user. In addition, the assistance apparatus 100 decreases assistance for extension of the left and right legs for keeping the center of gravity of the body of the user at a position in the upright posture at the same timing in a similar manner. Thus, the balance between the movements of the left and right legs of the user can be maintained. In the example illustrated in FIG. 29A and FIG. 29B, the first stop period occurs earlier than the second stop period. Alternatively, the second stop period may occur earlier than the first stop period. In this case, the assistance apparatus 100 stops assisting flexion of the right leg for walking and thereafter stops assisting flexion of the left leg for walking. After that, the assistance apparatus 100 stops assistance for extension of the left and right legs for keeping the center of gravity of the body of the user at a position in the upright posture in a similar manner.

Figure 30A:
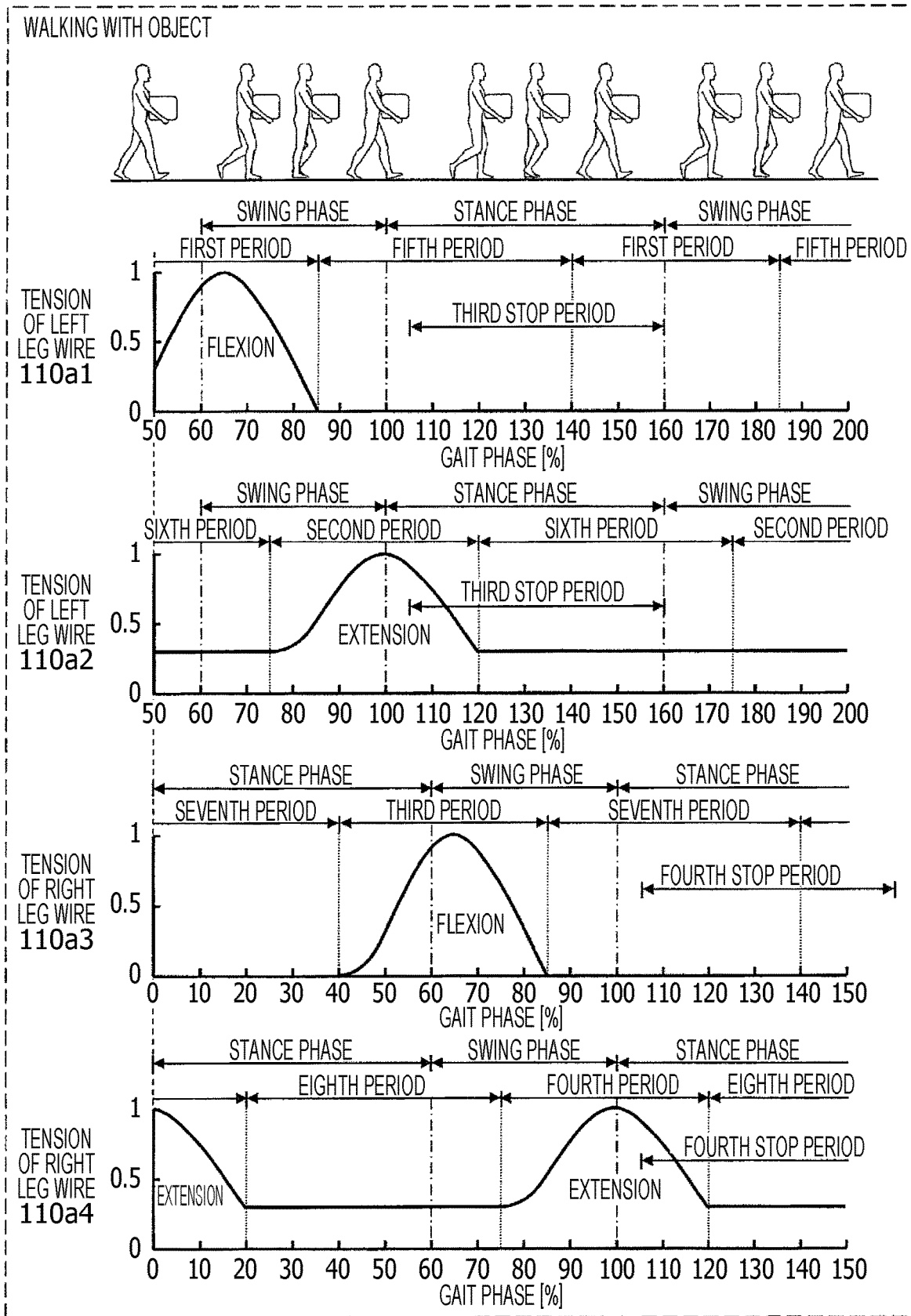
FIG. 30A is a diagram illustrating another example operation of the assistance apparatus for stopping assistance in the state illustrated in FIG. 28.
Figure 30B:
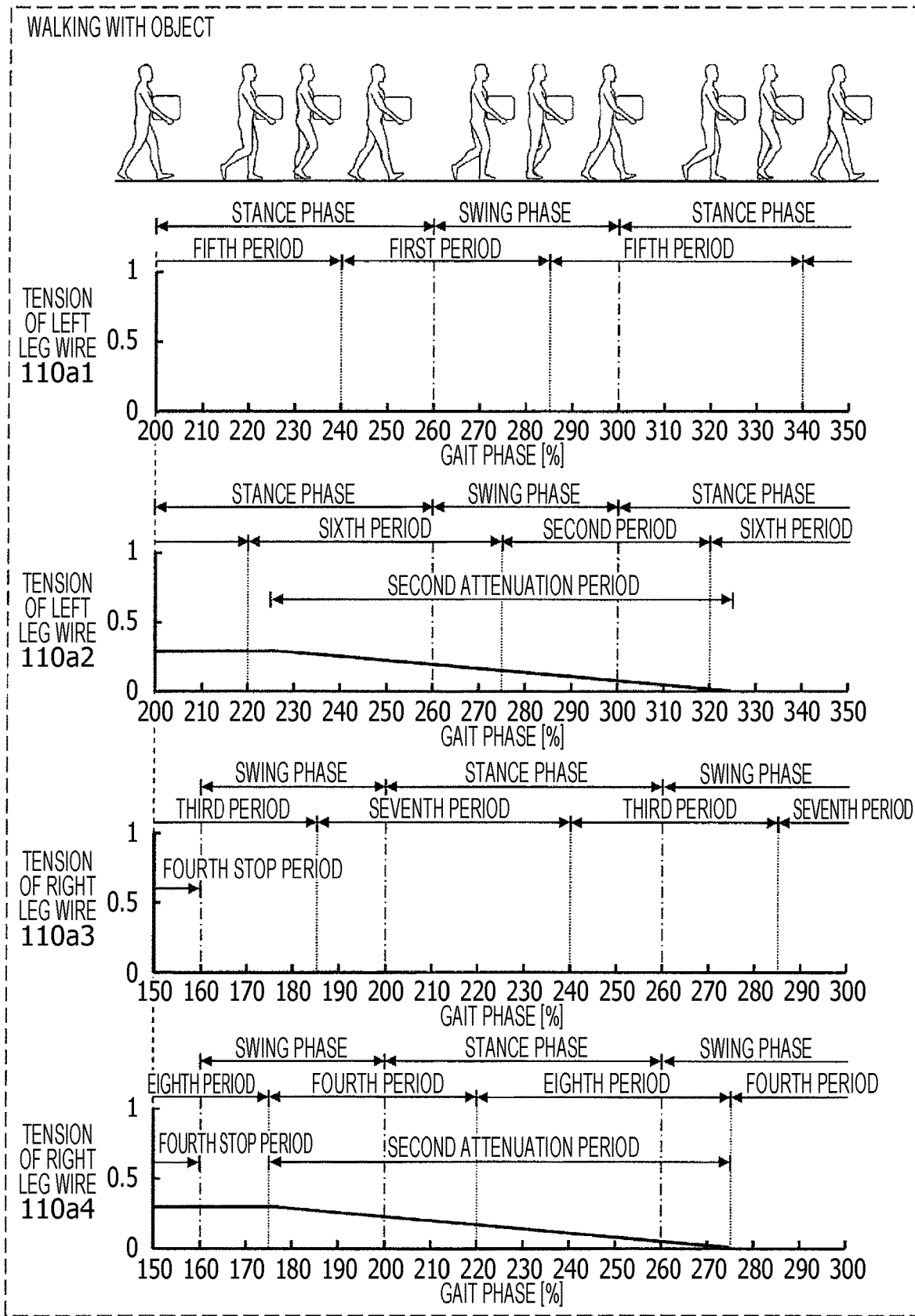
FIG. 30B is a diagram illustrating another example operation of the assistance apparatus for stopping assistance in the state illustrated in FIG. 28.

In addition, the assistance apparatus 100 may stop assisting flexion of the left leg and the right leg in the third stop period and the fourth stop period. For example, when assistance of the left leg is stopped and thereafter assistance of the right leg is stopped, for example, the drive control unit 122 controls wire tensions in a way illustrated in FIG. 30A and FIG. 30B. FIG. 30A and FIG. 30B are diagrams illustrating another example operation of the assistance apparatus 100 for stopping assistance in the state illustrated in FIG. 28, and illustrates a continuous operation of the assistance apparatus 100.

The drive control unit 122 stops generating a tension in the first wire 110a1 at any timing during the third stop period in the gait phase of the left leg and, at and after the timing, keeps the tension of the second wire 110a2 greater than or equal to the second threshold value and less than or equal to the third threshold value. In FIG. 30A and FIG. 30B, this timing is the same as that in FIG. 27A and FIG. 27B. After the third stop period, the drive control unit 122 keeps the tension of the second wire 110a2 at a substantially constant tension greater than or equal to the second threshold value and less than or equal to the third threshold value in and after the sixth period. Accordingly, the drive control unit 122 stops assisting flexion using the first wire 110a1 for walking during the third stop period and, in and after the third stop period, stops assisting extension using the second wire 110a2 for walking, whereas continuing assistance for extension to keep the center of gravity of the body of the user at a position in the upright posture.

Further, the drive control unit 122 stops generating a tension in the third wire 110a3 at any timing during the fourth stop period in the gait phase of the right leg and, at and after the timing, keeps the tension of the fourth wire 110a4 greater than or equal to the second threshold value and less than or equal to the third threshold value. In FIG. 30A and FIG. 30B, this timing is the same as that in FIG. 27A and FIG. 27B. After the fourth stop period, the drive control unit 122 keeps the tension of the fourth wire 110a4 at a substantially constant tension greater than or equal to the second threshold value and less than or equal to the third threshold value in and after the eighth period. Accordingly, the drive control unit 122 stops assisting flexion using the third wire 110a3 for walking during the fourth stop period and, in and after the fourth stop period, stops assisting extension using the fourth wire 110a4 for walking, whereas continuing assistance for extension to keep the center of gravity of the body of the user at a position in the upright posture.

Further, the drive control unit 122 starts decreasing the tensions of the second wire 110a2 and the fourth wire 110a4 at the same timing on and after the timing of stopping generating a tension in the third wire 110a3. Further, the drive control unit 122 decreases the tensions of the second wire 110a2 and the fourth wire 110a4 to zero in an entire second attenuation period, which starts at the timing described above. In this case, likewise, the drive control unit 122 progressively decreases the tensions of the second wire 110a2 and the fourth wire 110a4 in accordance with the progression of the gait phase. Also in this case, the rates of decrease in the tensions of the second wire 110a2 and the fourth wire 110a4 over the gait phases may be the same, and, for example, the tensions of the second wire 110a2 and the fourth wire 110a4 on the vertical axis may each exhibit a straight line, a concave curve, or a convex curve with respect to the gait phase on the horizontal axis. The drive control unit 122 may progressively decrease the tensions of the second wire 110a2 and the fourth wire 110a4 with time, rather than in accordance with the progression of the gait phase.

The tensions of the second wire 110a2 and the fourth wire 110a4 may be started to decrease at any timing at or after the timing of stopping generating tensions in both the first wire 110a1 and the third wire 110a3. For example, in the example illustrated in FIG. 30A and FIG. 30B, the tensions of the second wire 110a2 and the fourth wire 110a4 may be started to decrease at a later timing, namely, the timing of stopping generating a tension in the third wire 110a3. Alternatively, the tensions of the second wire 110a2 and the fourth wire 110a4 may be started to decrease at a timing when both the sixth period subsequent to the third stop period and the eighth period subsequent to the fourth stop period have passed. In this case, in the example illustrated in FIG. 30A and FIG. 30B, the tensions of the second wire 110a2 and the fourth wire 110a4 may be started to decrease at a timing when the later period, namely, the eighth period, has passed. In the latter case, a time interval between the timing at which assistance with the first wire 110a1 and the third wire 110a3 is stopped and the timing at which the tensions of the second wire 110a2 and the fourth wire 110a4 are started to decrease can reduce the load imposed on the left and right legs of the user.

Further, in the example illustrated in FIG. 30A and FIG. 30B, the second attenuation period accounts for 100% of the gait phases of the left and right legs. Preferably, the second attenuation period is a period of 50% or more and 200% or less of each of the gait phases of the left and right legs and may be equal to or different from the first attenuation period.

As described above, the assistance apparatus 100 achieves advantages similar to those when stopping assisting flexion of the left leg and the right leg in the first stop period and the second stop period. In the example illustrated in FIG. 30A and FIG. 30B, the third stop period occurs earlier than the fourth stop period. Alternatively, the fourth stop period may occur earlier than the third stop period. In this case, the assistance apparatus 100 stops assisting flexion of the right leg for walking and thereafter stops assisting flexion of the left leg for walking. After that, the assistance apparatus 100 stops assistance for extension for keeping the postures of the left and right legs in a similar manner.

3-4. Other Modifications of Assistance Operation of Assistance Apparatus

The assistance apparatus 100 may perform an operation according to the modification so as to prevent a user from stumbling. By preventing a user from stumbling, the assistance apparatus 100 can prevent the user from falling. In this case, for example, the assistance apparatus 100 generates substantially no wire tension, that is, generates a wire tension less than the second threshold value, in the wire 110a2 for assisting extension of the left leg during a portion of the sixth period corresponding to the swing phase of the left leg within the gait phase of the left leg. The portion of the sixth period is, for example, a period of more than 60% and less than 75% of the gait phase of the left leg. Likewise, the assistance apparatus 100 makes the tension of the wire 110a4 for assisting extension of the right leg less than the second threshold value over a portion of the eighth period corresponding to the swing phase of the right leg within the gait phase of the right leg. The portion of the eighth period is, for example, a period of more than 60% and less than 75% of the gait phase of the right leg. This enables the user to easily raise a leg off the ground and can prevent the user from catching the toe and tripping on the ground, level differences, or the like. In the case described above, the assistance apparatus 100 may also apply the operation for stopping assistance according to the embodiment and the operation for stopping assistance according to the modification.

In addition, for example, the assistance apparatus 100 continuously generates a wire tension greater than or equal to the second threshold value and less than or equal to the third threshold value in the wire 110a1 for assisting flexion of the left leg during the entirety of the fifth period in the gait phase of the left leg. The tension of the wire 110a1 in the fifth period is greater than the tension of the wire 110a1 in the fifth period in the example illustrated in FIG. 25. This enables the user to easily raise the left leg in the shift to flexion in the first period. Further, the assistance apparatus 100 continuously generates a wire tension greater than or equal to the second threshold value and less than or equal to the third threshold value in the wire 110a3 for assisting flexion of the right leg during the entirety of the seventh period in the gait phase of the right leg. The tension of the wire 110a3 in the seventh period is greater than the tension of the wire 110a3 in the seventh period in the example illustrated in FIG. 25. This enables the user to easily raise the right leg in the shift to flexion in the third period. Thus, the assistance apparatus 100 enables the user to easily raise a leg for flexion and can prevent the user from catching the toe and stumbling. In the case described above, the assistance apparatus 100 may also apply the operation for stopping assistance according to the embodiment and the operation for stopping assistance according to the modification.

In addition, the assistance apparatus 100 may not only assist a user in walking forward while carrying an object but also assist a stationary user in lifting an object. In this case, the assistance apparatus 100 does not assist flexion of the left and right legs, but assists extension of the left and right legs. When lifting an object in front of the user, the user shifts from a stooping or crouching position to an upright position. The user, who receives an assistance force for extending both legs from the assistance apparatus 100, can more easily achieve the shift from the stooping or crouching position to the upright position.

During assistance, the assistance apparatus 100 generates tensions greater than a fourth threshold value in the wires 110a2 and 110a4 at the same timing. The fourth threshold value is a larger value than the first threshold value and the second threshold value. The fourth threshold value is, for example, 60 N. The tensions of the wires 110a2 and 110a4 for assisting the user in lifting an object may be greater than the tensions of the wires 110a2 and 110a4 for assisting the user in walking forward while carrying an object. The tensions of the wires 110a2 and 110a4 may be generated at timings that are shifted from each other. The assistance apparatus 100 described above can assist a user in a series of motions from lifting an object to transporting the object.

In the respective operations of the assistance apparatuses 100 and 200 according to the embodiment and the modification, the same input profile of wire tension and the same maximum tension are set for all the wires 110 for assisting flexion and extension. However, the present disclosure is not limited to the embodiment and the modification described above. Since the moment arms of the hip joints and the lengths of the legs differ from one user to another, the assistance torque exerted on the hip joint differs depending on the user even when the same tension is applied to the same wire. The assistance torque is determined by an expression of wire tension×moment arm. Thus, different tensions may be applied to the wires 110 in accordance with the user. A fatter user has a larger moment arm of the hip joint than a thinner user. Thus, for example, the maximum wire tension may be set to 60 N for a fat user with a girth of 100 cm or more, whereas the maximum wire tension may be set to 120 N for a thin user with a girth or 70 cm or less. This may make assistance torques exerted on a fat user and a thin user equivalent.

In addition, the wire tension may change in accordance with the lengths of the legs of the user. In assistance for flexion and extension, since a vertical, or upward and downward, force component of wire tension is more largely exerted on a user with longer legs, the wire tension for a user with longer legs may be reduced. Adjusting the wire tension for each user in accordance with the body type and the leg length enables a comfortable assistance torque to be applied to each user.

In addition, the wire tensions on the front and back sides of the legs of the user are set to the same value. However, the present disclosure is not limited to the embodiment and the modification described above. For example, the tensions of the wires located on the front side of the legs may be greater than the tensions of the wires located on the back side of the legs. Since the wires on the back side pass through the buttocks of the user, the moment arm on the back side of the body of the user is greater than that on the front side of the body of the user. Accordingly, the assistance torque exerted on the hip joints on the back side of the body of the user is greater than that on the front side of the body of the user. Thus, by increasing the tension of the wires on the front side, the assistance apparatuses 100 and 200 can assist flexion and extension of the user on the front and back sides in a well-balanced manner.

The periods during which wire tensions are generated in the wires 110 for assistance for flexion and extension are equal to each other. However, the present disclosure is not limited to the embodiment and the modification described above. For example, in the example illustrated in FIG. 25, the period during which a wire tension for assisting flexion is generated and the period during which a wire tension for assisting extension of the same leg is generated overlap. To reduce the overlap period, the length of either of the periods may be reduced. In particular, the periods may be adjusted such that the period in which a wire tension greater than or equal to the first threshold value is generated during assistance for flexion does not overlap the period in which a wire tension greater than or equal to the first threshold value is generated during assistance for extension. This also applies to the examples illustrated in FIG. 26 to FIG. 30B. This prevents the user from being confused by the simultaneous feeling of assistance for flexion and assistance for extension. The relationship between the period during which a wire tension for assisting flexion is generated and the period during which a wire tension for assisting extension is generated may be determined in accordance with the flexion and extension ability of the user.

In FIG. 25 to FIG. 30B, the waveforms of the input profiles of wire tensions are convex curve. However, the present disclosure is not limited to the illustrated examples. The waveforms of the input profiles illustrated in FIG. 25 to FIG. 30B are waveforms obtained through experiments, which are waveforms that allow users to feel effective and comfortable when enjoying the benefits of assistance provided by the assistance apparatus 100. The input profiles of the wire tensions may be each created using, for example, a rectangular waveform, a trapezoidal waveform, a triangular waveform, a Gaussian waveform, or the like. When a rectangular waveform is used, the assistance apparatus 100 continuously generates a maximum tension during an entire period over which a wire tension is generated. When a trapezoidal waveform is used, the assistance apparatus 100 continuously generates a maximum tension during an entire period over which a wire tension is generated, except the initial and terminal periods. When each input profile is created using a waveform that is quadrangle such as a rectangular waveform and a trapezoidal waveform, a steep rise or a steep fall of the wire tension may occur. Such a change in tension may cause a user to feel uncomfortable during assistance. Thus, for example, when the waveform of each input profile is triangular, a rise of the wire tension to the maximum tension may be changed to a gentler one, with the wire tension changing gradually. Accordingly, the assistance apparatus 100 can carefully assist movements of the legs of the user, resulting in a reduction in the risk of falling of the user due to a steep change in wire tension.

In actual human walking, flexion and extension torques produced by the legs smoothly and continuously change. Thus, the waveform of each input profile may be implemented as a Gaussian waveform. The Gaussian waveform may be a waveform created by, for example, adding together, or superposing, Gaussian functions by using a Gaussian function given by Equation (1) below. In this case, among superposition methods of Gaussian functions, a superposition method that is closest to the waveform of a torque of the legs in actual human walking is found and applied to the generation of a waveform of an input profile. Finding such a method is also referred to as Gaussian fitting. Accordingly, assistance torques can be applied to realize walking similar to actual human walking, and more natural assistance can be achieved.

$$f(x) = \frac{1}{\sqrt{2\pi}\,\sigma} \exp\left\{-\frac{(x-\mu)^2}{2\sigma^2}\right\} \quad (1)$$

Specifically, a Gaussian function has a pair of variables μ and σ (also referred to as parameters), and the waveform of the Gaussian function depends on the two parameters. The time indicating a peak of a wave of the Gaussian function depends on the variable μ, and the width of the wave of the Gaussian function depends on the variable σ. Thus, various Gaussian functions may be generated by using various combinations of values of the two parameters.

A function obtained by multiplying an amplitude of a torque generated in a leg during human walking by a Gaussian function forms a waveform that shows time (in seconds) on the horizontal axis and torque (in Nm) on the vertical axis. Examples of the amplitude include a maximum torque of a leg during human walking, and the amplitude is, for example, 20 Nm. Gaussian functions are superposed to find a superposition method that is closest to the torque-time waveform of the leg during actual human walking. At this time, Gaussian fitting is performed on actual human gait data by using n Gaussian functions $f_1(x)$, $f_2(x)$, . . . , and $f_n(x)$ having various values of the two parameters μ and σ to obtain Gaussian functions. The obtained Gaussian functions are further superposed to obtain a new Gaussian function. By adjusting the two parameters μ and σ of the new Gaussian function, an input profile of a wire tension can be created.

Further, the assistance apparatus 100 may change the maximum tensions to be generated in the wires 110 in accordance with the time of year when the user wears the assistance apparatus 100. For example, in summer when the user wears light clothes, the user's moment arm is shorter than that in winter when the user wears thick clothes. Accordingly, even when the assistance apparatus 100 applies the same tension to the wires 110, the torques exerted on the legs of the user in summer are smaller than those in winter. Thus, for example, the assistance apparatus 100 may increase the tension to be applied to each of the wires 110 in summer to, for example, 1.2 times that in winter.

The operation of the assistance apparatus 200 according to the modification illustrated in FIG. 13 to FIG. 21 is also similar to that of the assistance apparatus 100 according to the embodiment. For the operations described above, the wire tension control for the first wire 110a1 and the wire tension control for the fifth wire 110a5 of the assistance apparatus 200 are similar to the wire tension control for the wire 110a1 of the assistance apparatus 100. The wire tension control for the second wire 110a2 and the wire tension control for the sixth wire 110a6 of the assistance apparatus 200 are similar to the wire tension control for the wire 110a2 of the assistance apparatus 100. The wire tension control for the third wire 110a3 and the wire tension control for the seventh wire 110a7 of the assistance apparatus 200 are similar to the wire tension control for the wire 110a3 of the assistance apparatus 100. The wire tension control for the fourth wire 110a4 and the wire tension control for the eighth wire 110a8 of the assistance apparatus 200 are similar to the wire tension control for the wire 110a4 of the assistance apparatus 100.

When assisting flexion or extension, the assistance apparatus 200 generates tensions in two wires of the same leg at the same timing. Thus, the maximum tension to be generated in the first wire 110a1 and the maximum tension to be generated in the fifth wire 110a5 of the assistance apparatus 200 may be different from the maximum tension to be generated in the wire 110a1 of the assistance apparatus 100 and may be smaller than the maximum tension to be generated in the wire 110a1 of the assistance apparatus 100, for example. The maximum tension to be generated in the second wire 110a2 and the maximum tension to be generated in the sixth wire 110a6 of the assistance apparatus 200 may be different from the maximum tension to be generated in the wire 110a2 of the assistance apparatus 100 and may be smaller than the maximum tension to be generated in the wire 110a2 of the assistance apparatus 100, for example. The maximum tension to be generated in the third wire 110a3 and the maximum tension to be generated in the seventh wire 110a7 of the assistance apparatus 200 may be different from the maximum tension to be generated in the wire 110a3 of the assistance apparatus 100 and may be smaller than the maximum tension to be generated in the wire 110a3 of the assistance apparatus 100, for example. The maximum tension to be generated in the fourth wire 110a4 and the maximum tension to be generated in the eighth wire 110a8 of the assistance apparatus 200 may be different from the maximum tension to be generated in the wire 110a4 of the assistance apparatus 100 and may be smaller than the maximum tension to be generated in the wire 110a4 of the assistance apparatus 100, for example.

The relationship between the maximum tension to be generated in the first wire 110a1 and the maximum tension to be generated in the fifth wire 110a5 of the assistance apparatus 200 and the maximum tension to be generated in the wire 110a1 of the assistance apparatus 100 changes in accordance with the angle between the direction in which the wire 110a1 of the assistance apparatus 100 extends and the direction in which the first wire 110a1 of the assistance apparatus 200 extends and in accordance with the angle between the direction in which the wire 110a1 of the assistance apparatus 100 extends and the direction in which the fifth wire 110a5 of the assistance apparatus 200 extends, and can be determined in accordance with the angles. The relationship between the maximum tension to be generated in the second wire 110a2 and the maximum tension to be generated in the sixth wire 110a6 of the assistance apparatus 200 and the maximum tension to be generated in the wire 110a2 of the assistance apparatus 100 changes in accordance with the angle between the direction in which the wire 110a2 of the assistance apparatus 100 extends and the direction in which the second wire 110a2 of the assistance apparatus 200 extends and in accordance with the angle between the direction in which the wire 110a2 of the assistance apparatus 100 extends and the direction in which the sixth wire 110a6 of the assistance apparatus 200 extends, and can be determined in accordance with the angles. The relationship between the maximum tension to be generated in the third wire 110a3 and the maximum tension to be generated in the seventh wire 110a7 of the assistance apparatus 200 and the maximum tension to be generated in the wire 110a3 of the assistance apparatus 100 changes in accordance with the angle between the direction in which the wire 110a3 of the assistance apparatus 100 extends and the direction in which the third wire 110a3 of the assistance apparatus 200 extends and in accordance with the angle between the direction in which the wire 110a3 of the assistance apparatus 100 extends and the direction in which the seventh wire 110a7 of the assistance apparatus 200 extends, and can be determined in accordance with the angles. The relationship between the maximum tension to be generated in the fourth wire 110a4 and the maximum tension to be generated in the eighth wire 110a8 of the assistance apparatus 200 and the maximum tension to be generated in the wire 110a4 of the assistance apparatus 100 changes in accordance with the angle between the direction in which the wire 110a4 of the assistance apparatus 100 extends and the direction in which the fourth wire 110a4 of the assistance apparatus 200 extends and in accordance with the angle between the direction in which the wire 110a4 of the assistance apparatus 100 extends and the direction in which the eighth wire 110a8 of the assistance apparatus 200 extends, and can be determined in accordance with the angles.

4. Example

An experiment was made for the assistance operation using the assistance apparatus 100 according to the embodiment to compare and verify timings of stopping assistance. Specifically, the assistance apparatus 100, which performed an operation according to the embodiment in the way illustrated in FIG. 25 to assist a user in walking, stopped assisting the left leg at four different timings. That is, the assistance apparatus 100 stopped assisting a user in walking while carrying no object by using the wire 110a1 or 110a2 at four different timings.

In Case 1, the assistance apparatus 100 stopped assistance with the second wire 110a2 during assistance for the left leg in the stance phase, that is, in a period of 0% or more and 20% or less of the gait phase of the left leg. In Case 2, the assistance apparatus 100 stopped assistance with the second wire 110a2 after the assistance for the left leg in the stance phase, that is, in a period of more than 20% and 40% or less of the gait phase of the left leg. In Case 3, the assistance apparatus 100 stopped assistance with the first wire 110a1 during assistance for the left leg in the swing phase, that is, in a period of 60% or more and 85% or less of the gait phase of the left leg. In Case 4, the assistance apparatus 100 stopped assistance with the first wire 110a1 after the assistance for the left leg in the swing phase, that is, in a period of more than 85% and less than 100% of the gait phase of the left leg. In each case, the assistance apparatus 100 controlled the tensions of the wires 110 in accordance with input profiles similar to those illustrated in FIG. 25. In Cases 1 to 4, the maximum tension that could be generated in each of the wires 110a1 to 110a4 was set to 100 N.

The experiment was conducted on four subjects A to D. The subjects A, C, and D were males, and the subject B was female. All the subjects A to D wearing the assistance apparatus 100 were stopped from receiving assistance in each case when the subjects A to D were walking forward while wearing the assistance apparatus 100. Then, the subjects A to D selected an operation that they felt less comfortable when assistance was stopped in each of Cases 1 to 4. The selection results are given in Table 1 below. Table 1 indicates that the timing in Case 2 is suitable for stopping assisting the leg to which assistance for extension is being applied and is included in the third stop period. Thus, as described with reference to FIG. 27A and FIG. 27B, the timing of stopping assisting extension of the left leg preferably falls within the third stop period. The timing in Case 3 is suitable for stopping assisting the leg to which assistance for flexion is being applied and is included in the first stop period. Thus, as described with reference to FIG. 26, the timing of stopping assisting flexion of the left leg preferably falls within the first stop period.

TABLE 1

Evaluation results of assistance based on operations in patterns

| Subject | Case 1 | Case 2 | Case 3 | Case 4 |
|---|---|---|---|---|
| A |  | Good | Good |  |
| B |  | Good | Good |  |
| C |  | Good | Good |  |
| D | Good | Good |  |  |

5. Other Embodiments

While an assistance apparatus and so on according to one or more aspects have been described in conjunction with an embodiment and a modification, the present disclosure is not limited to the embodiment and modification. Applications of various modifications conceived of by persons skilled in the art to this embodiment and modification and embodiments based on combinations of constituent elements in different embodiments and modifications may also be encompassed in the scope of one or more aspects as long as such applications or embodiments do not depart from the gist of the present disclosure.

For example, in the assistance apparatuses 100 and 200 according to the embodiment and modification, the timings at which the control unit 120 activates the motors 114 to generate tensions in the wires 110 and values of the gait phase regarding the input profiles of the tensions are not limited to the values described in the embodiment and modification. The timings and the values of the gait phase regarding the input profiles of the tensions may be different from those described in the embodiment and modification. For example, an error of several percent in terms of gait phase may occur.

In the assistance apparatuses 100 and 200 according to the embodiment and modification, each of the wires 110 is provided with a motor. However, the present disclosure is not limited to the embodiment and modification. One motor may be coupled to wires. For example, in the assistance apparatus 200, one motor may pull the wires 110a1 and 110a5. That is, the assistance apparatus 200 may include, for example, four motors so that one motor is provided for two wires.

In the assistance apparatuses 100 and 200 according to the embodiment and the modification, four wires or eight wires are used to couple the upper-body belt 111 to the knee belts 112a and 112b. That is, two wires or four wires are coupled to each knee belt. However, the number of wires to be coupled to each knee belt is not limited to that described above. Any number of wires more than one may be coupled to each knee belt. For example, the numbers of wires to be coupled to the front part and the back part of each knee belt may be different. Flexion of the left leg may mean flexion of the hip joint of the left leg. Flexion of the right leg may mean flexion of the hip joint of the right leg. Extension of the left leg may mean extension of the hip joint of the left leg. Extension of the right leg may mean extension of the hip joint of the right leg.

The present disclosure is applicable to an apparatus for assisting a user in changing direction.

What is claimed is:

1. An assistance apparatus comprising:
   an upper-body belt adapted to be worn on an upper half of a body of a user;
   a left knee belt adapted to be worn on a left knee of the user;
   a right knee belt adapted to be worn on a right knee of the user;
   a first wire adapted to couple the upper-body belt and the left knee belt to each other on or above a front part of the body of the user;
   a second wire adapted to couple the upper-body belt and the left knee belt to each other on or above a back part of the body of the user;
   a third wire adapted to couple the upper-body belt and the right knee belt to each other on or above the front part of the body of the user;
   a fourth wire adapted to couple the upper-body belt and the right knee belt to each other on or above the back part of the body of the user;
   a gait timing detection unit; and
   at least four motors, wherein
   in first assistance for assisting the user in walking while carrying an object,
   (i) a first motor of the at least four motors is configured to generate a tension greater than or equal to a first threshold value in the first wire during a first period, the first period being a period of 35% or more and 90% or less of an initial gait phase of a left leg of the user,
   (ii) a second motor of the at least four motors is configured to generate a tension greater than or equal to the first threshold value in the second wire during a second period, the second period being from a point in a range of 65% or more and less than 100% of the initial gait phase of the left leg to a point in a range of 0% or more and 25% or less of a subsequent gait phase of the left leg,
   (iii) a third motor of the at least four motors is configured to generate a tension greater than or equal to the first threshold value in the third wire during a third period, the third period being a period of 35% or more and 90% or less of an initial gait phase of a right leg of the user,
   (iv) a fourth motor of the at least four motors is configured to generate a tension greater than or equal to the first threshold value in the fourth wire during a fourth period, the fourth period being from a point in a range of 65% or more and less than 100% of the initial gait phase of the right leg to a point in a range of 0% or more and 25% or less of a subsequent gait phase of the right leg,
   (v) the first motor is configured to generate a tension less than a second threshold value in the first wire during a fifth period, the fifth period being from a point in a range of more than 90% and less than 100% of the initial gait phase of the left leg to a point in a range of 0% or more and less than 35% of the subsequent gait phase of the left leg,
   (vi) the second motor is configured to generate a tension greater than or equal to the second threshold value in the second wire during a sixth period, the sixth period being a period of more than 25% and less than 65% of the initial gait phase of the left leg,
   (vii) the third motor is configured to generate a tension less than the second threshold value in the third wire during a seventh period, the seventh period being from a point in a range of more than 90% and less than 100% of the initial gait phase of the right leg to a point in a range of 0% or more and less than 35% of the subsequent gait phase of the right leg, and
   (viii) the fourth motor is configured to generate a tension greater than or equal to the second threshold value in the fourth wire during an eighth period, the eighth period being a period of more than 25% and less than 65% of the initial gait phase of the right leg,
   the first threshold value is larger than the second threshold value,
   when the assistance apparatus stops the first assistance,
   the first motor is configured to make a tension of the first wire less than the first threshold value during a first stop period, the first stop period being a period starting in a boundary period in the first period and ending in a start period of the second period, and the second motor is configured not to generate a tension greater than or equal to the first threshold value in the second wire during the second period, and
   the third motor is configured to make a tension of the third wire less than the first threshold value during a second stop period, the second stop period being a period starting in a boundary period in the third period and ending in a start period of the fourth period, and the fourth motor is configured not to generate a tension greater than or equal to the first threshold value in the fourth wire during the fourth period,
   the boundary period in the first period includes a timing at which the left leg shifts from a stance phase to a swing phase,
   the boundary period in the third period includes a timing at which the right leg shifts from the stance phase to the swing phase, and
   the gait timing detection unit is configured to determine, based on information obtained using a sensor, time points of respective percentages of the initial gait phase of the left leg, time points of respective percentages of the subsequent gait phase of the left leg, time points of respective percentages of the initial gait phase of the right leg, and time points of respective percentages of the subsequent gait phase of the right leg.

2. The assistance apparatus according to claim 1, wherein
   the left leg shifts from the stance phase to the swing phase during the first period,
   the left leg shifts from the swing phase to the stance phase during the second period,
   the right leg shifts from the stance phase to the swing phase during the third period, and
   the right leg shifts from the swing phase to the stance phase during the fourth period.

3. The assistance apparatus according to claim 1, wherein the first stop period and the second stop period do not overlap.

4. The assistance apparatus according to claim 1, wherein
the first stop period comprises a period of 55% or more and 95% or less of the initial gait phase of the left leg, and
the second stop period comprises a period of 55% or more and 95% or less of the initial gait phase of the right leg.

5. The assistance apparatus according to claim 1, wherein when the assistance apparatus stops the first assistance,
the first motor is configured to make the tension of the first wire less than the second threshold value during the first stop period and the second motor is configured to keep the tension of the second wire greater than or equal to the second threshold value during the second period,
the third motor is configured to make the tension of the third wire less than the second threshold value during the second stop period and the fourth motor is configured to keep the tension of the fourth wire greater than or equal to the second threshold value during the fourth period, and
the second motor is configured to decrease the tension of the second wire and the fourth motor is configured to decrease the tension of the fourth wire to a tension less than the second threshold value after the first stop period and the second stop period, respectively.

6. The assistance apparatus according to claim 5, wherein
the second motor is configured to start decreasing the tension of the second wire and the fourth motor is configured to start decreasing the tension of the fourth wire after the first stop period and the second stop period, respectively, the second motor is configured to progressively decrease the tension of the second wire in accordance with progression of the initial gait phase of the left leg and the subsequent gait phase of the left leg, and the fourth motor is configured to progressively decrease the tension of the fourth wire in accordance with progression of the initial gait phase of the right leg and the subsequent gait phase of the right leg.

7. The assistance apparatus according to claim 1, wherein
the first wire has a first end fixed to the left knee belt,
the first wire has a second end fixed to the first motor,
the second wire has a first end fixed to the left knee belt,
the second wire has a second end fixed to the second motor,
the third wire has a first end fixed to the right knee belt,
the third wire has a second end fixed to the third motor,
the fourth wire has a first end fixed to the right knee belt, and
the fourth wire has a second end fixed to the fourth motor.

8. The assistance apparatus according to claim 1, further comprising:
a fifth wire adapted to couple the upper-body belt and the left knee belt to each other and extend on or above the front part of the body of the user in a direction crossing a direction in which the first wire extends;
a sixth wire adapted to couple the upper-body belt and the left knee belt to each other and extend on or above the back part of the body of the user in a direction crossing a direction in which the second wire extends;
a seventh wire adapted to couple the upper-body belt and the right knee belt to each other and extend on or above the front part of the body of the user in a direction crossing a direction in which the third wire extends; and
an eighth wire adapted to couple the upper-body belt and the right knee belt to each other and extend on or above the back part of the body of the user in a direction crossing a direction in which the fourth wire extends, wherein
the at least four motors include at least eight motors, and in the first assistance,
(i) the first motor is configured to generate a tension greater than or equal to the first threshold value in the first wire during the first period and a fifth motor of the at least eight motors is configured to generate a tension greater than or equal to the first threshold value in the fifth wire during the first period,
(ii) the second motor is configured to generate a tension greater than or equal to the first threshold value in the second wire during the second period and a sixth motor of the at least eight motors is configured to generate a tension greater than or equal to the first threshold value in the sixth wire during the second period,
(iii) the third motor is configured to generate a tension greater than or equal to the first threshold value in the third wire during the third period and a seventh motor of the at least eight motors is configured to generate a tension greater than or equal to the first threshold value in the seventh wire during the third period,
(iv) the fourth motor is configured to generate a tension greater than or equal to the first threshold value in the fourth wire during the fourth period and an eighth motor of the at least eight motors is configured to generate a tension greater than or equal to the first threshold value in the eighth wire during the fourth period,
(v) the first motor is configured to generate a tension less than the second threshold value in the first wire during the fifth period and the fifth motor is configured to generate a tension less than the second threshold value in the fifth wire during the fifth period,
(vi) the second motor is configured to generate a tension greater than or equal to the second threshold value in the second wire during the sixth period and the sixth motor is configured to generate a tension greater than or equal to the second threshold value in the sixth wire during the sixth period,
(vii) the third motor is configured to generate a tension less than the second threshold value in the third wire during the seventh period and the seventh motor is configured to generate a tension less than the second threshold value in the seventh wire during the seventh period, and
(viii) the fourth motor is configured to generate a tension greater than or equal to the second threshold value in the fourth wire during the eighth period and the eighth motor is configured to generate a tension greater than or equal to the second threshold value in the eighth wire during the eighth period.

9. The assistance apparatus according to claim 1, wherein
a time point of 50% of the initial gait phase of the left leg determined by the gait timing detection unit based on the information obtained using the sensor corresponds to a time point of 0% of the initial gait phase of the right leg determined by the gait timing detection unit based on the information obtained using the sensor, and
a time point of 50% of the initial gait phase of the right leg determined by the gait timing detection unit based on the information obtained using the sensor corresponds to a time point of 0% of the initial gait phase of the left leg determined by the gait timing detection unit based on the information obtained using the sensor.

10. The assistance apparatus according to claim 1, further comprising:
a control circuit; and
a memory, wherein
the memory stores a program for controlling the at least four motors, and
the control circuit is configured to control the at least four motors in accordance with the program.

11. The assistance apparatus according to claim 10, further comprising
the sensor, wherein
the control circuit is configured to calculate, based on the information obtained using the sensor, the initial gait phase of the left leg, the subsequent gait phase of the left leg, the initial gait phase of the right leg and the subsequent gait phase of the right leg.

12. The assistance apparatus according to claim 10, further comprising
an interface device, wherein
the control circuit is configured to accept selection of an assistance method including the first assistance via the interface device, and
the control circuit is configured to control the at least four motors in accordance with the assistance method.

13. An assistance method for assisting a movement of a user by using wires attached to a body of the user, the assistance method comprising:
coupling, using a first wire among the wires, an upper-body belt and a left knee belt to each other on or above a front part of the body of the user, the upper-body belt being a belt adapted to be worn on an upper half of the body of the user, the left knee belt being a belt adapted to be worn on a left knee of the user;
coupling, using a second wire among the wires, the upper-body belt and the left knee belt to each other on or above a back part of the body of the user;
coupling, using a third wire among the wires, the upper-body belt and a right knee belt to each other on or above the front part of the body of the user, the right knee belt being a belt adapted to be worn on a right knee of the user; and
coupling, using a fourth wire among the wires, the upper-body belt and the right knee belt to each other on or above the back part of the body of the user,
wherein, in first assistance for assisting the user in walking while carrying an object,
generating, using a first motor of at least four motors, a tension greater than or equal to a first threshold value in the first wire during a first period, the first period being a period of 35% or more and 90% or less of an initial gait phase of a left leg of the user;
generating, using a second motor of the at least four motors, a tension greater than or equal to the first threshold value in the second wire during a second period, the second period being from a point in a range of 65% or more and less than 100% of the initial gait phase of the left leg to a point in a range of 0% or more and 25% or less of a subsequent gait phase of the left leg;
generating, using a third motor of the at least four motors, a tension greater than or equal to the first threshold value in the third wire during a third period, the third period being a period of 35% or more and 90% or less of an initial gait phase of a right leg of the user;
generating, using a fourth motor of the at least four motors, a tension greater than or equal to the first threshold value in the fourth wire during a fourth period, the fourth period being from a point in a range of 65% or more and less than 100% of the initial gait phase of the right leg to a point in a range of 0% or more and 25% or less of a subsequent gait phase of the right leg;
generating, using the first motor, a tension less than a second threshold value in the first wire during a fifth period, the fifth period being from a point in a range of more than 90% and less than 100% of the initial gait phase of the left leg to a point in a range of 0% or more and less than 35% of the subsequent gait phase of the left leg;
generating, using the second motor, a tension greater than or equal to the second threshold value in the second wire during a sixth period, the sixth period being a period of 0% or more than 25% and less than 65% of the initial gait phase of the left leg;
generating, using the third motor, a tension less than the second threshold value in the third wire during a seventh period, the seventh period being from a point in a range of more than 90% and less than 100% of the initial gait phase of the right leg to a point in a range of 0% or more and less than 35% of the subsequent gait phase of the right leg; and
generating, using the fourth motor, a tension greater than or equal to the second threshold value in the fourth wire during an eighth period, the eighth period being a period of 0% or more than 25% and less than 65% of the initial gait phase of the right leg,
the first threshold value being larger than the second threshold value,
wherein, when stopping the first assistance,
making, using the first motor, a tension of the first wire less than the first threshold value during a first stop period, the first stop period being a period starting in a boundary period in the first period and ending in a start period of the second period, and not generating, using the second motor, a tension greater than or equal to the first threshold value in the second wire during the second period; and
making, using the third motor, a tension of the third wire less than the first threshold value during a second stop period, the second stop period being a period starting in a boundary period in the third period and ending in a start period of the fourth period, and not generating, using the fourth motor, a tension greater than or equal to the first threshold value in the fourth wire during the fourth period, wherein
the boundary period in the first period includes a timing at which the left leg of the user shifts from a stance phase to a swing phase,
the boundary period in the third period includes a timing at which the right leg of the user shifts from the stance phase to the swing phase,
the at least four motors are controlled by a control circuit, and
a gait timing detection unit determines, based on information obtained using a sensor, time points of respective percentages of the initial gait phase of the left leg, time points of respective percentages of the subsequent gait phase of the left leg, time points of respective percentages of the initial gait phase of the right leg, and time points of respective percentages of the subsequent gait phase of the right leg.

14. The assistance method according to claim 13, wherein
the left leg shifts from the stance phase to the swing phase during the first period,
the left leg shifts from the swing phase to the stance phase during the second period,
the right leg shifts from the stance phase to the swing phase during the third period, and
the right leg shifts from the swing phase to the stance phase during the fourth period.

15. The assistance method according to claim 13, wherein the first stop period and the second stop period do not overlap.

16. The assistance method according to claim 13, wherein
the first stop period comprises a period of 55% or more and 95% or less of the initial gait phase of the left leg, and
the second stop period comprises a period of 55% or more and 95% or less of the initial gait phase of the right leg.

17. The assistance method according to claim 13, further comprising:
when stopping the first assistance,
making, using the first motor, the tension of the first wire less than the second threshold value during the first stop period and keeping, using the second motor, the tension of the second wire greater than or equal to the second threshold value during the second period;
making, using the third motor, the tension of the third wire less than the second threshold value during the second stop period and keeping, using the fourth motor, the tension of the fourth wire greater than or equal to the second threshold value during the fourth period; and
decreasing, using the second motor, the tension of the second wire and decreasing, using the fourth motor, the tension of the fourth wire to a tension less than the second threshold value after the first stop period and the second stop period, respectively.

18. The assistance method according to claim 17, wherein
the tension of the second wire is started to decrease by the second motor and the tension of the fourth wire is started to decrease by the fourth motor after the first stop period and the second stop period, respectively, and
the tension of the second wire is progressively decreased by the second motor in accordance with progression of the initial gait phase of the left leg and the subsequent gait phase of the left leg, and the tension of the fourth wire is progressively decreased by the fourth motor in accordance with progression of the initial gait phase of the right leg and the subsequent gait phase of the right leg.

19. The assistance method according to claim 13, wherein
a first end of the first wire is fixed to the left knee belt,
a second end of the first wire is fixed to the first motor,
a first end of the second wire is fixed to the left knee belt,
a second end of the second wire is fixed to the second motor,
a first end of the third wire is fixed to the right knee belt,
a second end of the third wire is fixed to the third motor,
a first end of the fourth wire is fixed to the right knee belt, and
a second end of the fourth wire is fixed to the fourth motor.

20. The assistance method according to claim 13, further comprising:
coupling, using a fifth wire among the wires, the upper-body belt and the left knee belt to each other, the fifth wire extending on or above the front part of the body of the user in a direction crossing a direction in which the first wire extends;
coupling, using a sixth wire among the wires, the upper-body belt and the left knee belt to each other, the sixth wire extending on or above the back part of the body of the user in a direction crossing a direction in which the second wire extends;
coupling, using a seventh wire among the wires, the upper-body belt and the right knee belt to each other, the seventh wire extending on or above the front part of the body of the user in a direction crossing a direction in which the third wire extends; and
coupling, using an eighth wire among the wires, the upper-body belt and the right knee belt to each other, the eighth wire extending on or above the back part of the body of the user in a direction crossing a direction in which the fourth wire extends, and
the at least four motors including at least eight motors, and
in the first assistance,
generating, using the first motor, a tension greater than or equal to the first threshold value in the first wire during the first period and generating, using a fifth motor of the at least eight motors, a tension greater than or equal to the first threshold value in the fifth wire during the first period;
generating, using the second motor, a tension greater than or equal to the first threshold value in the second wire during the second period and generating, using a sixth motor of the at least eight motors, a tension greater than or equal to the first threshold value in the sixth wire during the second period;
generating, using the third motor, a tension greater than or equal to the first threshold value in the third wire during the third period and generating, using a seventh motor of the at least eight motors, a tension greater than or equal to the first threshold value in the seventh wire during the third period;
generating, using the fourth motor, a tension greater than or equal to the first threshold value in the fourth wire during the fourth period and generating, using an eighth motor of the at least eight motors, a tension greater than or equal to the first threshold value in the eighth wire during the fourth period;
generating, using the first motor, a tension less than the second threshold value in the first wire during the fifth period and generating, using the fifth motor, a tension less than the second threshold value in the fifth wire during the fifth period;
generating, using the second motor, a tension greater than or equal to the second threshold value in the second wire during the sixth period and generating, using the sixth motor, a tension greater than or equal to the second threshold value in the sixth wire during the sixth period;
generating, using the third motor, a tension less than the second threshold value in the third wire during the seventh period and generating, using the seventh motor, a tension less than the second threshold value in the seventh wire during the seventh period; and
generating, using the fourth motor, a tension greater than or equal to the second threshold value in the fourth wire during the eighth period and generating, using the eighth motor, a tension greater than or equal to the second threshold value in the eighth wire during the eighth period.

21. The assistance method according to claim 13, wherein
a time point of 50% of the initial gait phase of the left leg determined by the gait timing detection unit based on the information obtained using the sensor corresponds to a time point of 0% of the initial gait phase of the right leg determined by the gait timing detection unit based on the information obtained using the sensor, and
a time point of 50% of the initial gait phase of the right leg determined by the gait timing detection unit based on the information obtained using the sensor corresponds to a time point of 0% of the initial gait phase of the left leg determined by the gait timing detection unit based on the information obtained using the sensor.

22. The assistance method according to claim 13, further comprising:
calculating, based on the information obtained using the sensor, the initial gait phase of the left leg, the subsequent gait phase of the left leg, the initial gait phase of the right leg and the subsequent gait phase of the right leg.

23. The assistance method according to claim 13, further comprising:
accepting selection of an assistance method including the first assistance via an interface device; and
in accordance with the assistance method generating a tension in the first wire using the first motor, generating a tension in the second wire using the second motor, generating a tension in the third wire using the third motor, and generating a tension in the fourth wire using the fourth motor.

24. A non-transitory computer-readable recording medium storing a control program for causing an assistance apparatus including a processor to execute a process, the control program being used in the assistance apparatus including
a first wire adapted to couple an upper-body belt and a left knee belt to each other on or above a front part of a body of a user, the upper-body belt being adapted to be worn on an upper half of the body of the user, the left knee belt being adapted to be worn on a left knee of the user,
a second wire adapted to couple the upper-body belt and the left knee belt to each other on or above a back part of the body of the user,
a third wire adapted to couple the upper-body belt and a right knee belt to each other on or above the front part of the body of the user, the right knee belt being adapted to be worn on a right knee of the user,
a fourth wire adapted to couple the upper-body belt and the right knee belt to each other on or above the back part of the body of the user, and
a gait timing detection unit configured to determine, based on information obtained using a sensor, time points of respective percentages of an initial gait phase of a left leg of the user, time points of respective percentages of a subsequent gait phase of the left leg, time points of respective percentages of an initial gait phase of a right leg of the user, and time points of respective percentages of a subsequent gait phase of the right leg,
the process comprising:
in first assistance for assisting the user in walking while carrying an object,
causing a first motor of at least four motors to generate a tension greater than or equal to a first threshold value in the first wire during a first period, the first period being a period of 35% or more and 90% or less of the initial gait phase of the left leg;
causing a second motor of the at least four motors to generate a tension greater than or equal to the first threshold value in the second wire during a second period, the second period being from a point in a range of 65% or more and less than 100% of the initial gait phase of the left leg to a point in a range of 0% or more and 25% or less of a subsequent gait phase of the left leg;
causing a third of the at least four motors to generate a tension greater than or equal to the first threshold value in the third wire during a third period, the third period being a period of 35% or more and 90% or less of the initial gait phase of the right leg;
causing a fourth of the at least four motors to generate a tension greater than or equal to the first threshold value in the fourth wire during a fourth period, the fourth period being from a point in a range of 65% or more and less than 100% of the initial gait phase of the right leg to a point in a range of 0% or more and 25% or less of a subsequent gait phase of the right leg;
causing the first motor to generate a tension less than a second threshold value in the first wire during a fifth period, the fifth period being from a point in a range of more than 90% and less than 100% of the initial gait phase of the left leg to a point in a range of 0% or more and less than 35% of the subsequent gait phase of the left leg;
causing the second motor to generate a tension greater than or equal to the second threshold value in the second wire during a sixth period, the sixth period being a period of more than 25% and less than 65% of the initial gait phase of the left leg;
causing the third motor to generate a tension less than the second threshold value in the third wire during a seventh period, the seventh period being from a point in a range of more than 90% and less than 100% of the initial gait phase of the right leg to a point in a range of 0% or more and less than 35% of the subsequent gait phase of the right leg;
causing the fourth motor to generate a tension greater than or equal to the second threshold value in the fourth wire during an eighth period, the eighth period being a period of more than 25% and less than 65% of the initial gait phase of the right leg,
the first threshold value being larger than the second threshold value; and
when stopping the first assistance,
causing the first motor to make a tension of the first wire less than the first threshold value during a first stop period, the first stop period being a period starting in a boundary period in the first period and ending in a start period of the second period, and causing the second motor not to generate a tension greater than or equal to the first threshold value in the second wire during the second period; and
causing the third motor to make a tension of the third wire less than the first threshold value during a second stop period, the second stop period being a period starting in a boundary period in the third period and ending in a start period of the fourth period, and causing the fourth motor not to generate a tension greater than or equal to the first threshold value in the fourth wire during the fourth period, wherein
the boundary period in the first period includes a timing at which the left leg of the user shifts from a stance phase to a swing phase, and the boundary period in the third period includes a timing at which the right leg of the user shifts from the stance phase to the swing phase.

25. An assistance apparatus, comprising:
a first belt adapted to be worn on an upper half of a body of a user;
a left knee belt adapted to be worn above a left knee of the user;
a right knee belt adapted to be worn above a right knee of the user;
a first wire adapted to couple the first belt with the left knee belt on or above a front part of the body;
a second wire adapted to couple the first belt with the left knee belt on or above a back part of the body;
a third wire adapted to couple the first belt with the right knee belt on or above the front part;
a fourth wire adapted to couple the first belt with the right knee belt on or above the back part;
a gait timing detection unit;
at least four motors; and
a controller,
wherein in assistance for assisting the user in walking forward,
(a) a first motor of the at least four motors is configured to generate a first tension on the first wire during a first period, the first period being from a first value in a first percentage range of a TL(i) to a second value in a second percentage range of the TL(i), the TL(i) being an ith gait cycle of a left leg of the user, the first percentage range being 35 percent or more and 55 percent or less, the second percentage range being 80 percent or more and 90 percent or less, a maximum magnitude of the first tension being a first threshold value or more,
(b) a second motor of the at least four motors is configured to generate a second tension on the second wire during a second period, the second period being from a third value in a third percentage range of the TL(i) to a fourth value in a fourth percentage range of a TL(i+1), the third percentage range being 65 percent or more and 90 percent or less, the fourth percentage range being 10 percent or more and 25 percent or less, a maximum magnitude of the second tension being the first threshold value or more,
(c) a third motor of the at least four motors is configured to generate a third tension on the third wire during a third period, the third period being from a fifth value in a fifth percentage range of a TR(i) to a sixth value in a sixth percentage range of the TR(i), the TR(i) being an ith gait cycle of a right leg of the user, the fifth percentage range being 35 percent or more and 55 percent or less, the sixth percentage range being 80 percent or more and 90 percent or less, a maximum magnitude of the third tension being the first threshold value or more, the TR(i) starting between zero percent of the TL(i) and zero percent of the TL(i+1),
(d) a fourth motor of the at least four motors is configured to generate a fourth tension on the fourth wire during a fourth period, the fourth period being from a seventh value in a seventh percentage range of the TR(i) to an eighth value in an eighth percentage range of a TR(i+1), the seventh percentage range being 65 percent or more and 90 percent or less, the eighth percentage range being 10 percent or more and 25 percent or less, a maximum magnitude of the fourth tension being the first threshold value or more,
(e) the first motor is configured to generate a fifth tension on the first wire during a fifth period, the fifth period being from the second value in the second percentage range of the TL(i) to a value in the TL(i+1) corresponding to the first value in the first percentage range of the TL(i), a maximum magnitude of the fifth tension being less than a second threshold value,
(f) the second motor is configured to generate a sixth tension on the second wire during the sixth period being from the fourth value in the fourth percentage range of the TL(i+1) to a value in the TL(i+1) corresponding to the third value in the third percentage range of the TL(i), a maximum magnitude of the sixth tension being the second threshold value or more,
(g) the third motor is configured to generate a seventh tension on the third wire during a seventh period, the seventh period being from the sixth value in the sixth percentage range of the TR(i) to a value in a TR(i+1) corresponding to the fifth value in the fifth percentage range of the TR(i), a maximum magnitude of the seventh tension being less than the second threshold value, and
(h) the fourth motor is configured to generate an eighth tension on the fourth wire during the eighth period being from the eighth value in the eighth percentage range of the TR(i+1) to a value in the TR(i+1) corresponding to the seventh value in the seventh percentage range of the TR(i), a maximum magnitude of the eighth tension being the second threshold value or more,
wherein the first threshold value is bigger than the second threshold value,
wherein when the assistance apparatus stops the assistance during TL(j) and TR(j), in which the i< the j, the i and the j being natural numbers,
the first motor is configured to stop generating a tension on the first wire from a first time included in the first period, the first time being bigger than 55 percent of the TL(j), the first time not being included in the second period, and
the third motor is configured to stop generating a tension on the third wire from a third time included in the third period, the third time being bigger than 55 percent of the TR(j), the third time not being included in the fourth period of the TR(j), and
wherein the gait timing detection unit is configured to determine, based on information obtained using a sensor, time points of respective percentages of the TL(i), time points of respective percentages of the TL(i+1), time points of respective percentages of the TR(i), and time points of respective percentages of the TR(i+1).

* * * * *